(12) United States Patent
Crooks et al.

(10) Patent No.: US 8,178,678 B2
(45) Date of Patent: May 15, 2012

(54) *BIS*-QUATERNARY AMMONIUM SALTS AND METHODS FOR MODULATING NEURONAL NICOTINIC ACETYLCHOLINE RECEPTORS

(75) Inventors: Peter Crooks, Nicholasville, KY (US); Linda P. Dwoskin, Lexington, KY (US); Guangrong Zheng, Lexington, KY (US); Zhenfa Zhang, Lexington, KY (US); Sangeetha Sumithran, Lexington, KY (US); Marharyta Pivavarchyk, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 167 days.

(21) Appl. No.: 12/304,948

(22) PCT Filed: May 14, 2007

(86) PCT No.: PCT/US2007/011635
§ 371 (c)(1),
(2), (4) Date: Nov. 30, 2009

(87) PCT Pub. No.: WO2007/149163
PCT Pub. Date: Dec. 27, 2007

(65) Prior Publication Data
US 2010/0069432 A1 Mar. 18, 2010

Related U.S. Application Data

(60) Provisional application No. 60/814,640, filed on Jun. 16, 2006.

(51) Int. Cl.
*C07D 217/00* (2006.01)
*C07D 401/00* (2006.01)

(52) U.S. Cl. ........................................ 546/140; 546/256

(58) Field of Classification Search .................. 546/140, 546/256
See application file for complete search history.

(56) References Cited

U.S. PATENT DOCUMENTS

| | | | | |
|---|---|---|---|---|
| 5,382,496 | A | * | 1/1995 | Sakai et al. .................. 430/264 |
| 5,929,093 | A | * | 7/1999 | Pang et al. .................. 514/332 |
| 7,414,135 | B2 | * | 8/2008 | Huang et al. ................. 546/256 |
| 2005/0261334 | A1 | | 11/2005 | Crooks et al. |

OTHER PUBLICATIONS

Zueva et al. Khimiko—Farmatsevticheskii Zhurnal, 2003, 37(11), 582-584. NPL filed Jan. 30, 2009.*
International Search Report dated Aug. 1, 2008 (Four (4) pages).
Engelhard et al., "Relation between chemical structure and cholinesterase-reactivating effect in a series of new bisquaternary pyridine-4-aldoximes", STN accession No. 1965:11382 document No. 62:11382, Abstract of relation between chemical structure and cholinesterasereactivating effect in a series of new bisquaternary pyridine-4-aldoxines, Arzneimattel-Forschung (1964), 14, 870-5; Fig. 2 and 5.
Zueva et al., "Synthesis and Antibacterial Activity of N-Alkylpyridinium Podands", STN accession No. 2004: 124600; Document No. 141:243306, Abstract of Synthesis and Antibacertial Activity of N-Alkylpyridinium Podands, Khimiko-Farmatsevticheskii Zhurnal, (2003), 37(11), 582-584. CAS Registry Nos. 752233-92-4; 752233-98-0.

* cited by examiner

*Primary Examiner* — Nizal Chandrakumar
(74) *Attorney, Agent, or Firm* — Crowell & Moring LLP

(57) ABSTRACT

Provided are bis-quaternary ammonium compounds which are modulators of nicotinic acetylcholine receptors. Also provided are methods of using the compounds for modulating the function of a nicotinic acetylcholine receptor, and for the prevention and/or treatment of central nervous system disorders, substance use and/or abuse, and or gastrointestinal tract disorders.

10 Claims, No Drawings

BIS-QUATERNARY AMMONIUM SALTS AND METHODS FOR MODULATING NEURONAL NICOTINIC ACETYLCHOLINE RECEPTORS

CONTINUING APPLICATION DATA

This application claims benefit of U.S. Provisional Application No. 60/814,640, filed Jun. 16, 2006, which is incorporated herein by reference in its entirety.

IDENTIFICATION OF FEDERAL FUNDING

The present invention was supported by Grant NIH U19DA017548 from the National Institutes of Health, and therefore the government may have rights in the invention.

FIELD OF THE INVENTION

The invention relates to bis-quaternary ammonium salts and their use in modulating nicotinic acetylcholine receptors.

BACKGROUND OF THE INVENTION

S-Nicotine (NIC) activates presynaptic and postsynaptic neuronal nicotinic receptors that evoke the release of neurotransmitters from presynaptic terminals and that modulate the depolarization state of the postsynaptic neuronal membrane, respectively. Thus, S-nicotine produces its effect by binding to a family of ligand-gated ion channels, stimulated by acetylcholine (ACh) or S-nicotine which causes the ion channel to open and cations to flux with a resulting rapid (millisecond) depolarization of the target cell.

Neuronal nicotinic receptors are composed of two types of subunits, α and β, and assemble as heteromeric receptors with the general stoichiometry of 2α and 3β or as homomeric receptors with 5α subunits. Nine subtypes of the α subunit (α2 to α10) and three subtypes of the β unit (β2 to β4) are found in the central nervous system. The most common nicotinic receptor subtype in the brain is composed of two α4 and three β2 subunits, i.e., α4β2. These subunits display different, but overlapping, patterns of expression in the brain. Examples of heteromeric receptor subtypes include α4β2, α3β2, α3β4, α6β2, α6β2β3, α4α5β2, α6α5β2, α6α4β2, α6α4β2β3, α4β2β4, 3β2β4, and others. The predominant homomeric subtype includes α7, but other combinations have also been proposed.

For the most part, the actual subunit compositions and stoichiometries of nicotinic receptors in the brain remain to be elucidated. Thus, neuronal nicotinic receptor subtype diversity originates from differences in the amino acid sequence at the subunit level and from the multiple combinations of assemblies of subunits into functional receptor proteins, which affords a wide diversity of pharmacological specificity.

In spite of the extensive diversity in neuronal nicotinic receptor messenger RNA expression, only a limited number of tools are available to study the pharmacology of native receptors. Radioligands are used in many studies. [$^3$H]NIC appears to label the same sites in the brain as [$^3$H]ACh. It has been estimated that over 90% of [$^3$H]NIC binding in the brain is due to association with the heteromeric receptor that is composed of α4 and β2 subunits. Also abundant in the central nervous system are the homomeric receptors labeled by [$^3$H] methyllycaconitine (MLA), which has high affinity for the α7 nicotinic receptor subtype. Nicotinic receptor subtypes can be studied using functional assays, such as NIC-evoked neurotransmitter release (e.g., [$^3$H]dopamine (DA) release, [$^3$H] norepinephrine (NE) release, [$^3$H]serotonin (5-HT) release, [$^3$H]gamma-aminobutyric acid (GABA) release and [$^3$H] glutamate release) from superfused rat brain slices. Nicotinic receptors are located in the cell body and terminal areas of these neurotransmitter systems. NIC facilitates neurotransmitter release from nerve terminals.

The structural and functional diversity of central nervous system nicotinic receptors has stimulated a great deal of interest in developing novel, subtype-selective agonists and/or antagonists. Some of these agonists are currently being evaluated in clinical trials for cognitive enhancement and neuroprotective effects, potentially beneficial for disease states such as Alzheimer's and Parkinson's disease, as well for treatment of drug abuse, depression, obesity and pain relief.

SUMMARY OF INVENTION

In one embodiment, compounds corresponding to the following structure are provided.

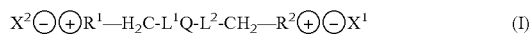

$$X^2\ominus\oplus R^1-H_2C-L^1Q-L^2-CH_2-R^2\oplus\ominus X^1 \quad (I)$$

$X^1\ominus$ and $X^2\ominus$ are each independently an organic or inorganic anion.

Q is selected from phenylene, biphenylene, —CH═CH—, —CH═CH—CH═CH—, —C≡C—, —C≡C—C≡C—, —O—(CH$_2$)$_2$—O—, and —O—(CH$_2$)$_2$—O—(CH$_2$)$_2$—O—.

$L^1$ and $L^2$ are each independently selected from alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic; SOY$^1$, SO$_2$Y$^1$, SO$_2$OY$^1$ or SO$_2$NHY$^1$, where Y$^1$ is selected from hydrogen, lower alkyl, alkenyl, alkynyl or aryl, and where Y$^1$ is not hydrogen in SOY$^1$ and if Y$^1$ is alkenyl or alkynyl, the site of unsaturation is not conjugated with a heteroatom; COY$^2$, where Y$^2$ is selected from hydrogen, alkyl, substituted alkyl, cycloalkyl, substituted cycloalkyl, alkoxy, alkenyl, substituted alkenyl, alkynyl, substituted alkynyl, aryl, substituted aryl, aryloxy, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if Y$^2$ comprises alkenyl or alkynyl, the site of unsaturation is not conjugated with the carbonyl group; OY$^3$, where Y$^3$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, alkylsulfonyl, arylsulfonyl, heterocyclic, or substituted heterocyclic, where if Y$^3$ comprises alkenyl or alkynyl, the site of unsaturation is not conjugated with the oxygen; NY$^4$Y$^5$, where Y$^4$ and Y$^5$ are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, alkylsulfonyl, arylsulfonyl, heterocyclic, or substituted heterocyclic, where if Y$^4$ or Y$^5$ comprises alkenyl or alkynyl, the site of unsaturation is not conjugated with the nitrogen; SY$^6$, where Y$^6$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^6$ comprises alkenyl or alkynyl, the site of unsaturation is not conjugated with the sulfur.

$R^1$ and $R^2$ are each independently five or six membered nitrogen containing rings as shown in formulas (IIA) and (IIB).

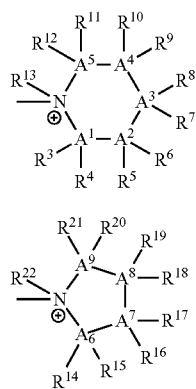

$A^1$ is carbon, nitrogen, sulfur or oxygen, provided that when $A^1$ is a carbon and joins a ring atom with an unsaturated bond or is a nitrogen, $R^3$ is absent, and when $A^1$ is sulfur or oxygen or joins a ring atom with an unsaturated bond and is a nitrogen, both $R^3$ and $R^4$ are absent.

$A^2$ is carbon, nitrogen, sulfur or oxygen, provided that when $A^2$ is a carbon and joins a ring atom with an unsaturated bond or is a nitrogen, $R^5$ is absent, and when $A^2$ is sulfur or oxygen or joins a ring atom with an unsaturated bond and is a nitrogen, both $R^5$ and $R^6$ are absent.

$A^3$ is carbon, nitrogen, sulfur or oxygen, provided that when $A^3$ is a carbon and joins a ring atom with an unsaturated bond or is a nitrogen, $R^7$ is absent, and when $A^3$ is sulfur or oxygen or joins a ring atom with an unsaturated bond and is a nitrogen, both $R^7$ and $R^8$ are absent.

$A^4$ is carbon, nitrogen, sulfur or oxygen, provided that when $A^4$ is a carbon and joins a ring atom with an unsaturated bond or is a nitrogen, $R^9$ is absent, and when $A^4$ is sulfur or oxygen or joins a ring atom with an unsaturated bond and is a nitrogen, both $R^9$ and $R^{10}$ are absent.

$A^5$ is carbon, nitrogen, sulfur or oxygen, provided that when $A^5$ is a carbon and joins a ring atom with an unsaturated bond or is a nitrogen, $R^{11}$ is absent, and when $A^5$ is sulfur or oxygen or joins a ring atom with an unsaturated bond and is a nitrogen, both $R^{11}$ and $R^{12}$ are absent.

$A^6$ is carbon, nitrogen, sulfur or oxygen, provided that when $A^6$ is a carbon and joins a ring atom with an unsaturated bond or is a nitrogen, $R^{14}$ is absent, and when $A^6$ is sulfur or oxygen or joins a ring atom with an unsaturated bond and is a nitrogen, both $R^{14}$ and $R^{15}$ are absent.

$A^7$ is carbon, nitrogen, sulfur or oxygen, provided that when $A^7$ is a carbon and joins a ring atom with an unsaturated bond or is a nitrogen, $R^{16}$ is absent, and when $A^7$ is sulfur or oxygen or joins a ring atom with an unsaturated bond and is a nitrogen, both $R^{16}$ and $R^{17}$ are absent.

$A^8$ is carbon, nitrogen, sulfur or oxygen, provided that when $A^8$ is a carbon and joins a ring atom with an unsaturated bond or is a nitrogen, $R^{18}$ is absent, and when $A^8$ is sulfur or oxygen or joins a ring atom with an unsaturated bond and is a nitrogen, both $R^{18}$ and $R^{19}$ are absent.

$A^9$ is carbon, nitrogen, sulfur or oxygen, provided that when $A^9$ is a carbon and joins a ring atom with an unsaturated bond or is a nitrogen, $R^{20}$ is absent, and when $A^9$ is sulfur or oxygen or joins a ring atom with an unsaturated bond and is a nitrogen, both $R^{20}$ and $R^{21}$ are absent.

$R^{13}$ or $R^{22}$ is absent when any of the bonds to the ammonium nitrogen is unsaturated, and $R^{13}$ or $R^{22}$ is a straight chain or branched alkyl group of four carbons or fewer when all of the bonds to the ammonium nitrogen are saturated.

$R^3$ $R^4$, $R^5$ $R^6$, $R^7$, $R^8$, $R^9$, $R^{10}$, $R^{11}$, and $R^{12}$ or $R^{14}$, $R^{15}$, $R^{16}$, $R^{17}$, $R^{18}$, $R^{19}$, $R^{20}$, and $R^{21}$, when present, are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, halo, cyano, nitro, or $R^4$ and $R^5$ together with $A^1$ and $A^2$, or $R^5$ and $R^7$ together with $A^2$ and $A^3$, or $R^{15}$ and $R^{16}$ together with $A^6$ and $A^7$, or $R^{16}$ and $R^{18}$ together with $A^7$ and $A^8$ independently form a three to eight member cyclolkane, substituted cycloalkane, cycloalkene, substituted cycloalkene, aryl, substituted aryl, heterocycle with one to three hetero atoms of nitrogen, oxygen or sulfur in the ring, or substituted heterocycle with one to three hetero atoms of nitrogen, oxygen or sulfur in the ring; and when all of the bonds to the ring ammonium nitrogen are saturated, then any of $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ or $R^{22}$ which is attached to the ammonium nitrogen is a straight or branched alkyl group of four carbons or fewer.

In another embodiment, a composition is provided comprising a pharmaceutically acceptable carrier and a compound as described above.

In another embodiment, a method is provided for selectively modulating the function of a nicotinic acetylcholine receptor comprising administering a therapeutically effective amount of a compound as described above to a mammalian subject in need thereof.

In another embodiment, a method is provided for preventing and/or treating a central nervous system associated disorder, for example, schizophrenia, Tourettes', Huntington's Chorea, Parkinson's disease, Alzheimer's disease, and related conditions, comprising administering a therapeutically effective amount of a compound as described above to a mammalian subject in need thereof.

In another embodiment, a method is provided for preventing and/or treating substance use and/or abuse comprising administering a therapeutically effective amount of a compound as described above to a mammalian subject in need thereof.

In another embodiment, a method is provided for preventing and/or treating gastrointestinal tract disorders comprising administering a therapeutically effective amount of a compound as described above to a mammalian subject in need thereof.

Other methods, features and advantages of the present invention will be or become apparent to one with skill in the art upon examination of the following detailed descriptions. It is intended that all such additional methods, features and advantages be included within this description, be within the scope of the present invention, and be protected by the accompanying claims.

DETAILED DESCRIPTION OF INVENTION

Before the present compositions and methods are described, it is to be understood that the invention is not limited to the particular methodologies, protocols, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless the context clearly dictates otherwise.

Unless defined otherwise, all technical and scientific terms used herein have the same meanings as commonly understood by one of ordinary skill in the art to which this invention belongs. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The term "nicotinic acetylcholine receptor" refers to the endogenous acetylcholine receptor having binding sites for acetylcholine which also bind to S-nicotine. The term "nicotinic acetylcholine receptor" includes the term "neuronal nicotinic acetylcholine receptor."

The terms "subtype of nicotinic acetylcholine receptor," and "nicotinic acetylcholine receptor subtype" refer to various subunit combinations of the nicotinic acetylcholine receptor, and may refer to a particular homomeric or heteromeric complex, or multiple homomeric or heteromeric complexes.

The term "agonist" refers to a substance which interacts with a receptor and increases or prolongs a physiological response (i.e. activates the receptor).

The term "partial agonist" refers to a substance which interacts with and activates a receptor to a lesser degree than an agonist.

The term "antagonist" refers to a substance which interacts with and decreases the extent or duration of a physiological response of that receptor.

The terms "disorder," "disease," and "condition" are used inclusively and refer to any status deviating from normal.

The term "central nervous system associated disorders" includes any cognitive, neurological, and mental disorders causing aberrant or pathological neural signal transmission, such as disorders associated with the alteration of normal neurotransmitter release in the brain.

The term "lower alkyl" refers to straight or branched chain alkyl radicals having in the range of 1 to 4 carbon atoms.

The term "alkyl" refers to straight or branched chain alkyl radicals having 1 to 19 carbon atoms, and "substituted alkyl" refers to alkyl radicals further bearing one or more substituents including, but not limited to, hydroxy, alkoxy (of a lower alkyl group), mercapto (of a lower alkyl group), aryl, heterocyclic, halogen, trifluoromethyl, cyano, nitro, amino, carboxyl, carbarnate, sulfonyl, and sulfonamide.

The term "cycloalkyl" refers to cyclic ring-containing moieties containing 3 to 8 carbon atoms, and "substituted cycloalkyl" refers to cycloalkyl moieties further bearing one or more substituents as set forth above.

The term "alkenyl" refers to straight or branched chain hydrocarbyl groups having at least one carbon-carbon double bond and having 2 to 19 carbon atoms, and "substituted alkenyl" refers to alkenyl groups further bearing-one or more substituents as set forth above.

The term "alkynyl" refers to straight or branched chain hydrocarbyl moieties having at least one carbon-carbon triple bond and having 2 to 19 carbon atoms, and "substituted alkynyl" refers to alkynyl moieties further bearing one or more substituents as set forth above.

The term "aryl" refers to aromatic groups having 6 to 24 carbon atoms, and "substituted aryl" refers to aryl groups further bearing one or more substituents as set forth above.

The term "alkylaryl" refers to alkyl-substituted aryl groups, and "substituted alkylaryl" refers to alkylaryl groups further bearing one or more substituents as set forth above.

The term "arylalkyl" refers to aryl-substituted alkyl groups, and "substituted arylalkyl" refers to arylalkyl groups further bearing one or more substituents as set forth above.

The term "arylalkenyl" refers to aryl-substituted alkenyl groups, and "substituted arylalkenyl" refers to arylalkenyl groups further bearing one or more substituents as set forth above.

The term "arylalkynyl" refers to aryl-substituted alkynyl groups, and "substituted arylalkynyl" refers to arylalkynyl groups further bearing one or more substituents as set forth above.

The term "heterocyclic" refers to cyclic moieties containing one or more heteroatoms as part of the ring structure and having 3 to 24 carbon atoms, and "substituted heterocyclic" refers to heterocyclic moieties further bearing one or more substituents as set forth above.

The term "acyl" refers to alkyl-carbonyl groups, and "substituted acyl" refers to acyl groups further bearing one or more substituents as set forth above.

The term "halogen" refers to fluoride, chloride, bromide or iodide groups.

It is understood that in all substituted groups defined above, polymers arrived at by defining substituents with further substituents to themselves (e.g. substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Compounds of the present invention are bis-quaternary ammonium salts corresponding to Formula (I):

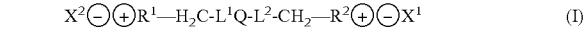

(I)

$X^{1\ominus}$ and $X^{2\ominus}$ are each independently an organic or inorganic anion.

Q is selected from phenylene, biphenylene, —CH=CH—, —CH=CH—CH=CH—, —C≡C—, —C≡C—C≡C—, —O—(CH$_2$)$_2$—O—, and —O—CH$_2$)$_2$—O(CH$_2$)$_2$—O—.

$L^1$ and $L^2$ are each independently selected from alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic; $SOY^1$, $SO_2Y^1$, $SO_2OY^1$ or $SO_2NHY^1$, where $Y^1$ is selected from hydrogen, lower alkyl, alkenyl, alkynyl or aryl, and where $Y^1$ is not hydrogen in $SOY^1$ and if $Y^1$ is alkenyl or alkynyl, the site of unsaturation is not conjugated with a heteroatom; $COY^2$, where $Y^2$ is selected from hydrogen, alkyl, substituted alkyl, cycloalkyl, substituted cycloalkyl, alkoxy, alkenyl, substituted alkenyl, alkynyl, substituted alkynyl, aryl, substituted aryl, aryloxy, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^2$ comprises alkenyl or alkynyl, the site of unsaturation is not conjugated with the carbonyl group; $OY^3$, where $Y^3$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, alkylsulfonyl, arylsulfonyl, heterocyclic, or substituted heterocyclic, where if $Y^3$ comprises alkenyl or alkynyl, the site of unsaturation is not conjugated with the oxygen; $NY^4Y^5$, where $Y^4$ and $Y^5$ are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, alkylsulfonyl, arylsulfonyl, heterocyclic, or substituted heterocyclic, where if $Y^4$ or $Y^5$ comprises alkenyl or alkynyl, the site of unsaturation is not conjugated with the nitrogen; $SY^6$, where $Y^6$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^6$ comprises alkenyl or alkynyl, the site of unsaturation is not conjugated with the sulfur.

$R^1$ and $R^2$ are each independently five or six membered nitrogen containing rings as shown in formulas (IIA) and (IIB).

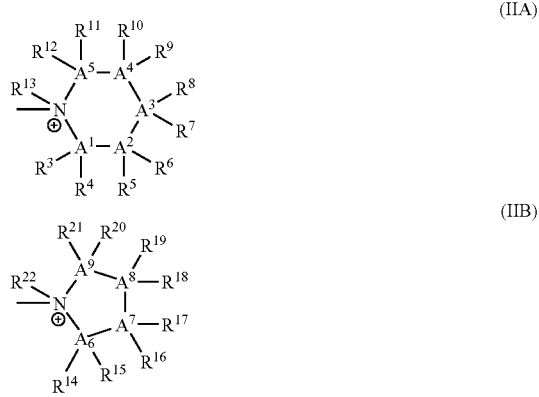

$A^1$ is carbon, nitrogen, sulfur or oxygen, provided that when $A^1$ is a carbon and joins a ring atom with an unsaturated bond or is a nitrogen, $R^3$ is absent, and when $A^1$ is sulfur or oxygen or joins a ring atom with an unsaturated bond and is a nitrogen, both $R^3$ and $R^4$ are absent.

$A^2$ is carbon, nitrogen, sulfur or oxygen, provided that when $A^2$ is a carbon and joins a ring atom with an unsaturated bond or is a nitrogen, $R^5$ is absent, and when $A^2$ is sulfur or oxygen or joins a ring atom with an unsaturated bond and is a nitrogen, both $R^5$ and $R^6$ are absent.

$A^3$ is carbon, nitrogen, sulfur or oxygen, provided that when $A^3$ is a carbon and joins a ring atom with an unsaturated bond or is a nitrogen, $R^7$ is absent, and when $A^3$ is sulfur or oxygen or joins a ring atom with an unsaturated bond and is a nitrogen, both $R^7$ and $R^8$ are absent.

$A^4$ is carbon, nitrogen, sulfur or oxygen, provided that when $A^4$ is a carbon and joins a ring atom with an unsaturated bond or is a nitrogen, $R^9$ is absent, and when $A^4$ is sulfur or oxygen or joins a ring atom with an unsaturated bond and is a nitrogen, both $R^9$ and $R^{10}$ are absent.

$A^5$ is carbon, nitrogen, sulfur or oxygen, provided that when $A^5$ is a carbon and joins a ring atom with an unsaturated bond or is a nitrogen, $R^{11}$ is absent, and when $A^5$ is sulfur or oxygen or joins a ring atom with an unsaturated bond and is a nitrogen, both $R^{11}$ and $R^{12}$ are absent.

$A^6$ is carbon, nitrogen, sulfur or oxygen, provided that when $A^6$ is a carbon and joins a ring atom with an unsaturated bond or is a nitrogen, $R^{14}$ is absent, and when $A^6$ is sulfur or oxygen or joins a ring atom with an unsaturated bond and is a nitrogen, both $R^{14}$ and $R^{15}$ are absent.

$A^7$ is carbon, nitrogen, sulfur or oxygen, provided that when $A^7$ is a carbon and joins a ring atom with an unsaturated bond or is a nitrogen, $R^{16}$ is absent, and when $A^7$ is sulfur or oxygen or joins a ring atom with an unsaturated bond and is a nitrogen, both $R^{16}$ and $R^{17}$ are absent.

$A^8$ is carbon, nitrogen, sulfur or oxygen, provided that when $A^8$ is a carbon and joins a ring atom with an unsaturated bond or is a nitrogen, $R^{18}$ is absent, and when $A^8$ is sulfur or oxygen or joins a ring atom with an unsaturated bond and is a nitrogen, both $R^{18}$ and $R^{19}$ are absent.

$A^9$ is carbon, nitrogen, sulfur or oxygen, provided that when $A^9$ is a carbon and joins a ring atom with an unsaturated bond or is a nitrogen, $R^{20}$ is absent, and when $A^9$ is sulfur or oxygen or joins a ring atom with an unsaturated bond and is a nitrogen, both $R^{20}$ and $R^{21}$ are absent.

$R^{13}$ or $R^{22}$ is absent when any of the bonds to the ammonium nitrogen is unsaturated, and $R^{13}$ or $R^{22}$ is a straight chain or branched alkyl group of four carbons or fewer when all of the bonds to the ammonium nitrogen are saturated.

$R^3$, $R^4$, $R^5$, $R^6$, $R^7$, $R^8$, $R^9$, $R^{10}$, $R^{11}$, and $R^{12}$, or $R^{14}$, $R^{15}$, $R^{16}$, $R^{17}$, $R^{18}$, $R^{19}$, $R^{20}$, and $R^{21}$, when present, are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, halo, cyano, nitro, or $R^4$ and $R^5$ together with $A^1$ and $A^2$, or $R^5$ and $R^7$ together with $A^2$ and $A^3$, or $R^{15}$ and $R^{16}$ together with $A^6$ and $A^7$, or $R^{16}$ and $R^{18}$ together with $A^7$ and $A^8$ independently form a three to eight member cyclolkane, substituted cycloalkane, cycloalkene, substituted cycloalkene, aryl, substituted aryl, heterocycle with one to three hetero atoms of nitrogen, oxygen or sulfur in the ring, or substituted heterocycle with one to three hetero atoms of nitrogen, oxygen or sulfur in the ring; and when all of the bonds to the ring ammonium nitrogen are saturated, then any of $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ or $R^{22}$ which is attached to the ammonium nitrogen is a straight or branched alkyl group of four carbons or fewer.

For example, $R^1$ and $R^2$ include pyrrole, pyrrolidine, pyrazole, imidazole, oxazole, isoxazole, thiazole, isothiazole, oxadiazole, oxatriazole, dioxazole, 1,2,3-triazole, 1,2,4-triazole, pyridine, pyrimidine, piperidine, quinoline, tetrahydroquinoline, isoquinoline, tetrahydroisoquinoline, pyrazine, piperazine, pyridazine, triazine, oxazine, phenazine, pteridine, benzoxazine, phthalazine, naphthridine, quinoxaline, quinazoline, cinnoline, quinuclidine, benzothiazole, benzisoxazole, benzoxazole, indazole, pyranopyrrole, cyclopentapyridine, benzimidazole, isoindole, 3H-indole, indolene and triazine.

As another example, $R^3$, $R^4$, $R^5$, $R^6$, $R^7$, $R^8$, $R^9$, $R^{10}$, $R^{11}$, $R^{12}$, $R^{14}$, $R^{15}$, $R^{16}$, $R^{17}$, $R^{18}$, $R^{19}$, $R^{20}$, and $R^{21}$, include hydrogen, methyl, ethyl, propyl, butyl, hydroxymethyl, hydroxyethyl, hydroxypropyl, trifluoromethyl, chloro, bromo, phenyl, pyrrolidine, N-alkyl pyrrolidine (for example where the alkyl chain is methyl, ethyl or propyl), unsaturated pyrrolidine, unsaturated N-alkyl pyrrolidine (for example where the alkyl chain is methyl, ethyl or propyl), aziridine, N-methyl aziridine, azetidine, N-methyl azetidine, unsaturated azetidine, unsaturated N-methyl azetidine, piperidine, N-methyl piperidine, unsaturated piperidine, unsaturated N-methyl piperidine, azepane, N-methyl azepane, unsaturated azepane, unsaturated N-methyl azepane, azocane, N-methyl azocane, unsaturated azocane, unsaturated N-methyl azocane, 1-aza-bicyclo[3.2.1]octane, 1-aza-bicyclo[2.2.1]heptane, 8-methyl-8-aza-bicyclo[3.2.1]octane, 1-aza-tricyclo [3.3.1.1$^{3,7}$]decane, methyl cycloalkyl, methyl substituted cycloalkyl, methyl pyrrolidine, methyl N-alkyl pyrrolidine (for example where the alkyl chain is methyl, ethyl or propyl), methyl unsaturated pyrrolidine, methyl unsaturated N-alkyl pyrrolidine (for example where the alkyl chain is methyl, ethyl or propyl), methyl aziridine, methyl N-methyl aziridine, methyl azetidine, methyl N-methyl azetidine, methyl unsaturated azetidine, methyl unsaturated N-methyl azetidine, methyl piperidine, methyl N-methyl piperidine, methyl unsaturated piperidine, methyl unsaturated N-methyl piperidine, methyl azepane, methyl N-methyl azepane, methyl unsaturated azepane, methyl unsaturated N-methyl azepane, methyl azocane, methyl N-methyl azocane, methyl unsaturated azocane, methyl unsaturated N-methyl azocane, methyl-1-aza-bicyclo[3.2.1]octane, methyl-1-aza-bicyclo[2.2.1]heptane, 8-methyl-8-aza-bicyclo[3.2.1]octane, and methyl-1-aza-tricyclo[3.3.1.1$^{3,7}$]decane.

As a further example, when $R^4$ and $R^5$ together with $A^1$ and $A^2$, or $R^5$ and $R^7$ together with $A^2$ and $A^3$, or $R^{15}$ and $R^{16}$ together with $A^6$ and $A^7$, or $R^{16}$ and $R^{18}$ together with $A^7$ and $A^8$ independently form a three to eight-membered ring, that ring may be a heterocycle containing up to three hetero atoms (for example nitrogen, oxygen or sulfur) in the ring, and further may be substituted with one or more substituents. For example, possible rings include benzene, pyridine, pyran, indene, isoindene, benzofuran, isobenzofuran, benzo[b]thiophene, benzo[c]thiophene, indole, indolenine, isoindole, cyclopental[b]pyridine, pyrano[3,4-b]pynrole, indazole, indoxazine, benzoxazole, anthranil, naphthalene, tetralin, decalin, chromene, coumarin, chroman-4-one, isocoumarin, isochromen-3-one, quinoline, isoquinoline, cinnoline, quinazoline, naphthyrdine, pyrido[3,4-b]-pyridine, pyridol[3,2-b]pyridine, pyrido[4,3,-b]-pyridine, benzoxazine, anthracene, phenanthrene, phenalene, fluorene, carazole, xanthene, acnidine, octahydro-[1]pyridine, 1-methyloctahydro-[1]pyridine, octahydroindole, 1-methyloctahydro-indole, octahydro-cyclopenta[b]pyrrole, 1-methyloctahydro-cyclopenta[b]pyrrole, decahydroquinoline, and 1-methyldecahydroquinoline.

$X^{1\ominus}$ and $X^{2\ominus}$, for example, include F$^-$, Cl$^-$, Br$^-$, I$^-$, NO$_2^-$, HSO$_4^-$, SO$_4^-$, HPO$_4^-$, PO$_4^{2-}$, methanesulfonate, trifluoromethane sulfate, p-toluenesulfonate, benzenesulfonate, salicylate, proprionate, ascorbate, aspartate, fumarate, galactarate, maleate, citrate, glutamate, glycolate, lactate, malate, maleate, tartrate, oxalate, succinate, or similar pharmaceutically acceptable organic acid addition salts, including the pharmaceutically acceptable salts listed in the Journal of Pharmaceutical Sciences volume 66, page 2, 1977, which are hereby incorporated by reference. The above salt forms may be in some cases hydrates or solvates with alcohols and other solvents.

In a compound of Formula (I), preferably $R^1$ and $R^2$ are substituted, six-membered, aromatic rings. More preferably, $R^1$ and $R^2$ are substituted pyridinium rings. In other preferred embodiments, $R^1$ and $R^2$ are quinoline, isoquinoline, tetrahydroquinoline or tetrahydroisoquinoline.

In a compound of Formula (I), preferably $R^{13}$ is absent.

In a compound of Formula (I), preferably $R^3$, $R^4$, $R^5$, $R^6$, $R^7$, $R^8$, $R^9$, $R^{10}$, $R^{11}$ or $R^{12}$ is absent or is hydrogen, alkyl, hydroxyalkyl, halo, phenyl or 1-alkyl-2-pyrrolidinyl. More preferably, $R^3$, $R^4$, $R^5$, $R^6$, $R^7$, $R^8$, $R^9$, $R^{10}$, $R^{11}$ or $R^{12}$ is absent or is hydrogen, methyl, ethyl, propyl, butyl, hydroxymethyl, hydroxyethyl, hydroxypropyl, bromo, phenyl or 1-methyl-2-pyrrolidinyl.

In a compound of Formula (I), preferably Q is phenylene, biphenylene, —CH═CH—CH═CH—, —C≡C—C≡C— and —O—(CH$_2$)$_2$—O—(CH$_2$)$_2$—O—.

In a compound of Formula (I), preferably $L^1$ and $L^2$ are the same and are —CH$_2$—, —(CH$_2$)$_2$—, —(CH$_2$)$_3$—, —(CH$_2$)$_4$—, —C≡C—, —CH$_2$—C≡C— or —(CH$_2$)$_2$—C≡C—.

In a compound of Formula (I), preferably $X^{1\ominus}$ and $X^{2\ominus}$ are halogens. More preferably, $X^{1\ominus}$ and $X^{2\ominus}$ are chloride or bromide.

In another embodiment, the compound of Formula (I) is defined wherein -L$_1$-Q-L$_2$- is —(CH$_2$)$_4$-1,2-phenylene-(CH$_2$)$_4$—, —(CH$_2$)$_4$-1,3-phenylene-(CH$_2$)$_4$—, —(CH$_2$)$_3$-1,4-phenylene-(CH$_2$)$_3$—, —(CH$_2$)$_2$-4,4'-biphenylene-(CH$_2$)$_2$—, —(CH$_2$)$_2$—C≡C-1,2-phenylene-C≡C—(CH$_2$)$_2$—, —(CH$_2$)$_2$—C≡C-1,3-phenylene-C≡C—(CH$_2$)$_2$—, —CH$_2$—C≡C-1,4-phenylene-C≡C—CH$_2$—, —C≡C-4,4'-biphenylene-C≡C—, —(CH$_2$)$_3$—CH═CH—CH═CH—(CH$_2$)$_3$—, —(CH$_2$)$_3$—C≡C—C≡C—(CH$_2$)$_3$— or —CH$_2$—O—(CH$_2$)$_2$—O—(CH$_2$)$_2$—O—CH$_2$—, $R^1$ and $R^2$ are pyridinium rings, $R^3$ is hydrogen or methyl, $R^5$ is hydrogen, methyl, ethyl, butyl, phenyl, 1-methyl-2-pyrrolidinyl, bromo, hydroxymethyl or hydroxypropyl, $R^7$ is hydrogen or methyl, $R^9$ is hydrogen or methyl, $R^{11}$ is hydrogen, and $X^1$ and $X^2$ are chloride or bromide.

In another embodiment, the compound of Formula (I) is defined wherein -L$_1$-Q-L$_2$- is —(CH$_2$)$_4$-1,2-phenylene-(CH$_2$)$_4$—, —(CH$_2$)$_4$-1,3-phenylene-(CH$_2$)$_4$—, —(CH$_2$)$_3$-1,4-phenylene-(CH$_2$)$_3$—, —(CH$_2$)$_2$-4,4'-biphenylene-(CH$_2$)$_2$—, —(CH$_2$)$_2$—C≡C-1,2-phenylene-C≡C—(CH$_2$)$_2$—, —(CH$_2$)$_2$—C≡C-1,3-phenylene-C≡C—(CH$_2$)$_2$—, —CH$_2$—C≡C-1,4-phenylene-C≡CH$_2$—, —C≡C-4,4'-biphenylene-C≡C—, —(CH$_2$)$_3$—CH═CH—CH═CH—(CH$_2$)$_3$—, —(CH$_2$)$_3$—C≡C—C≡C—(CH$_2$)$_3$— or —CH$_2$—O—(CH$_2$)$_2$—O—(CH$_2$)$_2$—O—CH$_2$—, $R^1$ and $R^2$ are quinoline, isoquinoline, tetrahydroquinoline or tetrahydroisoquinoline, and $X^1$ and $X^2$ are chloride or bromide.

Exemplary compounds of the present invention include:
cis-cis-N,N'-(dodeca-5,7-diene-1,12-diyl)-bis-[3-(2'-S-1-methyl-pyrrolidin-2-yl)-pyridinium]dibromide;
cis-cis-N,N'-(dodeca-5,7-diene-1,12-diyl)-bis-(2-methyl-pyridinium)dibromide;
cis-cis-N,N'-(dodeca-5,7-diene-1,12-diyl)-bis-(3-methyl-pyridinium)dibromide;
cis-cis-N,N'-(dodeca-5,7-diene-1,12-diyl)-bis-(4-methyl-pyridinium)dibromide;
cis-cis-N,N'-(dodeca-5,7-diene-1,12-diyl)-bis-(5,6,7,8-tetrahydro-quinolinium)dibromide;
cis-cis-N,N'-(dodeca-5,7-diene-1,12-diyl)-bis-(5,6,7,8-tetrahydro-isoquinolinium)dibromide;
cis-cis-N,N'-(dodeca-5,7-diene-1,12-diyl)-bis-(2,4-dimethyl-pyridinium)dibromide;
cis-cis-N,N'-(dodeca-5,7-diene-1,12-diyl)-bis-(3,4-dimethyl-pyridinium)dibromide;
cis-cis-N,N'-(dodeca-5,7-diene-1,12-diyl)-bis-(3,5-dimethyl-pyridinium)dibromide;
N,N'-[1,4-phenylenedi-(4-butanyl)]-bis-[3-(2'-S-1-methyl-pyrrolidin-2-yl)-pyridinium]dibromide;
N,N'-[1,4-phenylenedi-(4-butanyl)]-bis-(2-methylpyridinium)dibromide;

N,N'-[1,4-phenylenedi-(4-butanyl)]-bis-(3-methylpyridinium)dibromide;
N,N'-[1,4-phenylenedi-(4-butanyl)]-bis-(4-methylpyridinium)dibromide;
N,N'-[1,4-phenylenedi-(4-butanyl)]-bis-(3-ethylpyridinium)dibromide;
N,N'-[1,4-phenylenedi-(4-butanyl)]-bis-(5,6,7,8-tetrahydroquinolinium)dibromide;
N,N'-[1,4-phenylenedi-(4-butanyl)]-bis-(5,6,7,8-tetrahydroisoquinolinium)dibromide;
N,N'-[1,4-phenylenedi-(4-butanyl)]-bis-[3-(3-hydroxy-propyl)-pyridinium]dibromide;
N,N'-[1,4-phenylenedi-(4-butanyl)]-bis-(2,4-dimethylpyridinium)dibromide;
N,N'-[1,4-phenylenedi-(4-butanyl)]-bis-(3,4-dimethylpyridinium)dibromide;
N,N'-[1,4-phenylenedi-(4-butanyl)]-bis-(3,5-dimethylpyridinium)dibromide;
1,2-bis-[5-(2-methyl-pyridinium)-pent-1-ynyl]-benzene dibromide;
1,2-bis-[5-(3-methyl-pyridinium)-pent-1-ynyl]-benzene dibromide;
1,2-bis-[5-(4-methyl-pyridinium)-pent-1-ynyl]-benzene dibromide;
1,2-bis-[5-(2,4-dimethyl-pyridinium)-pent-1-ynyl]-benzene dibromide;
1,2-bis-[5-(3,4-dimethyl-pyridinium)-pent-1-ynyl]-benzene dibromide;
1,2-bis-[5-(3,5-dimethyl-pyridinium)-pent-1-ynyl]-benzene dibromide;
1,2-bis-(5-quinolinium-pent-1-ynyl)-benzene dibromide;
1,2-bis-(5-isoquinolinium-pent-1-ynyl)-benzene dibromide;
1,2-bis-(5-S-nicotinium-pent-1-ynyl)-benzene dibromide;
1,2-bis-[5-(2-methyl-pyridinium)-pentyl]-benzene dibromide;
1,2-bis-[5-(3-methyl-pyridinium)-pentyl]-benzene dibromide;
1,2-bis-[5-(4-methyl-pyridinium)-pentyl]-benzene dibromide;
1,2-bis-[5-(2,4-dimethyl-pyridinium)-pentyl]-benzene dibromide;
1,2-bis-[5-(3,4-dimethyl-pyridinium)-pentyl]-benzene dibromide;
1,2-bis-[5-(3,5-methyl-pyridinium)-pentyl]-benzene dibromide;
1,2-bis-(5-quinolinium-pentyl)-benzene dibromide;
1,2-bis-(5-isoquinolinium-pentyl)-benzene dibromide;
1,2-bis-(5-S-nicotinium-pentyl)-benzene dibromide;
1,2-bis-[5-(3-n-butyl-pyridinium)-pentyl]-benzene dibromide;
1,2-bis-[5-(3-bromo-pyridinium)-pentyl]-benzene dibromide;
1,2-bis-(5-pyridinium-pentyl)-benzene dibromide;
1,3-bis-[5-(2-methyl-pyridinium)-pent-1-ynyl]-benzene dibromide;
1,3-bis-[5-(3-methyl-pyridinium)-pent-1-ynyl]-benzene dibromide;
1,3-bis-[5-(4-methyl-pyridinium)-pent-1-ynyl]-benzene dibromide;
1,3-bis-[5-(2,4-dimethyl-pyridinium)-pent-1-ynyl]-benzene dibromide;
1,3-bis-[5-(3,4-dimethyl-pyridinium)-pent-1-ynyl]-benzene dibromide;
1,3-bis-[5-(3,5-dimethyl-pyridinium)-pent-1-ynyl]-benzene dibromide;
1,3-bis-(5-quinolinium-pent-1-ynyl)-benzene dibromide;
1,3-bis-(5-isoquinolinium-pent-1-ynyl)-benzene dibromide;
1,3-bis-(5-S-nicotinium-pent-1-ynyl)-benzene dibromide;
1,3-bis-[5-(3-n-butyl-pyridinium)-pent-1-ynyl]-benzene dibromide;
1,3 bis-[5-(3-phenyl-pyridinium)-pent-1-ynyl]-benzene dibromide;
1,3-bis-(5-pyridinium-pent-1-ynyl)-benzene dibromide;
1,3-bis-[5-(2-methyl-pyridinium)-pentyl]-benzene dibromide;
1,3-bis-[5-(3-methyl-pyridinium)-pentyl]-benzene dibromide;
1,3-bis-[5-(4-methyl-pyridinium)-pentyl]-benzene dibromide;
1,3-bis-[5-(2,4-dimethyl-pyridinium)-pentyl]-benzene dibromide;
1,3-bis-[5-(3,4-dimethyl-pyridinium)-pentyl]-benzene dibromide;
1,3-bis-[5-(3,5-dimethyl-pyridinium)-pentyl]-benzene dibromide;
1,3-bis-(5-quinolinium-pentyl)-benzene dibromide;
1,3-bis-(5-isoquinolinium-pentyl)-benzene dibromide;
N,N'-[(1,1'-biphenyl)-4,4'-di-(3-propanyl)]-bis-[3-(2'-S-1-methyl-pyrrolidin-2-yl)-pyridinium]dibromide;
N,N'-[(1,1'-biphenyl)-4,4'-di-(3-propanyl)]-bis-(3,5-dimethylpyridinium)dibromide;
N,N'-[(1,1'-biphenyl)-4,4'-di-(3-propanyl)]-bis-(3,4-dimethylpyridinium)dibromide;
N,N'-[(1,1'-biphenyl)-4,4'-di-(3-propanyl)]-bis-(2,4-dimethylpyridinium)dibromide;
N,N'-[(1,1'-biphenyl)-4,4'-di-(3-propanyl)]-bis-[3-(3-hydroxy-propyl)-pyridinium]dibromide;
N,N'-[(1,1'-biphenyl)-4,4'-di-(3-propanyl)]-bis-[5,6,7,8-tetrahydroquinolinium]dibromide;
N,N'-[(1,1'-biphenyl)-4,4'-di-(3-propanyl)]-bis-[5,6,7,8-tetrahydroisoquinolinium]dibromide;
N,N'-[(1,1'-biphenyl)-4,4'-di-(3-propanyl)]-bis-(4-methylpyridinium)dibromide;
N,N'-[(1,1'-biphenyl)-4,4'-di-(3-propanyl)]-bis-(3-methylpyridinium)dibromide;
N,N'-[(1,1'-biphenyl)-4,4'-di-(3-propanyl)]-bis-(2-methylpyridinium)dibromide;
N,N'-{2,2'-[oxybis(2,1-ethandiyloxy)]bis-ethyl}-bis-[3-(2'-S-1-methyl-pyrrolidin-2-yl)-pyridinium]dichloride;
N,N'-{2,2'-[oxybis(2,1-ethandiyloxy)]bis-ethyl}-bis(2-methylpyridinium)dichloride;
N,N'-{2,2'-[oxybis(2,1-ethandiyloxy)]bis-ethyl}-bis(3-methylpyridinium)dichloride;
N,N'-{2,2'-[oxybis(2,1-ethandiyloxy)]bis-ethyl}-bis(4-methylpyridinium)dichloride;
N,N'-{2,2'-[oxybis(2,1-ethandiyloxy)]bis-ethyl}-bis(5,6,7,8-tetrahydroquinolinium)dichloride;
N,N'-{2,2'-[oxybis(2,1-ethandiyloxy)]bis-ethyl}-bis(5,6,7,8-tetrahydroisoquinolinium)dichloride;
N,N'-{2,2'-[oxybis(2,1-ethandiyloxy)]bis-ethyl}-bis-[3-(3-hydroxypropyl)-pyridinium]dichloride;
N,N'-{2,2'-[oxybis(2,1-ethandiyloxy)]bis-ethyl}-bis-(3-hydroxymethylpyridinium)dichloride;
N,N'-{2,2'-[oxybis(2,1-ethandiyloxy)]bis-ethyl}-bis-(2,4-dimethylpyridinium)dichloride;
N,N'-{2,2'-[oxybis(2,1-ethandiyloxy)]bis-ethyl}-bis-(3,4-dimethylpyridinium)dichloride;
N,N'-{2,2'-[oxybis(2,1-ethandiyloxy)]bis-ethyl}-bis-(3,5-dimethylpyridinium)dichloride;
N,N'-(5,7-dodecadiyn-1,12-diyl)-bis-(2-methylpyridinium) dichloride;
N,N'-(5,7-dodecadiyn-1,12-diyl)-bis-(3-methylpyridinium) dichloride;

N,N'-(5,7-dodecadiyn-1,12-diyl)-bis-(4-methylpyridinium) dichloride;
N,N'-(5,7-dodecadiyn-1,12-diyl)-bis-(3,4-dimethylpyridinium)dichloride;
N,N'-(5,7-dodecadiyn-1,12-diyl)-bis-(3,5-dimethylpyridinium)dichloride;
N,N'-(5,7-dodecadiyn-1,12-diyl)-bis-(5,6,7,8-tetrahydroisoquinolinium)dichloride;
N,N'-[(1,4-phenylene)-bis-(4-butynyl)]-bis-(3-methyl-pyridinium)dibromide;
N,N'-[(1,4-phenylene)-bis-(4-butynyl)]-bis-(4-methyl-pyridinium)dibromide;
N,N'-[(1,4-phenylene)-bis-(4-butynyl)]-bis-(5,6,7,8-tetrahydroisoquiolinium)dibromide;
N,N'-[(1,4-phenylene)-bis-(4-butynyl)]-bis-(3,4-dimethylpyridinium)dibromide;
N,N'-[(1,4-phenylene)-bis-(4-butynyl)]-bis-(3,5-dimethylpyridinium)dibromide;
N,N'-[(1,1'-biphenyl)-4,4'-di-(1-propyn-3-yl)]-bis-(3-methylpyridinium)dibromide;
N,N'-[(1,1'-biphenyl)-4,4'-di-(1-propyn-3-yl)]-bis-(4-methylpyridinium)dibromide;
N,N'-[(1,1'-biphenyl)-4,4'-di-(1-propyn-3-yl)]-bis-(3,4-dimethylpyridinium)dibromide.

The compounds of the present invention may contain one or more stereocenters. The invention includes all possible diastereomers and all enantiomeric forms as well as all combinations of diastereomers and enantiomers, including racemic mixtures. The compounds can be separated into substantially optically pure compounds.

The compounds of the invention are nicotinic acetylcholine receptor agents. Thus, they may augment or inhibit [$^3$H]—S-nicotine binding, [$^3$H]MLA binding, evoke or inhibit neurotransmitter release, and/or evoke or inhibit the flux of ions through the nicotinic receptor. Moreover, the compounds of the invention may act either at presynaptic sites or postsynaptic sites, for example, at a postsynaptic acetylcholine receptor containing an $\alpha 7$ subunit. When acting at a postsynaptic site, neurotransmitter release per se is not altered. Rather, the compounds of the invention may act by interacting with a postsynaptic acetylcholine receptor to change the membrane potential of the cell, thereby increasing or decreasing the likelihood of firing an action potential. Alternatively, interaction of a compound of the invention with a postsynaptic acetylcholine receptor may result in the alteration of one or more second messenger systems within the cell so as to decrease or increase the nicotinic cholinergic response.

In one embodiment, the present invention relates to a method for selectively modulating the function of a nicotinic acetylcholine receptor comprising administering to a mammalian subject in need thereof a therapeutically effective amount of a compound of Formula (I). In such a method, the compound of Formula (I) may selectively bind to one or more subtypes of nicotinic acetylcholine receptor. The compound of Formula (I) may act as an agonist or partial agonist of nicotinic acetylcholine receptor function. Hence the compound of Formula (I) may increase or prolong the release of a neurotransmitter from a central nervous system tissue. The neurotransmitter affected may include dopamine, norepinephrine, serotonin, gamma-aminobutryic acid, or glutamate. Alternatively, the compound of Formula (I) may act as an antagonist of nicotinic acetylcholine receptor function. Hence the compound of Formula (I) may decrease the extent or duration of the release of a neurotransmitter from a central nervous system tissue. In this regard, the compound of Formula (I) may act by decreasing stimulant-evoked neurotransmitter release. The neurotransmitter affected may include dopamine, norepinephrine, serotonin, gamma-aminobutryic acid, or glutamate. Alternatively, the compound of Formula (I) may act by interacting with a postsynaptic acetylcholine receptor to change the membrane potential of the cell thereby increasing or decreasing the likelihood of firing an action potential, or to alter one or more second messenger systems within the cell so as to decrease or increase the nicotinic cholinergic response.

In another embodiment, the present invention is directed to a method for preventing and/or treating a central nervous system associated disorder comprising administering to a mammalian subject in need thereof a therapeutically effective amount of a compound of Formula (I). In such a method, the compound of Formula (I) may selectively bind to one or more subtypes of nicotinic acetylcholine receptor. The compound of Formula (I) may act as an agonist or partial agonist of nicotinic acetylcholine receptor function. Hence the compound of Formula (I) may increase or prolong the release of a neurotransmitter from a central nervous system tissue. The neurotransmitter affected may include dopamine, norepinephrine, serotonin, gamma-aminobutryic acid, or glutamate. Alternatively, the compound of Formula (I) may act as an antagonist of nicotinic acetylcholine receptor function. Hence the compound of Formula (I) may decrease the extent or duration of the release of a neurotransmitter from a central nervous system tissue. In this regard, the compound of Formula (I) may act by decreasing stimulant-evoked neurotransmitter release. The neurotransmitter affected may include dopamine, norepinephrine, serotonin, gamma-aminobutryic acid, or glutamate. Alternatively, the compound of Formula (I) may act by interacting with a postsynaptic acetylcholine receptor to change the membrane potential of the cell thereby increasing or decreasing the likelihood of firing an action potential, or to alter one or more second messenger systems within the cell so as to decrease or increase the nicotinic cholinergic response.

Central nervous system disorders which may be treated according to the method of the present invention include Alzheimer's disease, dementia, cognitive dysfunctions (including disorders of attention, focus and concentration), attention deficit disorders, affective disorders, extrapyramidal motor function disorders, Parkinson's disease, progressive supramolecular palsy, Huntington's disease, Gilles de la Tourette syndrome, tardive dyskinesia, neuroendocrine disorders, dysregulation of food intake, disorders of nociception, pain, mood and emotional disorders, depression, panic anxiety, psychosis, schizophrenia, or epilepsy.

In yet another embodiment, the present invention is directed to a method for preventing and/or treating substance use and/or abuse comprising administering to a mammalian subject in need thereof a therapeutically effective amount of a compound of Formula (I). In such a method, the compound of Formula (I) may selectively bind to one or more subtypes of nicotinic acetylcholine receptor. The compound of Formula (I) may act as an agonist or partial agonist of nicotinic acetylcholine receptor function. Hence the compound of Formula (I) may increase or prolong the release of a neurotransmitter from a central nervous system tissue. The neurotransmitter affected may include dopamine, norepinephrine, serotonin, gamma-aminobutryic acid, or glutamate. Alternatively, the compound of Formula (I) may act as an antagonist of nicotinic acetylcholine receptor function. Hence the compound of Formula (I) may decrease the extent or duration of the release of a neurotransmitter from a central nervous system tissue. In this regard, the compound of Formula (I) may act by decreasing stimulant-evoked neurotransmitter release. The neurotransmitter affected may include dopamine, norepinephrine, serotonin, gamma-aminobutryic acid, or glutamate. Alternatively, the compound of Formula (I) may act by interacting with a postsynaptic acetylcholine receptor to change the membrane potential of the cell thereby increasing or decreasing the likelihood of firing an action potential, or to alter one or more second messenger systems within the cell so as to decrease or increase the nicotinic cholinergic response.

The conditions of substance use and/or abuse treated according to the method of the present invention include nicotine abuse (including use in smoking cessation therapy), nicotine intoxication, amphetamine abuse, methamphetamine abuse, MDMA (methylenedioxymethamphetamine) abuse, methylphenidate abuse, cocaine abuse, or alcohol abuse.

In another embodiment, the present invention is directed to a method for preventing and/or treating gastrointestinal tract disorders comprising administering to a mammalian subject in need thereof a therapeutically effective amount of a compound of Formula (I). In such a method, the compound of Formula (I) may selectively bind to one or more subtypes of nicotinic acetylcholine receptor. The compound of Formula (I) may act as an agonist or partial agonist of nicotinic acetylcholine receptor function. Hence the compound of Formula (I) may increase or prolong the release of a neurotransmitter from a central nervous system tissue, or may increase or prolong the release of a neurotransmitter from a peripheral nervous system tissue, or may act directly on a gastrointestinal tract tissue. The neurotransmitter affected may include dopamine, norepinephrine, serotonin, gamma-aminobutryic acid, or glutamate. Alternatively, the compound of Formula (I) may act as an antagonist of nicotinic acetylcholine receptor function. Hence the compound of Formula (I) may decrease the extent or duration of the release of a neurotransmitter from a central nervous system tissue, or may decrease the extent or duration of the release of a neurotransmitter from a peripheral nervous system tissue, or may act directly on a gastrointestinal tract tissue. In this regard, the compound of Formula (I) may act by decreasing stimulant-evoked neurotransmitter release. The neurotransmitter affected may include dopamine, norepinephrine, serotonin, gamma-aminobutryic acid, or glutamate. Alternatively, the compound of Formula (I) may act by interacting with a postsynaptic acetylcholine receptor to change the membrane potential of the cell thereby increasing or decreasing the likelihood of firing an action potential, or to alter one or more second messenger systems within the cell so as to decrease or increase the nicotinic cholinergic response.

Gastrointestinal disorders which may be treated according to the method of the present invention include irritable bowel syndrome, colitis, diarrhea, constipation, gastric acid secretion or ulcers.

In yet another embodiment, the present invention is directed to a method for preventing and/or treating inflammatory tract disorders comprising administering to a mammalian subject in need thereof a therapeutically effective amount of a compound of Formula (I). In such a method, the compound of Formula (I) may selectively bind to one or more subtypes of nicotinic acetylcholine receptor. The compound of Formula (I) may act as an agonist or partial agonist of nicotinic acetylcholine receptor function. Hence the compound of Formula (I) may increase or prolong the release of a neurotransmitter from a central nervous system tissue, or may increase or prolong the release of a neurotransmitter from a peripheral nervous system tissue, or may act directly on a non-nervous system tissue. The neurotransmitter affected may include dopamine, norepinephrine, serotonin, gamma-aminobutryic acid, or glutamate. Alternatively, the compound of Formula (I) may act as an antagonist of nicotinic acetylcholine receptor function. Hence the compound of Formula (I) may decrease the extent or duration of the release of a neurotransmitter from a central nervous system tissue, or may decrease the extent or duration of the release of a neurotransmitter from a peripheral nervous system tissue, or may act directly on a non-nervous system tissue. In this regard, the compound of Formula (I) may act by decreasing stimulant-evoked neurotransmitter release. The neurotransmitter affected may include dopamine, norepinephrine, serotonin, gamma-aminobutryic acid, or glutamate. Alternatively, the compound of Formula (I) may act by interacting with a postsynaptic acetylcholine receptor to change the membrane potential of the cell thereby increasing or decreasing the likelihood of firing an action potential, or to alter one or more second messenger systems within the cell so as to decrease or increase the nicotinic cholinergic response.

Inflammatory disorders which may be treated according to the method of the present invention include adult respiratory distress syndrome, allergy, anemia, ankylosing spondylitis, asthma, atherosclerosis, bacterial infections, benign prostatic hyperplasia, cholecystitis, ulcerative colitis, Crohn's disease, diabetes mellitus, emphysema, gastritis, glomerulonephritis, hypereosinophilia, irritable bowel syndrome, multiple sclerosis, osteoarthritis, pancreatitis, polymyositis, psoriasis and rheumatoid arthritis.

The compounds of the present invention can be delivered directly or in pharmaceutical compositions along with suitable carriers or excipients, as is well known in the art. For example, a pharmaceutical composition of the invention may include a conventional additive, such as a stabilizer, buffer, salt, preservative, filler, flavor enancer and the like, as known to those skilled in the art. Exemplary buffers include phosphates, carbonates, citrates and the like. Exemplary preservatives include EDTA, EGTA, BHA, BHT and the like.

An effective amount of such agents can readily be determined by routine experimentation, as can the most effective and convenient route of administration and the most appropriate formulation. Various formulations and drug delivery systems are available in the art. See, e.g., Gennaro, A. R., ed. (1995) Remington's Pharmaceutical Sciences.

Suitable routes of administration may, for example, include oral, rectal, transmucosal, nasal, or intestinal administration and parenteral delivery, including intramuscular, subcutaneous, intramedullary injections, as well as intrathecal, direct intraventricular, intravenous, intraperitoneal, intranasal, or intraocular injections. In addition, the agent or composition thereof may be administered sublingually or via a spray, including a sublingual tablet or a sublingual spray. The agent or composition thereof may be administered in a local rather than a systemic manner. For example, a suitable agent can be delivered via injection or in a targeted drug delivery system, such as a depot or sustained release formulation.

The pharmaceutical compositions of the present invention may be manufactured by any of the methods well-known in the art, such as by conventional mixing, dissolving, granulating, dragee-making, levigating, emulsifying, encapsulating, entrapping, or lyophilizing processes. As noted above, the compositions of the present invention can include one or more physiologically acceptable carriers such as excipients and auxiliaries that facilitate processing of active molecules into preparations for pharmaceutical use.

Proper formulation is dependent upon the route of administration chosen. For injection, for example, the composition may be formulated in aqueous solutions, preferably in physiologically compatible buffers such as Hanks' solution, Ringer's solution, or physiological saline buffer. For transmucosal or nasal administration, penetrants appropriate to the barrier to be permeated are used in the formulation. Such penetrants are generally known in the art. In a preferred embodiment of the present invention the present compounds are prepared in a formulation intended for oral administration. For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject. The compounds may also be formulated in rectal compositions such as suppositories or retention enemas, e.g., containing conventional suppository bases such as cocoa butter or other glycerides.

Pharmaceutical preparations for oral use can be obtained as solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Also, wetting agents such as sodium dodecyl sulfate may be included.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In one embodiment, the compounds of the present invention can be administered transdermally, such as through a skin patch, or topically. In one aspect, the transdermal or topical formulations of the present invention can additionally comprise one or multiple penetration enancers or other effectors, including agents that enhance migration of the delivered compound. Transdermal or topical administration could be preferred, for example, in situations in which location specific delivery is desired.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges of, for example, gelatin, for use in an inhaler or insufflator may be formulated. These typically contain a powder mix of the compound and a suitable powder base such as lactose or starch.

Compositions formulated for parenteral administration by injection, e.g., by bolus injection or continuous infusion can be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents. Formulations for parenteral administration include aqueous solutions or other compositions in water-soluble form.

Suspensions of the active compounds may also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Alternatively, the active ingredient may be in powder form for constitution with a suitable vehicle, e.g., sterile pyrogen-free water, before use.

As mentioned above, the compositions of the present invention may also be formulated as a depot preparation. Such long acting formulations may be administered by implantation (for example, subcutaneously or intramuscularly) or by intramuscular injection. Thus, for example, the present compounds may be formulated with suitable polymeric or hydrophobic materials (for example as an emulsion in an acceptable oil) or ion exchange resins, or as sparingly soluble derivatives, for example, as a sparingly soluble salt.

Suitable carriers for the hydrophobic molecules of the invention are well known in the art and include co-solvent systems comprising, for example, benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system is effective in dissolving hydrophobic compounds and produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic molecules may be employed. Liposomes and emulsions are well known examples of delivery vehicles or carriers for hydrophobic drugs. Liposomal delivery systems are discussed above in the context of gene-delivery systems. Certain organic solvents such as dimethylsulfoxide also may be employed, although usually at the cost of greater toxicity. Additionally, the compounds may be delivered using sustained-release systems, such as semi-permeable matrices of solid hydrophobic polymers containing the effective amount of the composition to be administered. Various sustained-release materials are established and available to those of skill in the art. Sustained-release capsules may, depending on their chemical nature, release the compounds for a few weeks up to over 100 days. Depending on the chemical nature and the biological stability of the therapeutic reagent, additional strategies for stabilization may be employed.

For any composition used in the present methods of treatment, a therapeutically effective dose can be estimated initially using a variety of techniques well known in the art. For example, in a cell culture assay, a dose can be formulated in animal models to achieve a circulating concentration range that includes the $IC_{50}$ as determined in cell culture. Dosage ranges appropriate for human subjects can be determined, for example, using data obtained from cell culture assays and other animal studies.

A therapeutically effective dose of an agent refers to that amount of the agent that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods known in the art, in view of the specifics of a subject's condition.

The amount of agent or composition administered will, of course, be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein, and are specifically contemplated.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications fall within the scope of the appended claims.

Example 1

Synthesis of Compound cis-cis-N,N'-(dodeca-5,7-diene-1,12-diyl)-bis-[3-(2'-S-1-methyl-pyrrolidin-2-yl)-pyridinium]dibromide

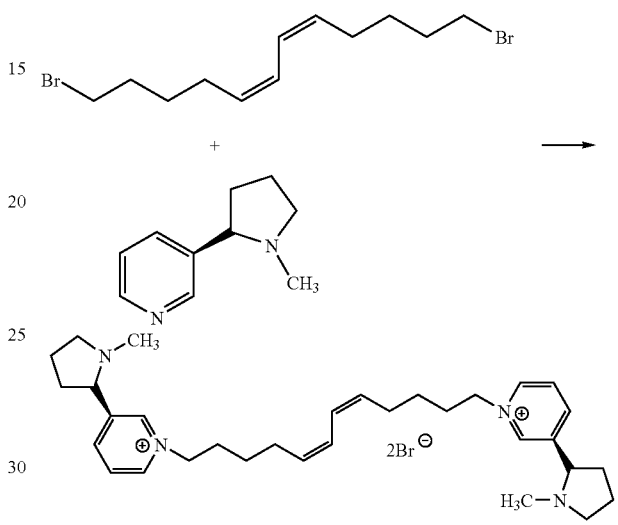

cis-cis-1,12-Dibromo-dodeca-5,7-diene (1 mmol) was added to a solution of S-nicotine (3 mmol) in acetonitrile and the solution refluxed for 24 hours. The acetonitrile was removed in vacuum and the resulting residue was partitioned between ether and water. The aqueous layer was washed extensively with ether until no S-nicotine left in the aqueous layer. The resulting aqueous solution of the product was lyophilized to yield the pure product. (70%). $^1$HNMR (300 MHz, $D_2O$, ppm) 8.60 (s, 2H), 8.59 (d, 2H), 8.32 (d, J=8.4, 2H), 7.88 (t, J=5.7, 2H), 6.12-6.20 (m, 2H), 5.30-5.40 (m, 2H), 4.43 (t, J=7.2, 4H), 3.39 (t, J=8.4, 2H), 3.01-3.06 (m, 2H), 2.16-2.34 (m, 4H), 2.01-2.09 (m, 10H), 1.64-1.88 (m, 10H), 1.25 (p, J=7.5, 4H). $^{13}$CNMR, 144.67, 143.35, 132.20, 128.45, 124.12, 67.65, 62.05, 56.65, 39.41, 33.76, 30.32, 26.34, 25.47, 22.36.

Example 2

Synthesis of Compound cis-cis-N,N'-(dodeca-5,7-diene-1,12-diyl)-bis-(2-methyl-pyridinium)dibromide

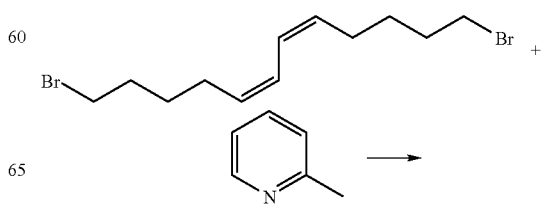

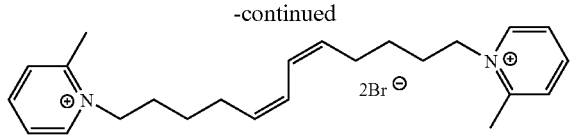

cis-cis-1,12-Dibromo-dodeca-5,7-diene was added to a solution of 2-picoline (3 mmol) in acetonitrile and the solution refluxed for 24 hours. The acetonitrile was removed in vacuum and the resulting residue was partitioned between ether and water. The aqueous layer was washed extensively with ether until no picoline left in the aqueous layer. The resulting aqueous solution of the product was lyophilized to yield the pure product. (76%). $^1$HNMR (300 MHz, D$_2$O, ppm) 8.52 (dd, J=6.3, 2H), 8.17 (dt, J=7.8, J=1.5, 2H), 7.72 (d, J=7.8, 2H), 7.64 (t, J=6.3, 2H), 6.18-6.23 (m, 2H), 5.33-5.41 (m, 2H), 4.37 (t, J=7.1, 4H), 2.66 (s, 6H), 2.09 (q, J=7.5, 4H), 1.72-1.82 (m, 4H), 1.36 (p, J=7.5, 4H). $^{13}$CNMR, 155.26, 145.01, 144.73, 132.25, 130.23, 125.64, 124.15, 58.06, 29.10, 26.38, 25.61, 19.73.

Example 3

Synthesis of Compound cis-cis-N,N'-(dodeca-5,7-diene-1,12-diyl)-bis-(3-methyl-pyridinium)dibromide

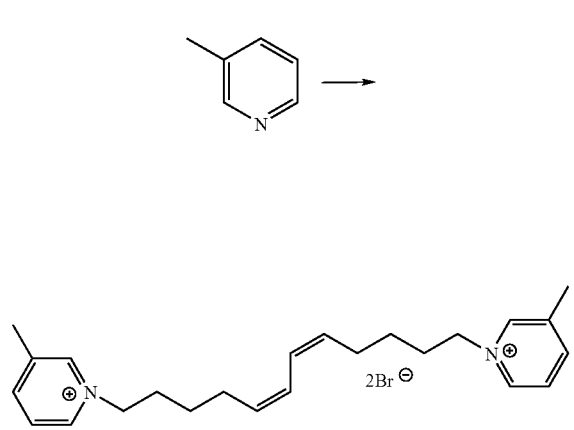

cis-cis-1,12-Dibromo-dodeca-5,7-diene was added to a solution of 3-picoline (3 mmol) in acetonitrile and the solution refluxed for 24 hours. The acetonitrile was removed in vacuum and the resulting residue was partitioned between ether and water. The aqueous layer was washed extensively with ether until no picoline left in the aqueous layer. The resulting aqueous solution of the product was lyophilized to yield the pure product. (76%). $^1$HNMR (300 MHz, D$_2$O, ppm) 8.50 (s, 2H), 8.44 (d, J=6.3, 2H), 8.16 (d, J=7.8, 2H), 7.74 (dd, J=7.8, J=6.3, 2H), 6.15-6.18 (m, 2H), 5.38-5.38 (m, 2H), 4.38 (t, J=5.7, 4H), 2.35 (s, 6H), 2.06 (q, J=7.5, 4H), 1.83 (p, J=7.5, 4H), 1.25 (p, J=7.5, 4H). $^{13}$CNMR, 145.99, 143.71, 141.30, 139.95, 132.19, 127.46, 124.06, 61.69, 30.27, 26.35, 25.44, 17.93.

Example 4

Synthesis of Compound cis-cis-N,N'-(dodeca-5,7-diene-1,12-diyl)-bis-(4-methyl-pyridinium)dibromide

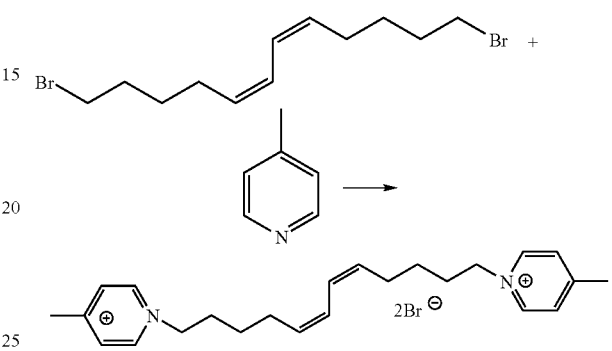

cis-cis-1,12-Dibromo-dodeca-5,7-diene was added to a solution of 4-picoline (3 mmol) in acetonitrile and the solution refluxed for 24 hours. The acetonitrile was removed in vacuum and the resulting residue was partitioned between ether and water. The aqueous layer was washed extensively with ether until no picoline left in the aqueous layer The resulting aqueous solution of the product was lyophilized to yield the pure product. (75%). $^1$HNMR (300 MHz, D$_2$O, ppm), 8.45 (d, J=6.9, 4H), 7.68 (d, J=6.9, 4H), 6.14-6.19 (m, 2H), 5.31-5.39 (m, 2H), 4.35 (t, J=7.2, 4H), 2.47 (s, 6H), 2.07 (q, J=7.2, 4H), 1.83 (p, J=7.5, 4H), 1.25 (p, J=7.5, 4H).

Example 5

Synthesis of Compound cis-cis-N,N'-(dodeca-5,7-diene-1,12-diyl)-bis-(5,6,7,8-tetrahydro-quinolinium)dibromide

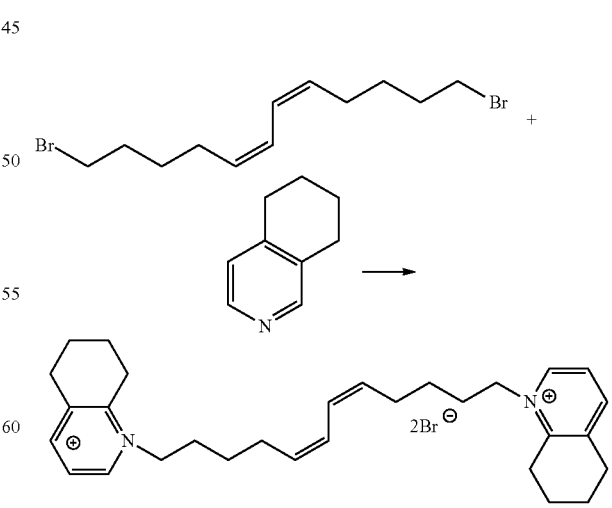

cis-cis-1,12-Dibromo-dodeca-5,7-diene was added to a solution of 5,6,7,8-tetrahydro-quinoline (3 mmol) in acetonitrile and the solution refluxed for 24 hours. The acetonitrile was removed in vacuum and the resulting residue was partitioned between ether and water. The aqueous layer was washed extensively with ether until no quinoline left in the aqueous layer. The resulting aqueous solution of the product was lyophilized to yield the pure product. (75%). $^1$HNMR (300 MHz, D$_2$O, ppm), 8.35 (d, J=6.3, 2H), 7.97 (d, J=8.1, 2H), 7.52 (dd, J=8.1, J=6.3, 2H), 6.16-6.22 (m, 2H), 5.32-5.42 (m, 2H), 4.30 (t, J=7.8, 4H), 2.92 (t, J=6.2, 4H), 2.79 (t, J=6.2, 4H), 2.09 (q, J=7.2, 4H), 1.60-1.83 (m, 12H), 1.36 (p, J=7.5, 4H).

Example 6

Synthesis of Compound cis-cis-N,N'-(dodeca-5,7-diene-1,12-diyl)-bis-(5,6,7,8-tetrahydro-isoquinolinium)dibromide

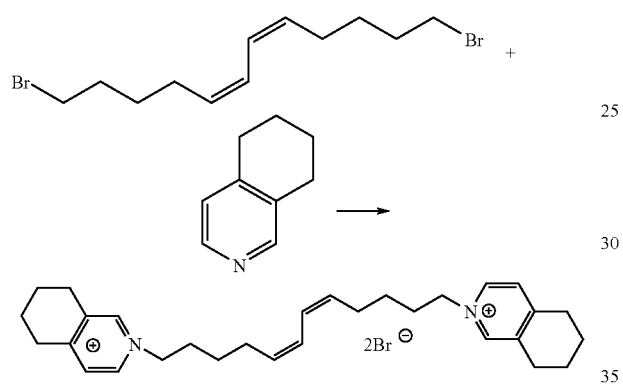

cis-cis-1,12-Dibromo-dodeca-5,7-diene was added to a solution of 5,6,7,8-tetrahydro-isoquinoline (3 mmol) in acetonitrile and the solution refluxed for 24 hours. The acetonitrile was removed in vacuum and the resulting residue was partitioned between ether and water. The aqueous layer was washed extensively with ether until no isoquinoline left in the aqueous layer. The resulting aqueous solution of the product was lyophilized to yield the pure product. (75%). $^1$HNMR (300 MHz, D$_2$O, ppm), 8.30 (s, 2H), 8.19 (d, J=6.6, 2H), 7.50 (d, J=6.3, 2H), 6.09-6.16 (m, 2H), 5.28-5.36 (m, 2H), 4.27 (t, J=7.2, 4H), 2.29-2.82 (br, 4H), 2.67-2.74 (br, 4H), 2.02 (q, J=7.2, 4H), 1.81 (p, J=7.2, 4H), 1.62-1.69 (m, 8H), 1.22 (p, J=7.2, 4H). CNMR158.82, 143.10, 139.60, 138.96, 132.28, 127.92, 124.09, 60.82, 49.13, 30.07, 29.35, 26.32, 26.20, 25.43, 21.01.

Example 7

Synthesis of Compound cis-cis-N,N'-(dodeca-5,7-diene-1,12-diyl)-bis-(2,4-dimethyl-pyridinium)dibromide

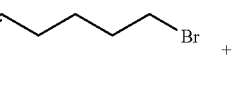

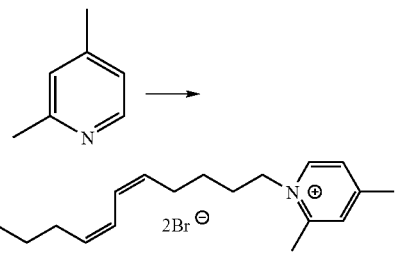

cis-cis-1,12-Dibromo-dodeca-5,7-diene was added to a solution of 2,4-lutidine (3 mmol) in acetonitrile and the solution refluxed for 24 hours. The acetonitrile was removed in vacuum and the resulting residue was partitioned between ether and water. The aqueous layer was washed extensively with ether until no 2,4-lutidine left in the aqueous layer. The resulting aqueous solution of the product was lyophilized to yield the pure product. (75%). $^1$HNMR (300 MHz, D$_2$O, ppm), 8.31 (d, J=6.3, 2H), 7.53 (s, 2H), 7.46 (d, J=6.9, 2H), 6.16-6.22 (m, 2H), 5.32-5.40 (m, 2H), 4.28 (t, J=8.1, 4H), 2.58 (s, 3H), 2.38 (s, 3H), 2.07 (q, J=7.2, 4H), 1.74 (p, J=7.5, 4H), 1.33 (p, J=7.5, 4H). CNMR, 159.20, 153.87, 143.69, 132.32, 130.44, 126.34, 124.18, 57.19, 29.10, 26.41, 25.63, 21.19, 19.46.

Example 8

Synthesis of Compound cis-cis-N,N'-(dodeca-5,7-diene-1,12-diyl)-bis-(3,4-dimethyl-pyridinium)dibromide

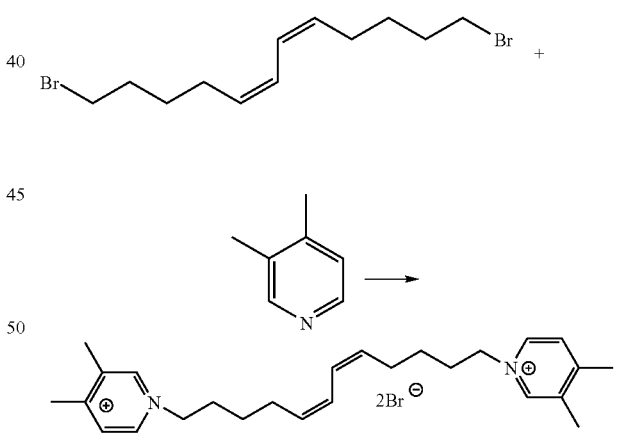

cis-cis-1,12-Dibromo-dodeca-5,7-diene was added to a solution of 3,4-lutidine (3 mmol) in acetonitrile and the solution refluxed for 24 hours. The acetonitrile was removed in vacuum and the resulting residue was partitioned between ether and water. The aqueous layer was washed extensively with ether until no 3,4-lutidine left in the aqueous layer. The resulting aqueous solution of the product was lyophilized to yield the pure product. (75%). $^1$HNMR (300 MHz, D$_2$O, ppm), 8.34 (s, 1H), 8.29 (d, J=6.3, 1H), 7.60 (d, J=6.3, 1H), 6.13-6.18 (m, 2H), 5.30-5.38 (m, 2H), 4.31 (t, J=7.2, 4H), 2.37 (s, 3H), 2.25 (s, 3H), 2.05 (q, J=7.2, 4H), 1.81 (p, J=7.5, 4H), 1.24 (p, J=7.5, 4H). CNMR, 158.66, 142.37, 140.71, 138.65, 132.25, 128.23, 124.07, 60.80, 30.11, 26.31, 25.42, 19.69, 16.34.

Example 9

Synthesis of Compound cis-cis-N,N'-(dodeca-5,7-diene-1,12-diyl)-bis-(3,5-dimethyl-pyridinium)dibromide

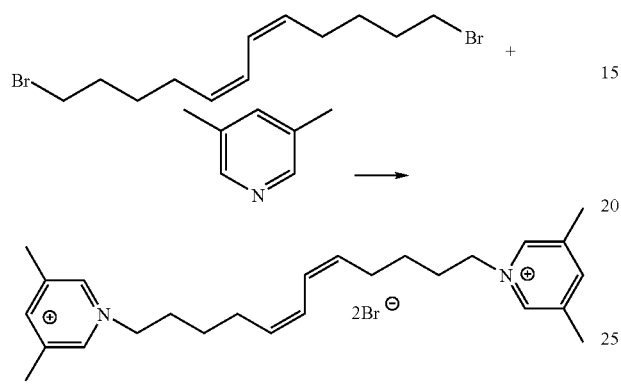

cis-cis-1,12-Dibromo-dodeca-5,7-diene was added to a solution of 3,5-lutidine (3 mmol) in acetonitrile and the solution refluxed for 24 hours. The acetonitrile was removed in vacuum and the resulting residue was partitioned between ether and water. The aqueous layer was washed extensively with ether until no 3,5-lutidine left in the aqueous layer. The resulting aqueous solution of the product was lyophilized to yield the pure product. (75%). $^1$HNMR (300 MHz, D$_2$O, ppm), 8.29 (s, 4H), 7.99 (s, 2H), 6.12-6.18 (m, 2H), 5.30-5.38 (m, 2H), 4.31 (t, J=7.5, 4H), 2.30 (s, 6H), 2.05 (q, J=7.2, 4H), 1.81 (p, J=7.5, 4H), 1.24 (p, J=7.5, 4H). CNMR, 146.56, 140.96, 139.11, 132.28, 124.09, 61.49, 30.21, 26.34, 25.43, 17.73.

Example 10

Synthesis of Compound N,N'-[1,4-phenylenedi-(4-butanyl)]-bis-[3-(2'-S-1-methyl-pyrrolidin-2-yl)-pyridinium]dibromide

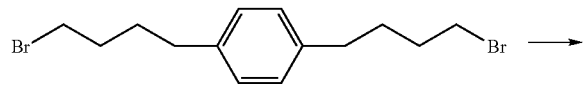

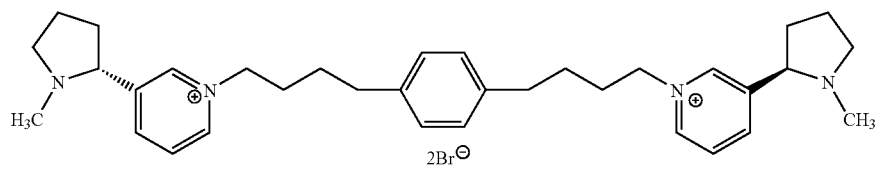

1,4-Bis-(4-bromo-butyl)-benzene was added to a solution of S-nicotine (3 mmol) in acetonitrile and the solution refluxed for 24 hours. The acetonitrile was removed in vacuum and the resulting residue was partitioned between ether and water. The aqueous layer was washed extensively with ether until no S-nicotine left in the aqueous layer. The resulting aqueous solution of the product was lyophilized to yield the pure product. (75%). $^1$HNMR (300 MHz, D$_2$O, ppm), 8.57-8.59 (m, 4H), 8.35 (d, J=8.1, 2H), 7.88 (dd, J=7.8, J=6.6, 2H), 7.01 (s, 4H), 4.45 (t, J=7.5, 4H), 3.40 (t, 2H), 3.04-3.10 (m, 2H), 2.49 (t, J=7.5, 4H), 2.30-2.40 (m, 2H), 2.18-2.29 (m, 2H), 2.03 (s, 6H), 1.80-1.90 (m, 8H), 1.40-1.55 (m, 4H). CNMR, 144.65, 143.48, 143.30, 139.76, 128.74, 128.42, 67.61, 61.99, 56.62, 39.37, 33.96, 33.73, 30.17, 27.28, 22.33.

Example 11

Synthesis of Compound N,N'-[1,4-phenylenedi-(4-butanyl)]-bis-(2-methylpyridinium)dibromide

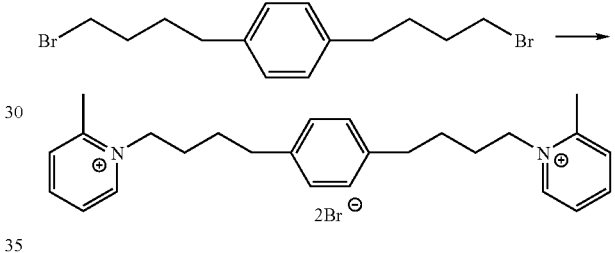

1,4-Bis-(4-bromo-butyl)-benzene was added to a solution of 2-picoline (3 mmol) in acetonitrile and the solution refluxed for 24 hours. The acetonitrile was removed in vacuum and the resulting residue was partitioned between ether and water. The aqueous layer was washed extensively with ether until no 2-picoline left in the aqueous layer. The resulting aqueous solution of the product was lyophilized to yield the pure product. (75%). $^1$HNMR (300 MHz, D$_2$O, ppm), 8.49 (dd, J=6.0, 1.2, 2H), 8.17 (dt, J=8.1, J=1.5, 2H), 7.70 (d, J=8.1, 2H), 7.65 (dt, J=8.1, J=1.2, 2H), 7.04 (s, 4H), 4.37 (t, J=7.2, 4H), 2.62 (s, 6H), 2.51 (t, J=7.2, 4H), 1.77 (p, J=7.8, 4H), 1.57 (p, J=7.8, 4H). CNMR. 145.05, 144.73, 139.79, 130.24, 128.78, 125.64, 58.02, 34.11, 29.01, 27.49, 19.70.

Example 12

Synthesis of Compound N,N'-[1,4-phenylenedi-(4-butanyl)]-bis-(3-methylpyridinium)dibromide

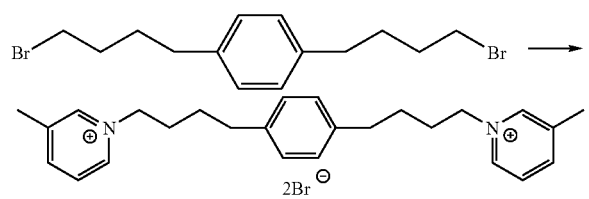

1,4-Bis-(4-bromo-butyl)-benzene was added to a solution of 3-picoline (3 mmol) in acetonitrile and the solution refluxed for 24 hours. The acetonitrile was removed in vacuum and the resulting residue was partitioned between ether and water. The aqueous layer was washed extensively with ether until no 3-picoline left in the aqueous layer. The resulting aqueous solution of the product was lyophilized to yield the pure product. (75%). $^1$HNMR (300 MHz, D$_2$O, ppm), 8.45 (s, 2H), 8.40 (d, J=6.6, 2H), 8.16 (d, J=8.1, 2H), 7.72 (dd, J=8.1, J=6.0, 2H), 7.00 (s, 4H), 4.37 (t, J=7.5, 4H), 2.47 (t, J=7.5, 4H), 2.34 (s, 6H), 1.82 (p, J=7.5, 4H), 1.46 (p, J=7.5, 4H). CNMR. 146.02, 143.68, 141.68, 139.96, 139.79, 128.75, 127.46, 61.69, 34.04, 30.14, 27.28, 17.90.

Example 13

Synthesis of Compound N,N'-[1,4-phenylenedi-(4-butanyl)]-bis-(4-methylpyridinium)dibromide

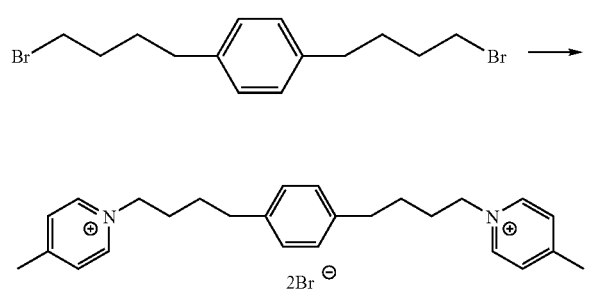

1,4-Bis-(4-bromo-butyl)-benzene was added to a solution of 4-picoline (3 mmol) in acetonitrile and the solution refluxed for 24 hours. The acetonitrile was removed in vacuum and the resulting residue was partitioned between ether and water. The aqueous layer was washed extensively with ether until no 4-picoline left in the aqueous layer. The resulting aqueous solution of the product was lyophilized to yield the pure product. (75%). $^1$HNMR (300 MHz, D$_2$O, ppm), 8.38 (d, J=6.9, 4H), 7.64 (d, J=6.9, 4H), 6.98 (s, 4H), 4.33 (t, J=7.2, 4H), 2.46 (t, J=7.2, 4H), 2.44 (s, 6H), 1.81 (p, J=7.5, 4H), 1.45 (p, J=7.5, 4H). CNMR. 159.99, 143.04, 139.79, 128.74, 128.65, 60.99, 34.02, 30.03, 27.26, 21.50.

Example 14

Synthesis of Compound N,N'-[1,4-phenylenedi-(4-butanyl)]-bis-(3-ethylpyridinium)dibromide

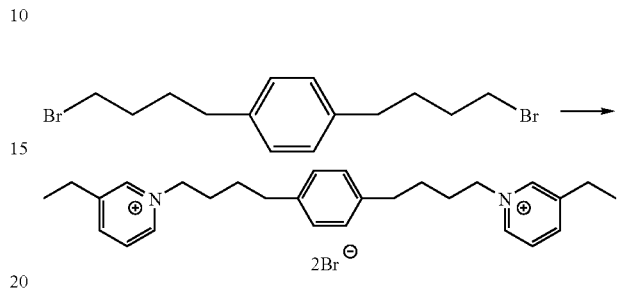

1,4-Bis-(4-bromo-butyl)-benzene was added to a solution of 3-ethylpyridine (3 mmol) in acetonitrile and the solution refluxed for 24 hours. The acetonitrile was removed in vacuum and the resulting residue was partitioned between ether and water. The aqueous layer was washed extensively with ether until no 3-ethylpyridine left in the aqueous layer. The resulting aqueous solution of the product was lyophilized to yield the pure product. (75%). $^1$HNMR (300 MHz, D$_2$O, ppm), 8.45 (s, 2H), 8.41 (d, J-6.0, 2H), 8.19 (d, J=8.4, 2H), 7.73 (dd, J=8.1, J=6.0, 2H), 6.97 (s, 4H), 4.37 (t, J=7.2, 4H), 2.66 (q, 7.8, 2H), 2.49 (t, J=7.2, 4H), 1.83 (p, J=7.5, 4H), 1.45 (p, J-1.5, 4H), 1.09 (t, J=7.8, 6H). CNMR. 145.61, 145.08, 143.09, 141.51, 139.78, 128.75, 127.68, 61.70, 34.01, 30.13, 27.24, 25.70, 13.92.

Example 15

Synthesis of Compound N,N'-[1,4-phenylenedi-(4-butanyl)]-bis-(5,6,7,8-tetrahydroquinolinium)dibromide

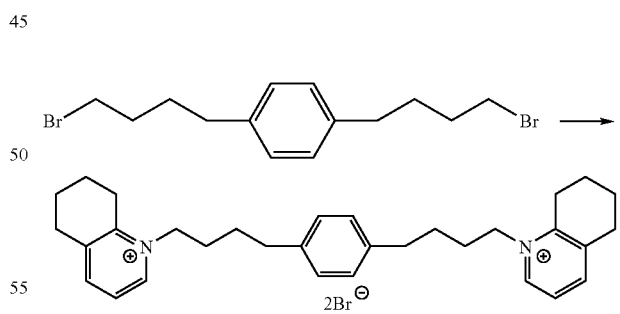

1,4-Bis-(4-bromo-butyl)-benzene was added to a solution of tetrahydroquinoline (3 mmol) in acetonitrile and the solution refluxed for 24 hours. The acetonitrile was removed in vacuum and the resulting residue was partitioned between ether and water. The aqueous layer was washed extensively with ether until no tetrahydroquinoline left in the aqueous layer. The resulting aqueous solution of the product was lyophilized to yield the pure product. (75%). $^1$HNMR (300 MHz, D$_2$O, ppm), 8.30 (d, J=6.3, 2H), 7.95 (d, J=7.8, 2H), 7.49 (dd, J=8.1, J=6.3, 2H), 7.02 (s, 4H), 4.28 (t, 7.5, 4H), 2.83 (t, J=7.5, 4H), 2.77 (t, J=7.5, 4H), 2.49 (t, J=7.5, 4H), 1.66-1.80 (m, 8H), 1.35-1.63 (m, 8H).

Example 16

Synthesis of Compound N,N'-[1,4-phenylenedi-(4-butanyl)]-bis-(5,6,7,8-tetrahydroisoquinolinium) dibromide

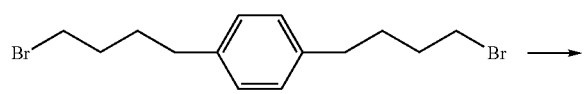

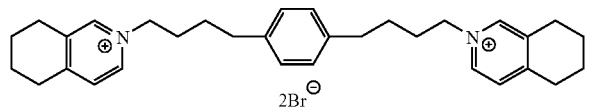

1,4-Bis-(4-bromo-butyl)-benzene was added to a solution of tetrahydroisoquinoline (3 mmol) in acetonitrile and the solution refluxed for 24 hours. The acetonitrile was removed in vacuum and the resulting residue was partitioned between ether and water. The aqueous layer was washed extensively with ether until no tetrahydroisoquinoline left in the aqueous layer. The resulting aqueous solution of the product was lyophilized to yield the pure product. (75%). $^1$HNMR (300 MHz, D$_2$O, ppm), 8.21 (s, 2H), 8.13 (d, J=6.3, 2H), 7.46 (d, J=6.3, 2H), 6.96 (s, 4H), 4.25 (t, J=7.2, 4H), 2.2.78-2.84 (br, 4H), 2.63-2.70 (br, 4H), 2.44 (t, J=7.2, 4H), 1.78 (p, J=7.5, 4H), 1.64-1.70 (m, 8H), 1.42 (p, J=7.5, 4H). CNMR, 158.77, 143.03, 139.78, 139.56, 138.88, 128.72, 127.84, 60.79, 49.11, 34.01, 29.91, 29.31, 27.16, 26.16, 20.99.

Example 17

Synthesis of Compound N,N'-[1,4-phenylenedi-(4-butanyl)]-bis-[3-(3-hydroxy-propyl)-pyridinium] dibromide

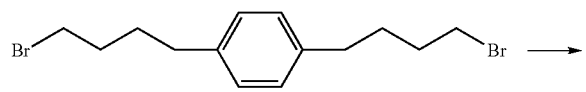

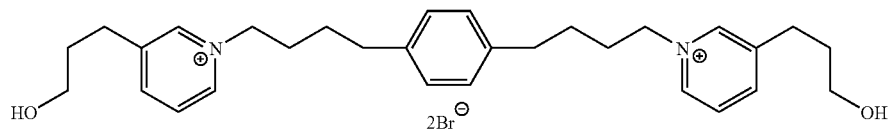

1,4-Bis-(4-bromo-butyl)-benzene was added to a solution of (3-hydroxy-propyl)-pyridine (3 mmol) in acetonitrile and the solution refluxed for 24 hours. The acetonitrile was removed in vacuum and the resulting residue was partitioned between ether and water. The aqueous layer was washed extensively with ether until no (3-hydroxy-propyl)-pyridine left in the aqueous layer. The resulting aqueous solution of the product was lyophilized to yield the pure product. (75%). $^1$HNMR (300 MHz, D$_2$O, ppm), 8.49 (s, 2H), 8.43 (d, J=6.0, 2H), 8.22 (d, J=8.1, 2H), 7.75 (dd, J=7.8, J=6.0, 2H), 6.98 (s, 4H), 4.38 (t, J=7.2, 4H), 3.45 (t, J=6.6, 4H), 2.72 (t, J=7.8, 4H), 2.46 (t, J=7.5, 4H), 1.83 (p, J=7.5, 4H), 1.70-1.75 )m, 4H), 1.44 (p, J=7.5, 4H). CNMR, 145.53, 143.51, 141.78, 139.78, 128.75, 127.78, 61.75, 60.67, 34.01, 32.17, 30.13, 28.81, 27.24.

Example 18

Synthesis of Compound N,N'-[1,4-phenylenedi-(4-butanyl)]-bis-(2,4-dimethylpyridinium)dibromide

1,4-Bis-(4-bromo-butyl)-benzene was added to a solution of 2,4-lutidine (3 mmol) in acetonitrile and the solution refluxed for 24 hours. The acetonitrile was removed in vacuum and the resulting residue was partitioned between ether and water. The aqueous layer was washed extensively with ether until no 2,4-lutidine left in the aqueous layer. The resulting aqueous solution of the product was lyophilized to yield the pure product. (75%). $^1$HNMR (300 MHz, D$_2$O, ppm), 8.27 (d, J=6.6, 2H), 7.50 (s, 2H), 7.45 (d, J=6.6, 2H), 7.02 (s, 4H), 4.28 (t, J=7.2, 4H), 2.52 (s, 6H), 2.48 (t, J=7.2, 4H), 2.38 (s, 6H), 2.20 (s, 3H), 1.79 (p, J=7.5, 4H), 1.42 (p, J=7.5, 4H).

Example 19

Synthesis of Compound N,N'-[1,4-phenylenedi-(4-butanyl)]-bis-(3,4-dimethylpyridinium)dibromide

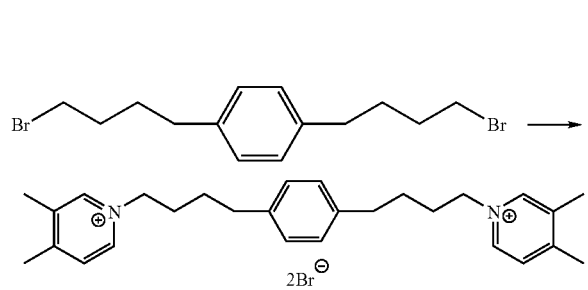

1,4-Bis-(4-bromo-butyl)-benzene was added to a solution of 3,4-lutidine (3 mmol) in acetonitrile and the solution refluxed for 24 hours. The acetonitrile was removed in vacuum and the resulting residue was partitioned between ether and water. The aqueous layer was washed extensively with ether until no 3,4-lutidine left in the aqueous layer. The resulting aqueous solution of the product was lyophilized to yield the pure product. (75%). $^1$HNMR (300 MHz, D$_2$O, ppm), 8.25 (s, 2H), 8.22 (d, J=6.0, 2H), 7.55 (d, J=6.0, 2H), 6.96 (s, 4H), 4.27 (t, J=7.2, 4H), 2.45 (t, J=7.2, 4H), 2.34 (s, 6H), 2.21 (s, 6H), 1.79 (p, J=7.5, 4H), 1.42 (p, J=7.5, 4H). CNMR, 158.64, 142.28, 140.66, 139.78, 138.61, 128.72, 128.18, 34.02, 29.94, 27.20, 19.67, 16.29.

Example 20

Synthesis of Compound N,N'-[1,4-phenylenedi-(4-butanyl)]-bis-(3,5-dimethylpyridinium)dibromide

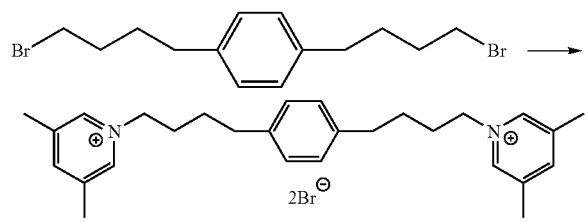

1,4-Bis-(4-bromo-butyl)-benzene was added to a solution of 3,5-lutidine (3 mmol) in acetonitrile and the solution refluxed for 24 hours. The acetonitrile was removed in vacuum and the resulting residue was partitioned between ether and water. The aqueous layer was washed extensively with ether until no 3,5-lutidine left in the aqueous layer. The resulting aqueous solution of the product was lyophilized to yield the pure product. (75%). $^1$HNMR (300 MHz, D$_2$O, ppm), 8.23 (s, 4H), 7.97 (s, 2H), 6.97 (s, 4H), 4.29 (t, J=7.2, 4H), 2.45 (t, J=7.2, 4H), 2.27 (s, 12H), 1.81 (p, J=7.5, 4H), 1.45 (p, J=7.5, CNMR, 146.50, 140.89, 139.79, 139.04, 128.74, 61.46, 34.04, 30.03, 27.22, 17.70.

Example 21

Synthesis of Compound 5-[2-(5-hydroxy-pent-1-ynyl)-phenyl]-pent-4-yn-1-ol

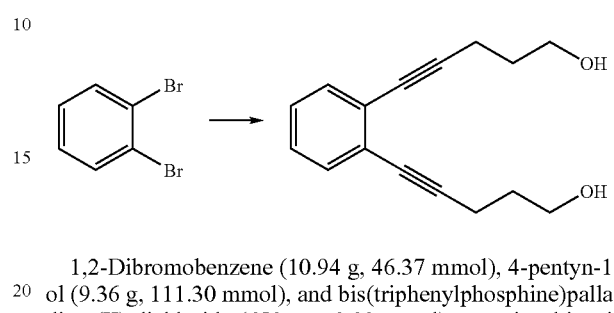

1,2-Dibromobenzene (10.94 g, 46.37 mmol), 4-pentyn-1-ol (9.36 g, 111.30 mmol), and bis(triphenylphosphine)palladium(II) dichloride (650 mg, 0.93 mmol) was stirred in triethylamine (150 mL) under nitrogen for 5 min. Copper(I) iodide (88 mg, 0.46 mmol) was added and the mixture was stirred for 4 hrs at 85° C. for 6 days. The mixture was cooled to room temperature and filtered through a celite pad, rinsed with ethylacetate. The combined filtrate was evaporated to dryness under reduced pressure. The resulting residue was purified by column chromatography (chloroform:methanol 30:1) to afford 5.33 g of the title compound. Yield: 47%. $^1$H NMR (300 MHz, D$_2$O) δ 1.85 (m, 4H), 2.58 (t, J=6.6 Hz, 4H), 3.82 (t, J=6.0 Hz, 4H), 7.18 (m, 2H), 7.36 (m, 2H) ppm; $^{13}$C NMR (75 MHz, CDCl$_3$) δ 16.3, 31.4, 62.4, 80.2, 93.3, 126.0, 127.4, 131.8 ppm.

Example 22

Synthesis of Compound 1,2-bis-(5-bromo-pent-1-ynyl)-benzene

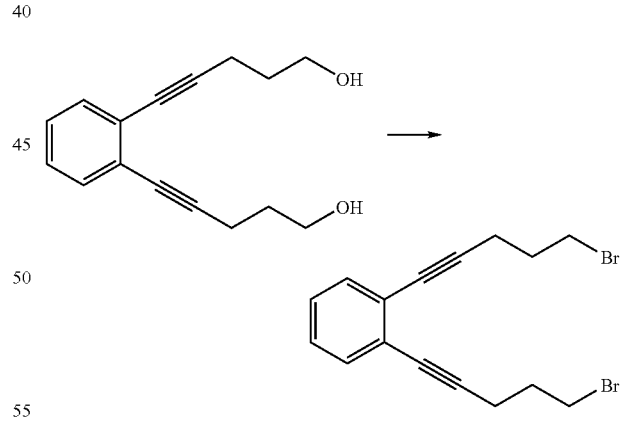

5-[2-(5-Hydroxy-pent-1-ynyl)-phenyl]-pent-4-yn-1-ol (2.40 g, 9.90 mmol) and carbon tetrabromide (8.21 g, 24.75 mmol) were dissolved in dry methylene chloride (30 mL) and cooled to 0° C. Triphenyl phosphine (6.82 g, 25.99 mmol) in methylene chloride (15 mL) was added dropwise and the mixture was stirred for 1 h at 0° C. The mixture was poured into hexanes (200 mL) and then filtered through a short silica gel column, washed with ethylacetate/hexanes (¼). The combined organic solvents were evaporated to dryness under reduced pressure. The resulting residue was purified by column chromatography (hexanes:ethylacetate 30:1) to afford 2.48 g of the title compound. Yield: 68%. $^1$H NMR (300 MHz, CDCl$_3$) δ 2.16 (m, 4H), 2.68 (t, J=6.6 Hz, 4H), 3.65 (dt, J=6.6, 0.6 Hz, 4H), 7.20 (m, 2H), 7.38 (m, 2H) ppm; $^{13}$C NMR (75 MHz, CDCl$_3$) δ 18.6, 31.8, 32.7, 80.7, 91.8, 125.9, 127.6, 131.9 ppm.

Example 23

Synthesis of Compound 1,2-bis-[5-(2-methyl-pyridinium)-pent-1-ynyl]-benzene dibromide

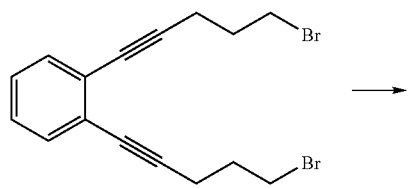

→

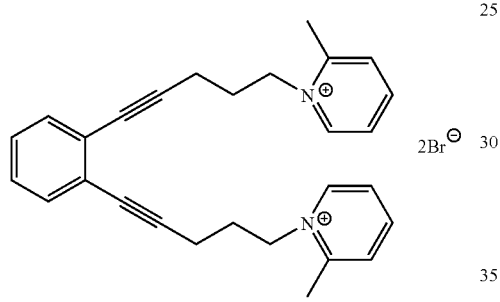

A mixture of 1,2-bis-(5-bromo-pent-1-ynyl)-benzene (264 mg, 0.72 mmol) and 2-picoline (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 327 mg of the title compound. Yield: 82 %. $^1$H NMR (300 MHz, CD$_3$OD) δ 2.35 (m, 4H), 2.81 (t, J =6.6 Hz, 4H), 3.02 (s, 6H), 4.91 (t, J =7.5 Hz, 4H), 7.27-7.50 (m, 4H), 7.92-8.15 (m, 4H), 8.45 (t, J=7.8 Hz, 2H), 9.11 (d, J=6.3 Hz, 2H) m; $^{13}$C NMR (75 MHz, CD$_3$OD) δ 17.6, 21.1, 30.1, 5.8.2, 81.9, 92.9, 126.4, 127.0, 129.2, 129.3, 131.5, 133.1, 146.4, 156.7 ppm.

Example 24

Synthesis of Compound 1,2-bis-[5-(3-methyl-pyridinium)-pent-1-ynyl]-benzene dibromide

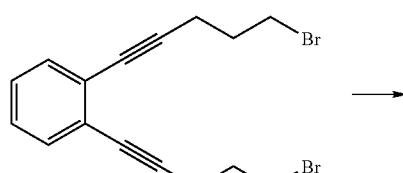

→

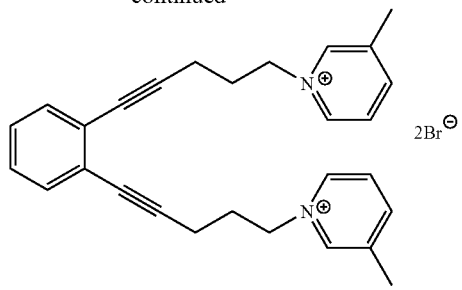

A mixture of 1,2-bis-(5-bromo-pent-1-ynyl)-benzene (270 mg, 0.73 mmol) and 3-picoline (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 350 mg of the title compound. Yield: 86%. $^1$H NMR (300 MHz, CD$_3$OD) δ 2.45 (m, 4H), 2.56 (s, 6H) 2.78 (t, J=6.6 Hz, 4H), 4.95 (t, J =7.2 Hz, 4H), 7.22-7.42 (m, 4H), 8.05 (dd, J=8.1, 6.0 Hz, 2H), 8.39 (d, J=7.8 Hz, 2H), 9.10 (d, J=6.0 Hz, 2H), 9.19 (s, 2H) ppm; $^{13}$C NMR (75 MHz, CD$_3$OD) δ 17.6, 18.9, 31.2, 61.9, 81.6, 92.8, 126.4, 128.7, 129.0, 132.9, 140.9, 143.1, 145.6, 147.3 ppm.

Example 25

Synthesis of Compound 1,2-bis-[5-(4-methyl-pyridinium)-pent-1-ynyl]-benzene dibromide

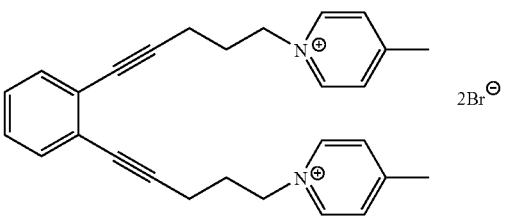

→

A mixture of 1,2-bis-(5-bromo-pent-1-ynyl)-benzene (268 mg, 0.73 mmol) and 4-picoline (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 435 mg of the title compound. Yield: 86%. $^1$H NMR (300 MHz, CD$_3$OD) δ 2.41 (m, 4H), 2.51 (s, 6H), 2.78 (t, J=6.6 Hz, 4H 4.91 (t, J=6.6 Hz, 4H), 7.30 (s, 4H), 7.92 (d, J=6.3 Hz, 4H), 9.05 (d, J=6.3 Hz, 4H)

ppm; $^{13}$C NMR (75 MHz, CD$_3$OD) δ 17.5, 22.3, 31.0, 61.4, 81.5, 92.8, 126.4, 129.0, 129.8, 132.9, 144.9, 161.1 ppm.

Example 26

Synthesis of Compound 1,2-bis-[5-(2,4-dimethyl-pyridinium)-pent-1-ynyl]-benzene dibromide

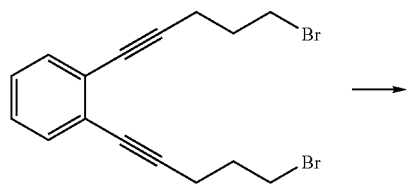

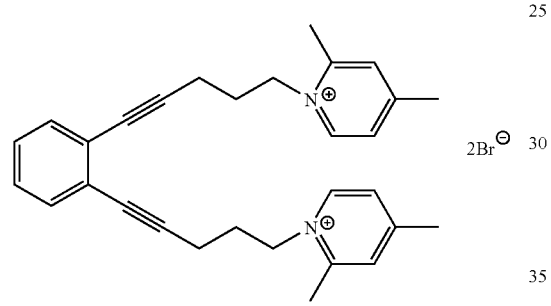

A mixture of 1,2-bis-(5-bromo-pent-1-ynyl)-benzene (268 mg, 0.73 mmol) and 2,4-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 343 mg of the title compound. Yield: 81%. $^1$H NMR (300 MHz, CD$_3$OD) δ 2.34 (m, 4H), 2.52 (s, 3H), 2.84 (t, J=6.6 Hz, 4H), 2.97 (s, 3H), 4.87 (t, J=7.5 Hz, 4H), 7.27-7.45 (m, 4H), 7.80 (d, J=6.3 Hz, 2H), 7.87 (s, 2H), 8.99 (d, J=6.3 Hz, 2H) ppm; $^{13}$C NMR (75 MHz, CD$_3$OD) δ 17.6, 20.9, 22.0, 30.1, 57.5, 81.6, 93.0, 126.4, 127.6, 129.1, 131.7, 133.0, 145.5, 155.5, 160.3 ppm.

Example 27

Synthesis of Compound 1,2-bis-[5-(3,4-dimethyl-pyridinium)-pent-1-ynyl]-benzene dibromide

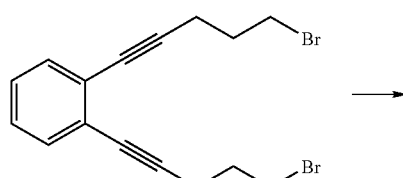

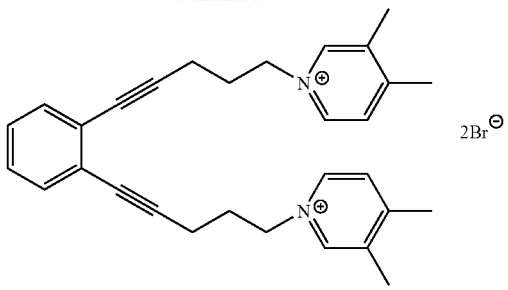

A mixture of 1,2-bis-(5-bromo-pent-1-ynyl)-benzene (276 mg, 0.75 mmol) and 3,4-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 355 mg of the title compound. Yield: 81%. $^1$H NMR (300 MHz, CD$_3$OD) δ 2.37 (s, 3H), 2.40 (s, 3H), 2.44 (m, 4H), 2.79 (t, J=6.6 Hz, 4H), 4.88 (t, J=6.6 Hz, 4H), 7.29 (s, 4H), 7.86 (d, J=6.3 Hz, 2H), 8.95 (d, J=6.3 Hz, 2H), 9.06 (s, 2H), ppm; $^{13}$C NMR (75 MHz, CD$_3$OD) δ 17.3, 17.7, 20.4, 31.1, 61.2, 81.3, 93.0, 126.5, 129.0, 129.4, 132.8, 139.5, 142.7, 144.3, 159.8 ppm.

Example 28

Synthesis of Compound 1,2-bis-[5-(3,5-dimethyl-pyridinium)-pent-1-ynyl]-benzene dibromide

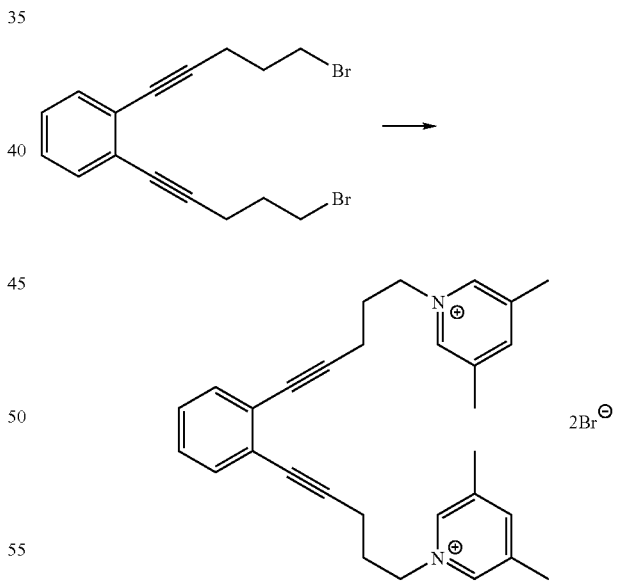

A mixture of 1,2-bis-(5-bromo-pent-1-ynyl)-benzene (280 mg, 0.76 mmol) and 3,5-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 363 mg of the title compound. Yield: 82%. $^1$H NMR (300 MHz, CD$_3$OD) δ 2.42 (m, 4H), 2.51 (s, 6H), 2.76 (t, J=6.9 Hz, 4H), 4.86 (t, J=6.9 Hz, 4H), 7.30 (m, 4H), 8.13 (s, 2H), 8.95 (s, 4H) ppm; $^{13}$C NMR (75 MHz, CD$_3$OD) δ 17.7, 18.7, 31.2, 61.9, 81.6, 92.9, 126.6, 129.0, 132.8, 140.2, 142.9, 147.9 ppm.

Example 29

Synthesis of Compound 1,2-bis-(5-quinolinium-pent-1-ynyl)-benzene dibromide

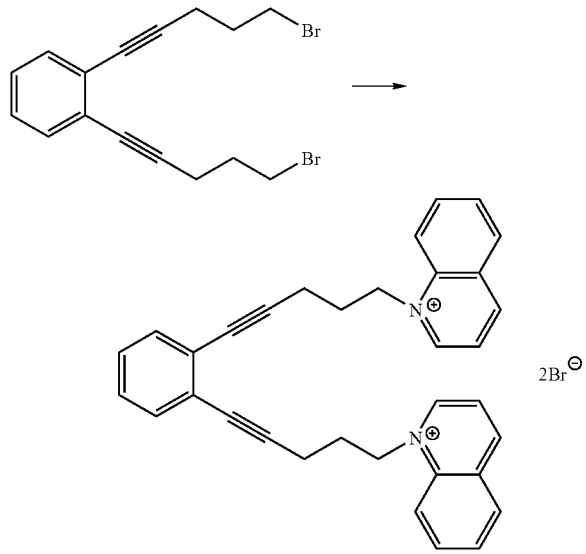

A mixture of 1,2-bis-(5-bromo-pent-1-ynyl)-benzene (249 mg, 0.68 mmol) and quinoline (1 mL) was heated at 60-70° C. for 12 hrs. The resulted mixture was washed with diethyl ether and then dissolved in water (30 mL), the aqueous solution was extracted with chloroform (20 mL×3). Water was removed by lyophilization to afford 317 mg of the title compound. Yield: 75 %. $^1$H NMR (300 MHz, CD$_3$OD) δ 2.42 (m, 4H), 2.78 (t, J=6.6 Hz, 4H), 5.36 (t, J=6.9 Hz, 4H), 7.02-7.28 (m, 4H), 7.97 (t, J =7.5 Hz, 2H), 8.07-8.40 (m, 4H), 8.67 (d, J=9.0 Hz, 2H), 9.15 (d, J=8.4 Hz, 2H), 9.15 (d, J=8.4 Hz, 2H), 9.70 (d, J=5.7 Hz, 2H) ppm; $^{13}$C NMR (75 MHz, CD$_3$OD) δ 17.8, 29.8, 58.5, 81.6, 92.9, 119.7, 123.2, 126.2, 129.0, 130.5, 131.3, 132.0, 132.7, 137.2, 139.0, 149.0, 150.6 ppm.

Example 30

Synthesis of Compound 1,2-bis-(5-isoquinolinium-pent-1-ynyl)-benzene dibromide

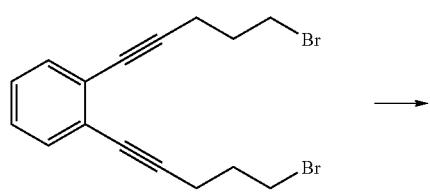

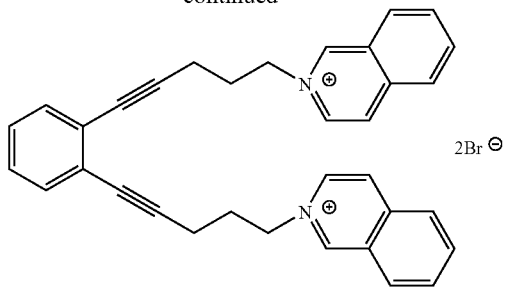

A mixture of 1,2-bis-(5-bromo-pent-1-ynyl)-benzene (252 mg, 0.68 mmol) and isoquinoline (1 mL) was heated at 60-70° C. for 12 hrs. The resulted mixture was washed with diethyl ether and then dissolved in water (30 mL), the aqueous solution was extracted with chloroform (20 mL×3). Water was removed by lyophilization to afford 319 mg of the title compound. Yield: 74%. $^1$H NMR (300 MHz, CD$_3$OD) δ 2.46 (m, 4H), 2.77 (t, J=6.3 Hz, 4H), 5.01 (t, J=6.6 Hz, 4H), 6.91 (m, 2H), 7.04 (m, 2H), 7.90-8.50 (m, 10H), 8.78 (d, J=6.9 Hz, 2H), 10.10 (s, 2H) ppm; $^{13}$C NMR (75 MHz, CD$_3$OD) δ 17.8, 30.8, 62.1, 81.3, 92.7, 125.7, 127.3, 128.1, 128.5, 131.2, 131.4, 132.1, 132.2, 135.6, 137.9, 138.4, 150.8 ppm.

Example 31

Synthesis of Compound 1,2-bis-[5-(2'-S-nicotinium-pent-1-ynyl)]benzene dibromide

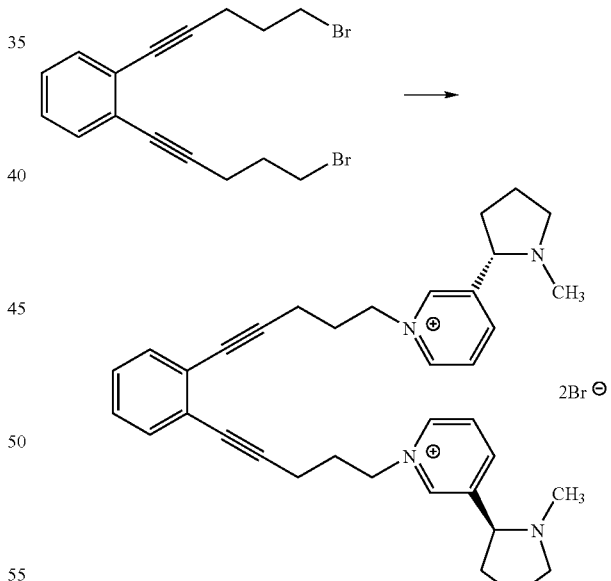

A mixture of 1,2-bis-(5-bromo-pent-1-ynyl)-benzene (330 mg, 0.90 mmol) and S-nicotine (1 mL) was heated at 60-70° C. for 12 hrs. The resulted mixture was washed with diethyl ether and then dissolved in water (20 mL), the aqueous solution was extracted with chloroform (20 mL×3). Water was removed by lyophilization to afford 340 mg of the title compound. Yield: 55%. $^1$H NMR (300 MHz, CD$_3$OD) δ 2.00-2.82 (m, 16H), 2.55 (s, 6H), 2.90 (m, 2H), 3.55 (m, 2H), 4.17 (m, 2H), 4.95 (t, J=6.9 Hz, 4H), 7.27 (m, 2H), 7.37 (m, 2H), 8.17 (dd, J=7.8, 6.3 Hz, 2H), 8.69 (d, J=8.4 Hz, 2H), 9.15 (d, J=6.0

Hz, 2H), 9.40 (s, 2H) ppm; $^{13}$C NMR (75 MHz, CD$_3$OD) δ 17.5, 23.5, 30.9, 34.1, 40.3, 57.6, 62.4, 68.7, 81.9, 92.7, 126.4, 129.1, 129.6, 133.0, 141.1, 145.8, 146.0, 146.5 ppm.

Example 32

Synthesis of Compound
5-[2-(5-hydroxy-pentyl)-phenyl]-pentan-1-ol

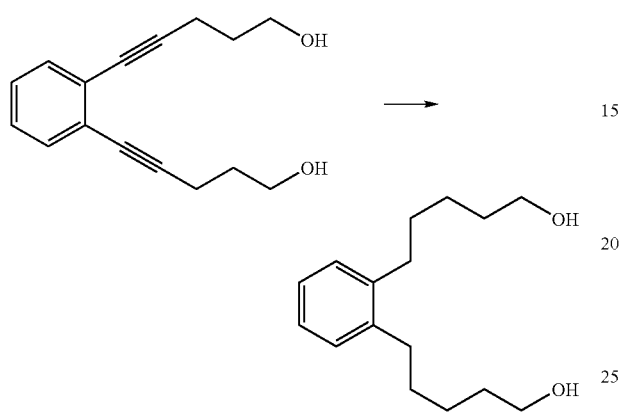

5-[2-(5-Hydroxy-pent-1-ynyl)-phenyl]-pent-4-yn-1-ol (2.70 g, 11.14 mmol) was dissolved in ethanol (30 mL) and 10% Pd/C (2.5% w/w) was added. The resulting mixture was hydrogenated on a Parr hydrogenation apparatus (45 psi) for 4 hrs. The catalyst was removed by filtration through a Celite pad. The filter cake was rinsed with methanol, and the combined organic liquors were concentrated under reduced pressure. The crude product was purified by column chromatography (chloroform:methanol 20:1) to afford 2.55 g of the title compound. Yield: 91%. $^1$H NMR (300 MHz, CDCl$_3$) δ 1.38-1.67 (m, 12H), 2.60 (t, J=7.8 Hz, 4H), 3.59 (t, J=6.6 Hz, 4H), 7.11 (m, 4H) ppm; $^{13}$C NMR (75 MHz, CDCl$_3$) δ 26.0, 31.3, 32.6, 32.8, 62.6, 125.8, 129.1, 140.2 ppm.

Example 33

Synthesis of Compound
1,2-bis-(5-bromo-pentyl)-benzene

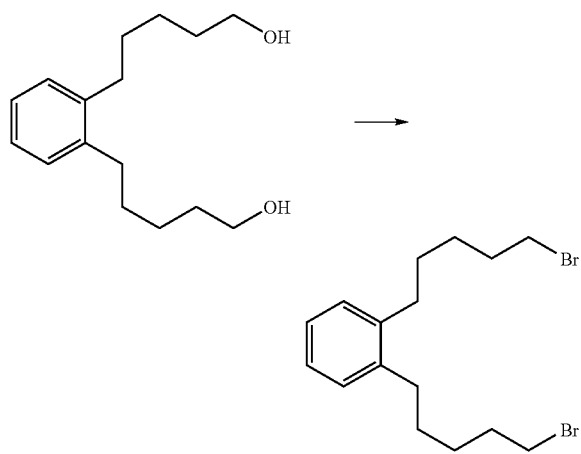

5-[2-(5-Hydroxy-pentyl)-phenyl]-pentan-1-ol (2.50 g, 10.00 mmol) and carbon tetrabromide (8.29 g, 25.00 mmol) were dissolved in dry methylene chloride (30 mL) and cooled to 0° C. Triphenyl phosphine (6.88 g, 26.25 mmol) in methylene chloride (15 mL) was added dropwise and the mixture was stirred for 1 h at 0° C. The mixture was poured into hexanes (200 mL) and then filtered through a short silica gel column, washed with ethylacetate/hexanes (¼). The combined organic solvents were evaporated to dryness under reduced pressure. The resulting residue was purified by column chromatography (hexanes:ethylacetate 30:1) to afford 3.76 g of the title compound. Yield: 99%. $^1$H NMR (300 MHz, CDCl$_3$) δ 1.47-1.73 (m, 8H), 1.91 (m, 4H), 2.63 (t, J=7.8 Hz, 4H), 3.42 (t, J=6.9 Hz, 4H), 7.15 (s, 4H) ppm; $^{13}$C NMR (75 MHz, CDCl$_3$) δ 28.5, 30.6, 32.7, 32.9, 34.0, 126.0, 129.2, 139.9 ppm.

Example 34

Synthesis of Compound
1,2-bis-[5-(2-methyl-pyridinium)-pentyl]-benzene dibromide

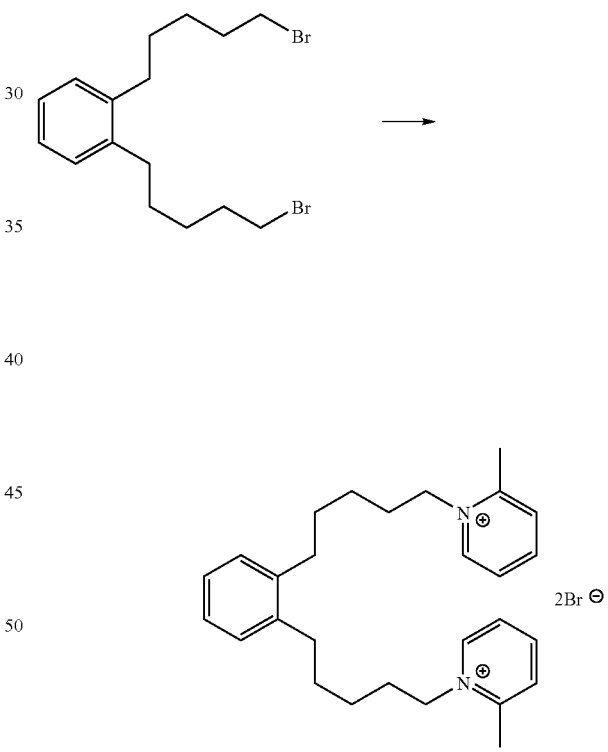

A mixture of 1,2-bis-(5-bromo-pentyl)-benzene (280 mg, 0.74 mmol) and 2-picoline (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 400 mg of the title compound. Yield: 95%. $^1$H NMR (300 MHz, CD$_3$OD) δ 1.54 (m, 4H), 1.68 (m, 4H), 2.01 (m, 4H), 2.69 (t, J=7.5 Hz, 4H), 2.90 (s, 6H), 4.61 (t, J=7.8 Hz, 4H), 7.02-7.19 (m, 4H), 7.92 (t, J=6.6 Hz, 2H), 8.00 (d, J=7.8 Hz, 2H), 8.44 (dt, J=7.8, 1.2 Hz, 2H), 8.93 (dd, J=6.3, 1.2 Hz, 2H) ppm; $^{13}$C NMR (75 MHz, CD$_3$OD) δ 20.8, 27.4, 31.2, 32.0, 33.4, 59.3, 126.9, 127.0, 130.3, 131.5, 141.0, 146.3, 146.4, 156.6 ppm.

Example 35

Synthesis of Compound 1,2-bis-[5-(3-methyl-pyridinium)-pentyl]-benzene dibromide

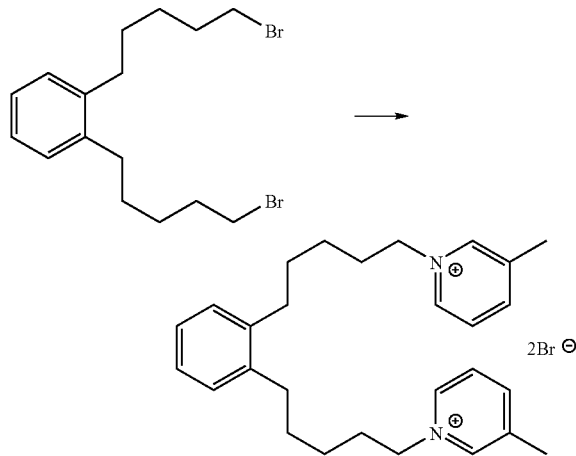

A mixture of 1,2-bis-(5-bromo-pentyl)-benzene (296 mg, 0.79 mmol) and 3-picoline (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 382 mg of the title compound. Yield: 86%. $^1$H NMR (300 MHz, CD$_3$OD) δ 1.47 (m, 4H), 1.66 (m, 4H), 2.08 (m, 4H), 2.59 (s, 6H), 2.65 (t, J=7.5 Hz, 4H), 4.64 (t, J=7.5 Hz, 4H), 7.01-7.19 (m, 4H), 7.99 (d, J=7.5, 6.0 Hz, 2H), 8.43 (dd, J=8.1, 0.6 Hz, 2H), 8.86 (d, J=6.0 Hz, 2H), 8.96 (s, 2H) ppm; $^{13}$C NMR (75 MHz, CD$_3$OD) δ 18.7, 27.2, 32.0, 32.6, 33.5, 62.9, 127.1, 128.7, 130.3, 141.0, 141.2, 143.1, 145.5, 147.2 ppm.

Example 36

Synthesis of Compound 1,2-bis-[5-(4-methyl-pyridinium)-pentyl]-benzene dibromide

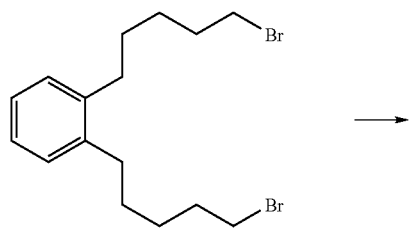

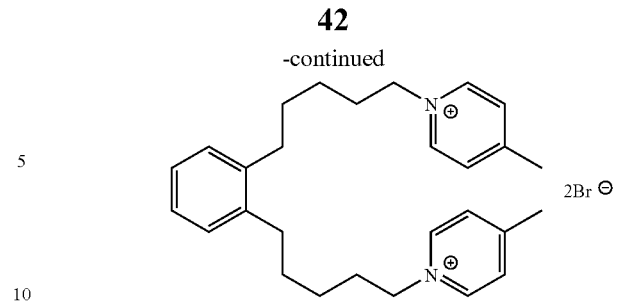

A mixture of 1,2-bis-(5-bromo-pentyl)-benzene (290 mg, 0.77 mmol) and 4-picoline (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 387 mg of the title compound. Yield: 89%. $^1$H NMR (300 MHz, CD$_3$OD) δ 1.44 (m, 4H), 1.65 (m, 4H), 2.04 (m, 4H), 2.64 (t, J=7.5 Hz, 4H), 2.68 (s, 6H), 4.58 (t, J=7.5 Hz, 4H), 7.02-7.15 (m, 4H), 7.92 (d, J=6.3 Hz, 4H), 8.83 (dd, J=5.1, 1.8 Hz, 4H) ppm; $^{13}$C NMR (75 MHz, CD$_3$OD) δ 22.3, 27.0, 31.9, 32.3, 33.3, 62.0, 127.0, 129.8, 130.2, 140.9, 144.7, 160.8 ppm.

Example 37

Synthesis of Compound 1,2-bis-[5-(2,4-dimethyl-pyridinium)-pentyl]-benzene dibromide

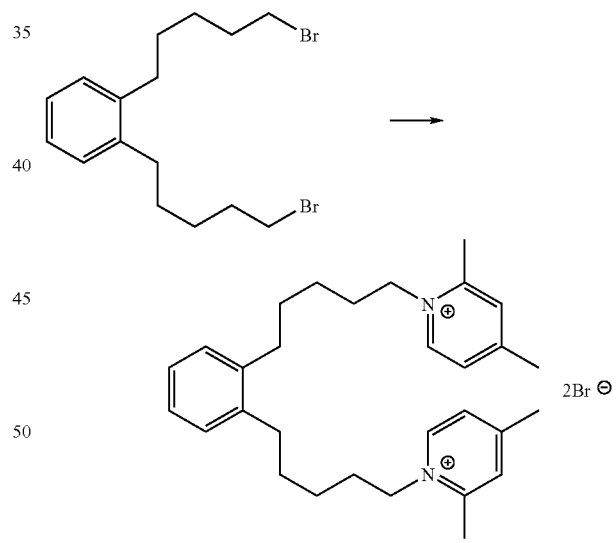

A mixture of 1,2-bis-(5-bromo-pentyl)-benzene (270 mg, 0.72 mmol) and 2,4-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 355 mg of the title compound. Yield: 84%. $^1$H NMR (300 MHz, CD$_3$OD) δ 1.52 (m, 4H), 1.68 (m, 4H), 2.01 (m, 4H), 2.61 (s, 6H), 2.68 (t, J=7.5 Hz, 4H), 2.82 (s, 6H), 4.53 (t, J=7.8 Hz, 4H), 7.02-7.19 (m, 4H), 7.73 (dd, J=6.3, 1.2 Hz, 2H), 7.82 (d, J=1.5 Hz, 2H), 8.72 (d, J=6.3 Hz, 2H) ppm; $^{13}$C NMR (75 MHz, CD$_3$OD) δ 20.5, 22.0, 27.4, 31.2, 32.0, 33.4, 58.4, 127.0, 127.6, 130.3, 131.6, 141.0, 145.4, 155.2, 160.2 ppm.

Example 38

Synthesis of Compound 1,2-bis-[5-(3,4-dimethyl-pyridinium)-pentyl]-benzene dibromide

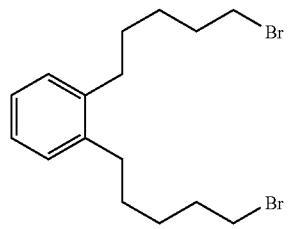

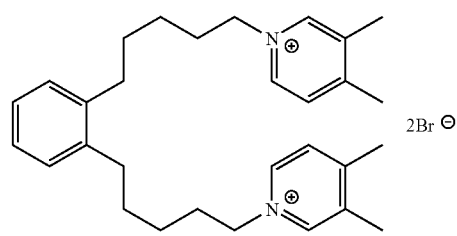

A mixture of 1,2-bis-(5-bromo-pentyl)-benzene (270 mg, 0.72 mmol) and 3,4-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 329 mg of the title compound. Yield: 78%. $^1$H NMR (300 MHz, CD$_3$OD) δ 1.43 (m, 4H), 1.65 (m, 4H), 2.03 (m, 4H), 2.48 (s, 6H), 2.59 (s, 6H), 2.64 (t, J=7.5 Hz, 4H), 4.54 (t, J=7.5 Hz, 4H), 7.02-7.17 (m, 4H), 7.85 (d, J=6.3 Hz, 2H), 8.67 (d, J=4.8 Hz, 2H), 8.77 (s, 2H) ppm; $^{13}$C NMR (75 MHz, CD$_3$OD) δ 17.3, 20.6, 27.1, 31.9, 32.4, 33.3, 61.8, 126.9, 129.4, 130.2, 139.7, 140.9, 142.4, 144.0, 159.5 ppm.

Example 39

Synthesis of Compound 1,2-bis-[5-(3,5-dimethyl-pyridinium)-pentyl]-benzene dibromide

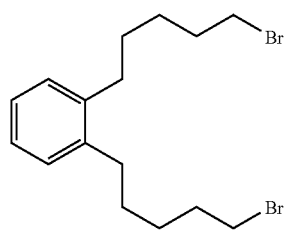

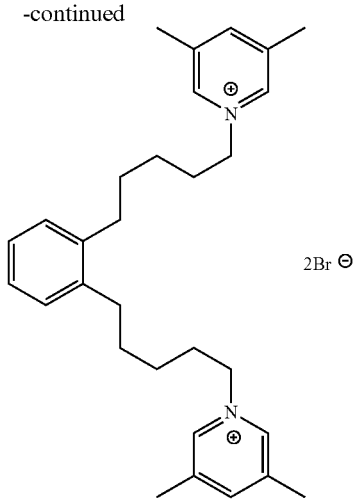

A mixture of 1,2-bis-(5-bromo-pentyl)-benzene (290 mg, 0.77 mmol) and 3,5-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 321 mg of the title compound. Yield: 71%. $^1$H NMR (300 MHz, CD$_3$OD) δ 1.50 (m, 4H), 1.65 (m, 4H), 2.12 (m, 4H), 2.58 (s, 12H), 2.64 (t, J=6.3 Hz, 4H), 4.68 (t, J=7.5 Hz, 4H), 7.02-7.19 (m, 4H), 8.33 (s, 2H), 8.91 (s, 4H) ppm; $^{13}$C NMR (75 MHz, CD$_3$OD) δ 18.7, 27.2, 31.9, 32.5, 33.4, 62.5, 126.9, 130.2, 140.0, 140.9, 142.6, 147.7 ppm.

Example 40

Synthesis of Compound 1,2-bis-(5-quinolinium-pentyl)-benzene dibromide

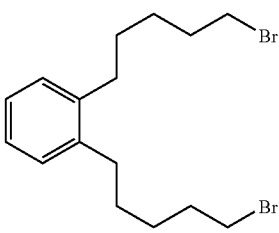

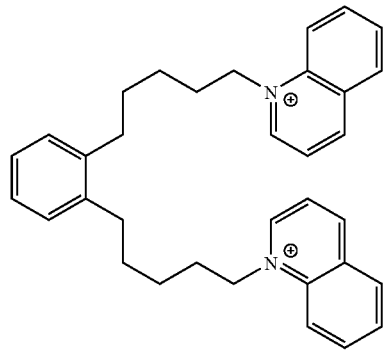

A mixture of 1,2-bis-(5-bromo-pentyl)-benzene (282 mg, 0.75 mmol) and quinoline (1 mL) was heated at 60-70° C. for 12 hrs. The resulted mixture was washed with diethyl ether and then dissolved in water (20 mL), the aqueous solution was extracted with chloroform (20 mL×3). Water was removed by lyophilization to afford 411 mg of the title compound. Yield: 86%. $^1$H NMR (300 MHz, CD$_3$OD) δ 1.41-1.73 (m, 8H), 2.13 (m, 4H), 2.47 (t, J=6.6 Hz, 4H), 5.22 (t, J=7.5 Hz, 4H), 6.91 (m, 4H), 8.00 (t, J=7.8 Hz, 2H), 8.16 (m, 2H), 8.31 (t, J=7.2 Hz, 2H), 8.44 (d, J=7.8 Hz, 2H), 8.65 (d, J=8.7 Hz, 2H), 9.30 (d, J=8.1 Hz, 2H), 9.70 (d, J=5.4 Hz, 2H) ppm; $^{13}$C NMR (75 MHz, CD$_3$OD) δ 27.3, 30.9, 31.6, 33.1, 59.2, 119.8, 123.0, 126.7, 129.8, 131.0, 131.1, 131.8, 137.1, 138.6, 140.6, 148.6, 150.2 ppm.

Example 41

Synthesis of Compound
1,2-bis-(5-isoquinolinium-pentyl)-benzene dibromide

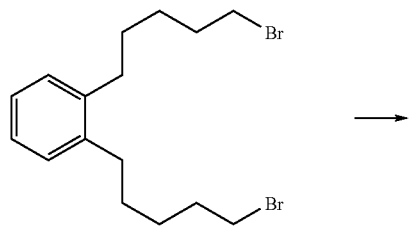

A mixture of 1,2-bis-(5-bromo-pentyl)-benzene (271 mg, 0.72 mmol) and isoquinoline (1 mL) was heated at 60-70° C. for 12 hrs. The resulted mixture was washed with diethyl ether and then dissolved in water (20 mL), the aqueous solution was extracted with chloroform (20 mL×3). Water was removed by lyophilization to afford 392 mg of the title compound. Yield: 86%. $^1$H NMR (300 MHz, CD$_3$OD) δ 1.38-1.70 (m, 8H), 2.20 (m, 4H), 2.52 (t, J=7.2 Hz, 4H), 4.92 (t, J=7.5 Hz, 4H), 6.83-7.05 (m, 4H), 7.99 (dd, J=6.9, 1.2 Hz, 2H), 8.18 (dt, J=8.1, 0.9, 2H), 8.28 (d, J=8.4 Hz, 2H), 8.45-8.60 (m, 4H), 8.84 (dd, J=6.9, 1.2 Hz, 2H), 10.21 (s, 2H) ppm; $^{13}$C NMR (75 MHz, CD$_3$OD) δ 27.0, 31.6, 32.2, 33.1, 62.5, 126.7, 127.2, 128.2, 128.5, 129.9, 131.2, 132.2, 135.6, 137.9, 138.3, 140.6, 150.3 ppm.

Example 42

Synthesis of Compound
1,2-bis-[5-(2'-S-nicotinium-pentyl)]benzene dibromide

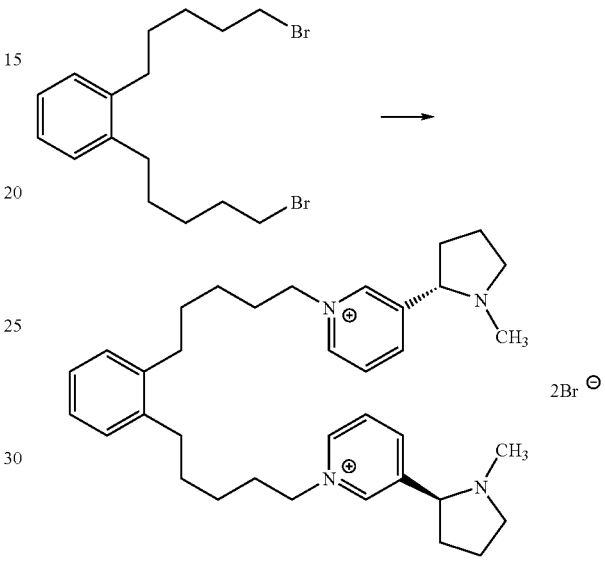

A mixture of 1,2-bis-(5-bromo-pentyl)-benzene (278 mg, 0.74 mmol) and S-nicotine (1 mL) was heated at 60-70° C. for 12 hrs. The resulted mixture was washed with diethyl ether and then dissolved in water (20 mL), the aqueous solution was extracted with chloroform (20 mL×3). Water was removed by lyophilization to afford 390 mg of the title compound. Yield: 75%. $^1$H NMR (300 MHz, CD$_3$OD) δ 1.40-1.75 (m, 8H), 2.08-2.45 (m, 10 H), 2.67 (s, 6H), 2.55-2.75 (m, 8H), 3.07 (m, 2H), 3.67 (m, 2H), 4.43 (t, J =6.9 Hz, 4H), 7.02-7.22 (m, 4H), 8.24 (dd, J=7.8, 6.3 Hz, 2H), 8.85 (d, J=8.1 Hz, 2H), 9.17 (d, J=6.0 Hz, 2H), 9.39 (s, 2H) ppm; $^{13}$C NMR (75 MHz, CD$_3$OD) δ 23.4, 27.1, 31.8, 32.2, 33.2, 33.7, 40.2, 57.6, 63.2, 68.9, 126.9, 129.6, 130.2, 139.8, 140.9, 145.8, 146.4 ppm.

Example 43

Synthesis of Compound
1,2-bis-[5-(3-n-butyl-pyridinium)-pentyl]-benzene dibromide

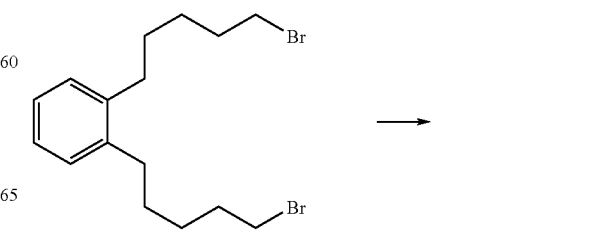

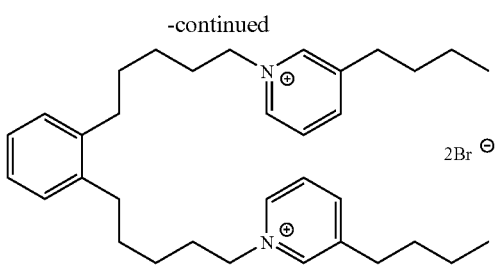

A mixture of 1,2-bis-(5-bromo-pentyl)-benzene (232 mg, 0.62 mmol) and 4-n-butylpyridine (0.5 mL) was heated at 60-70° C. for 12 hrs. The resulted mixture was washed with diethyl ether and then dissolved in water (20 mL), the aqueous solution was extracted with chloroform (20 mL×3). Water was removed by lyophilization to afford 154 mg of the title compound. Yield: 39%. $^1$H NMR (300 MHz, CD$_3$OD) δ 0.98 (t, J=7.2 Hz, 6H), 1.30-1.87 (m, 16H), 2.09 (m, 4H), 2.64 (t, J=7.5 Hz, 4H), 2.92 (t, J=7.2 Hz, 4H), 4.70 (t, J=6.6 Hz, 4H), 6.98-7.18 (m, 4H), 8.05 (dd, J=8.1, 5.4 Hz, 2H), 8.49 (d, J=8.1 Hz, 2H), 9.95 (d, J=5.7 Hz, 2H), 10.08 (s, 2H) ppm; $^{13}$C NMR (75 MHz, CD$_3$OD) δ 14.4, 23.3, 27.2, 31.9, 32.6, 33.3, 33.4, 33.8, 62.8, 127.0, 128.9, 130.3, 140.9, 143.3, 145.2, 145.5, 146.5 ppm.

Example 44

Synthesis of Compound 1,2-bis-[5-(3-bromo-pyridinium)-pentyl]-benzene dibromide

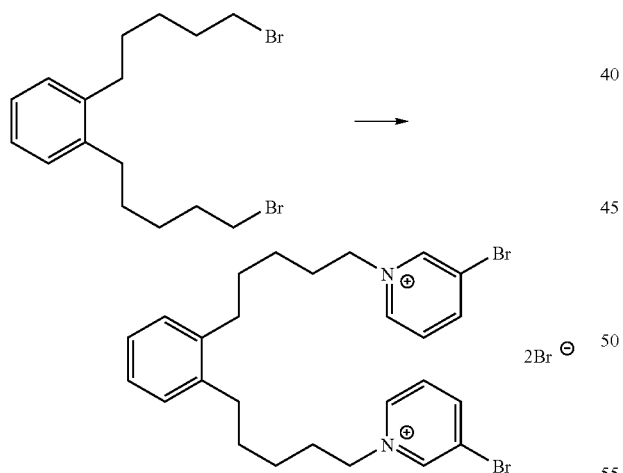

A mixture of 1,2-bis-(5-bromo-pentyl)-benzene (235 mg, 0.72 mmol) and 3-bromopyridine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 410 mg of the title compound. Yield: 95%. $^1$H NMR (300 MHz, CD$_3$OD) δ 1.30-1.75 (m, 8H), 2.13 (m, 4H), 2.63 (t, J=7.5 Hz, 4H), 4.79 (t, J=7.5 Hz, 4H), 7.00-7.21 (m, 4H), 8.12 (dd, J=8.1, 6.0 Hz, 2H), 8.84 (d, J=7.8 Hz, 2H), 9.24 (d, J=5.7 Hz, 2H), 9.58 (s, 2H) ppm; $^{13}$C NMR (75 MHz, CD$_3$OD) δ 27.2, 31.9, 32.5, 33.4, 63.2, 124.0, 127.0, 130.2, 140.9, 144.9, 147.1, 149.4 ppm.

Example 45

Synthesis of Compound 1,2-bis-(5-pyridinium-pentyl)-benzene dibromide

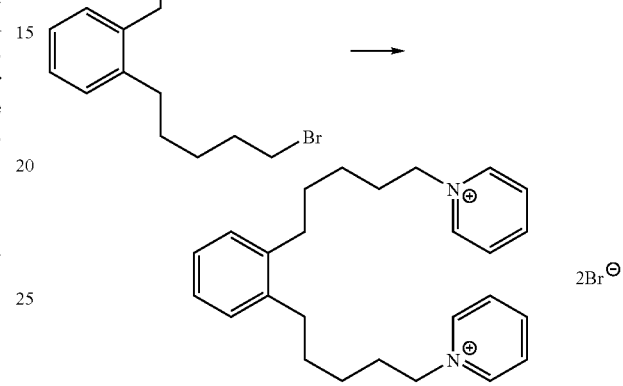

A mixture of 1,2-bis-(5-bromo-pentyl)-benzene (244 mg, 0.65 mmol) and pyridine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 317 mg of the title compound. Yield: 92%. $^1$H NMR (300 MHz, CD$_3$OD) δ 1.48 (m, 4H), 1.65 (m, 4H), 2.10 (m, 4H), 2.63 (t, J=7.5 Hz, 4H), 4.74 (t, J=7.5 Hz, 4H), 7.02-7.20 (m, 4H), 8.16 (t, J=6.9 Hz, 4H), 8.64 (t, J=7.8 Hz, 2H), 9.13 (d, J=5.4 Hz, 4H) ppm; $^{13}$C NMR (75 MHz, CD$_3$OD) δ 27.1, 31.9, 32.5, 33.3, 62.9, 127.0, 129.4, 130.3, 140.9, 145.8, 146.7 ppm.

Example 46

Synthesis of Compound 5-[3-(5-hydroxy-pent-1-ynyl)-phenyl]-pent-4-yn-1-ol

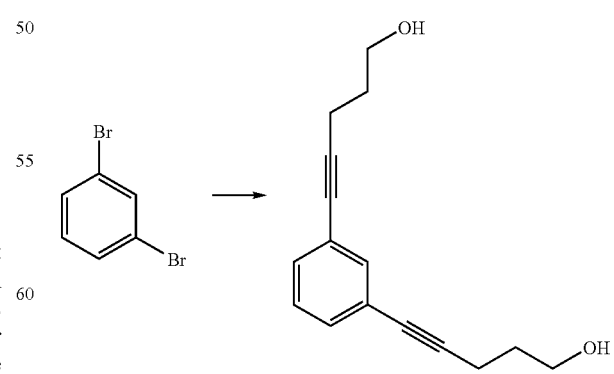

1,3-Dibromobenzene (7.48 g, 31.71 mmol), 4-pentyn-1-ol (6.40 g, 76.10 mmol), and bis(triphenylphosphine)palladium (II) dichloride (445 mg, 0.63 mmol) was stirred in triethylamine (150 mL) under nitrogen for 5 min. Copper(I) iodide (61 mg, 0.32 mmol) was added and the mixture was stirred for 18 hrs at 75° C. The mixture was cooled to room temperature and filtered through a celite pad, rinsed with ethylacetate. The combined filtrate was evaporated to dryness under reduced pressure. The resulting residue was purified by column chromatography (chloroform:methanol 20:1) to afford 7.24 g of the title compound. Yield: 94%. $^1$H NMR (300 MHz, CDCl$_3$) δ 1.85 (m, 4H), 2.53 (t, J=6.9 Hz, 4H), 3.81 (t, J=6.0 Hz, 4H), 7.16-7.31 (m, 3H), 7.42 (t, J=1.2 Hz, 1H) ppm; $^{13}$C NMR (75 MHz, CDCl$_3$) δ 16.2, 31.6, 61.9, 80.6, 90.0, 124.0, 128.3, 130.8, 134.7 ppm.

Example 47

Synthesis of Compound 1,3-bis-(5-bromo-pent-1-ynyl)-benzene

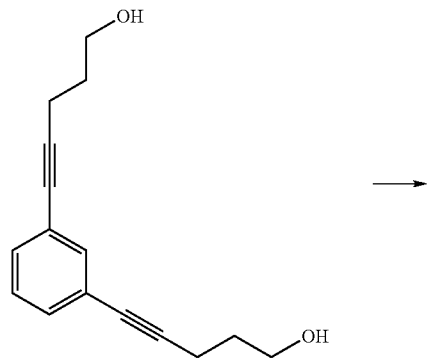

5-[3-(5-Hydroxy-pent-1-ynyl)-phenyl]-pent-4-yn-1-ol (2.86 g, 11.80 mmol) and carbon tetrabromide (9.78 g, 29.50 mmol) were dissolved in dry methylene chloride (30 mL) and cooled to 0° C. Triphenyl phosphine (8.13 g, 30.98 mmol) in methylene chloride (20 mL) was added dropwise and the mixture was stirred for 1 h at 0° C. The mixture was poured into hexanes (200 mL) and then filtered through a short silica gel column, washed with ethylacetate/hexanes (¼). The combined organic solvents were evaporated to dryness under reduced pressure. The resulting residue was purified by column chromatography (hexanes:ethylacetate 30:1) to afford 3.64 g of the title compound. Yield: 84%. $^1$H NMR (300 MHz, CDCl$_3$) δ 2.13 (m, 4H), 2.60 (t, J=6.6 Hz, 4H), 3.58 (dt, J=6.6 Hz, 4H), 7.18-7.32 (m, 3H), 7.43 (t, J=1.5 Hz, 1H) ppm; $^{13}$C NMR (75 MHz, CDCl$_3$) δ 18.4, 31.7, 32.7, 81.1, 88.7, 123.8, 128.4, 131.0, 134.8 ppm.

Example 48

Synthesis of Compound 1,3-bis-[5-(2-methyl-pyridinium)-pent-1-ynyl]-benzene dibromide

A mixture of 1,3-bis-(5-bromo-pent-1-ynyl)-benzene (368 mg, 1.00 mmol) and 2-picoline (1.5 mL) was heated at 60-70° C. for 12 hrs. The resulted mixture was washed with diethyl ether and then dissolved in water (20 mL), the aqueous solution was extracted with diethyl ether (30 mL×3). Water was removed by lyophilization to afford 472 mg of the title compound. Yield: 84%. $^1$H NMR (300 MHz, CD$_3$OD) δ 2.29 (m, 4H), 2.69 (t, J=6.6 Hz, 4H), 2.97 (s, 6H), 4.81 (t, J=7.5 Hz, 4H), 7.23-7.38 (m, 3H), 7.43 (d, J=1.5 Hz, 1H), 7.95 (t, J=6.9 Hz, 2H), 8.01 (d, J=7.8 Hz, 2H), 8.43 (dt, J=7.8, 1.5 Hz, 2H), 8.99 (dd, J=6.3, 1.5 Hz, 2H) ppm; $^{13}$C NMR (75 MHz, CD$_3$OD) δ 17.4, 20.9, 29.9, 58.3, 82.1, 89.6, 124.7, 127.0, 129.8, 131.5, 132.2, 135.2, 146.5, 146.6, 156.8 ppm.

Example 49

Synthesis of Compound 1,3-bis-[5-(3-methyl-pyridinium)-pent-1-ynyl]-benzene dibromide

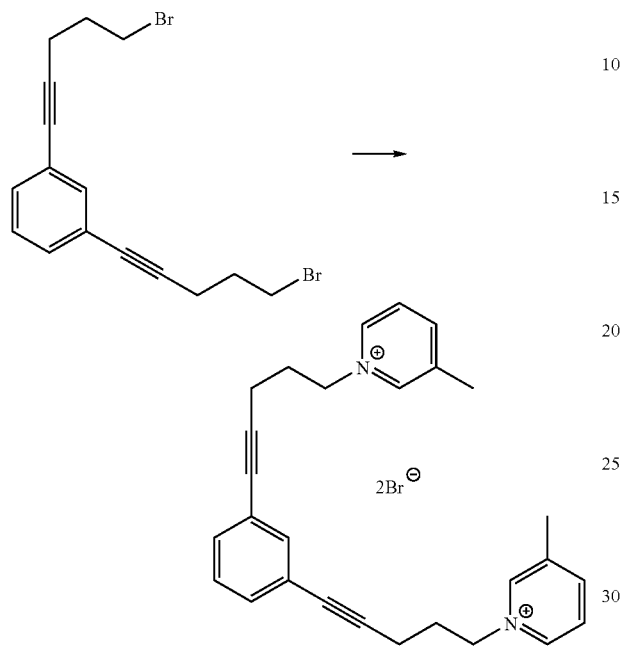

A mixture of 1,3-bis-(5-bromo-pent-1-ynyl)-benzene (348 mg, 0.94 mmol) and 3-picoline (1.5 mL) was heated at 60-70° C. for 12 hrs. The resulted mixture was washed with diethyl ether and then dissolved in water (20 mL), the aqueous solution was extracted with diethyl ether (30 mL×3). Water was removed by lyophilization to afford 469 mg of the title compound. Yield: 90%. $^1$H NMR (300 MHz, CD$_3$OD) δ 2.35 (m, 4H), 2.56 (s, 6H) 2.63 (t, J=6.6 Hz, 4H), 4.80 (t, J=7.2 Hz, 4H), 7.22-7.33 (m, 3H), 7.37 (s, 1H), 8.00 (dd, J=8.1, 6.3 Hz, 2H), 8.39 (d, J=7.8 Hz, 2H), 8.91 (d, J=6.3 Hz, 2H), 9.00 (s, 2H) ppm; $^{13}$C NMR (75 MHz, CD$_3$OD) δ 17.3, 18.8, 31.0, 62.1, 82.1, 89.4, 124.7, 128.7, 129.7, 132.1, 135.4, 141.1, 143.3, 145.7, 147.4 ppm.

Example 50

Synthesis of Compound 1,3-bis-[5-(4-methyl-pyridinium)-pent-1-ynyl]-benzene dibromide

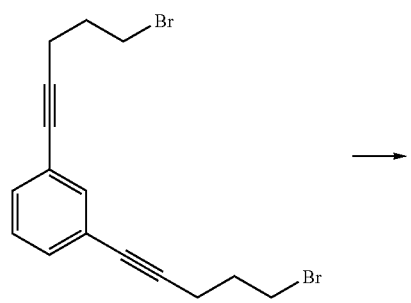

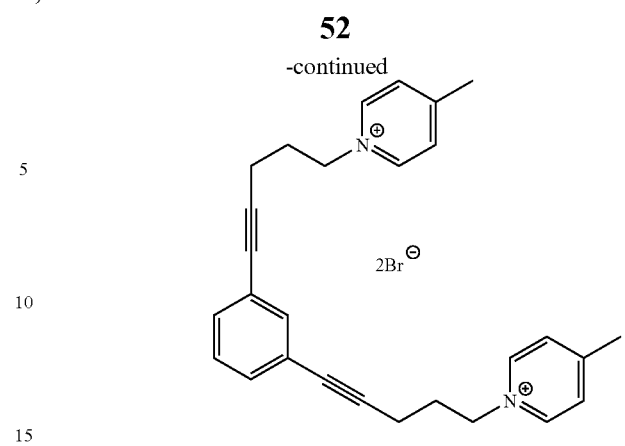

A mixture of 1,3-bis-(5-bromo-pent-1-ynyl)-benzene (350 mg, 0.94 mmol) and 4-picoline (1.5 mL) was heated at 60-70° C. for 12 hrs. The resulted mixture was washed with diethyl ether and then dissolved in water (20 mL), the aqueous solution was extracted with diethyl ether (30 mL×3). Water was removed by lyophilization to afford 478 mg of the title compound. Yield: 92%. $^1$H NMR (300 MHz, CD$_3$OD) δ 2.33 (m, 4H), 2.58 (s, 6H), 2.63 (t, J=6.6 Hz, 4H), 4.77 (t, J=6.9 Hz, 4H), 7.28 (s, 4H), 7.93 (d, J=6.3 Hz, 4H), 8.90 (d, J=6.6 Hz, 4H) ppm; $^{13}$C NMR (75 MHz, CD$_3$OD) δ 17.3, 22.3, 30.8, 61.4, 81.9, 89.5, 124.7, 129.9, 132.1, 135.2, 145.0, 161.2 ppm.

Example 51

Synthesis of Compound 1,3-bis-[5-(2,4-dimethyl-pyridinium)-pent-1-ynyl]-benzene dibromide

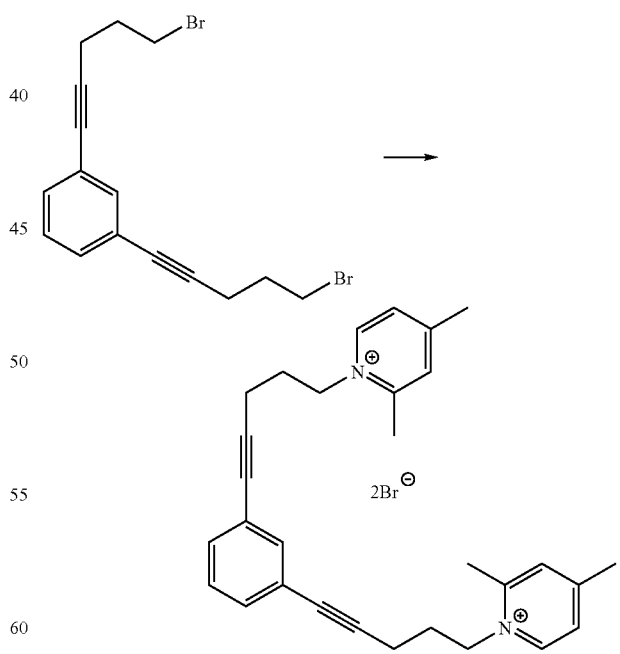

A mixture of 1,3-bis-(5-bromo-pent-1-ynyl)-benzene (249 mg, 0.68 mmol) and 2,4-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 357 mg of the title compound. Yield: 91%. $^1$H NMR (300 MHz, CD$_3$OD) δ 2.29 (m, 4H), 2.51 (s, 3H), 2.73 (t, J=6.6 Hz, 4H), 2.94 (s, 3H), 4.79 (t, J=7.5 Hz, 4H), 7.33 (d, J=0.9 Hz, 4H), 7.78 (dd, J=6.6, 2.1 Hz, 2H), 7.85 (s, 2H), 8.89 (d, J=6.6 Hz, 2H) ppm; $^{13}$C NMR (75 MHz, CD$_3$OD) δ 17.4, 20.6, 22.0, 29.9, 57.6, 82.0, 89.7, 124.8, 127.6, 129.9, 131.7, 132.1, 135.1, 145.6, 155.5, 160.5 ppm.

Example 52

Synthesis of Compound 1,3-bis-[5-(3,4-dimethyl-pyridinium)-pent-1-ynyl]-benzene dibromide

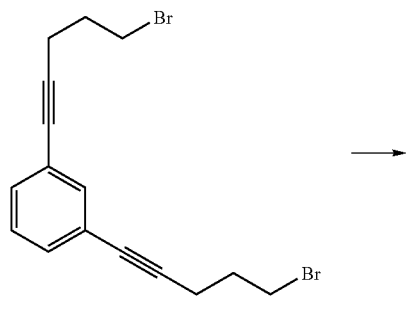

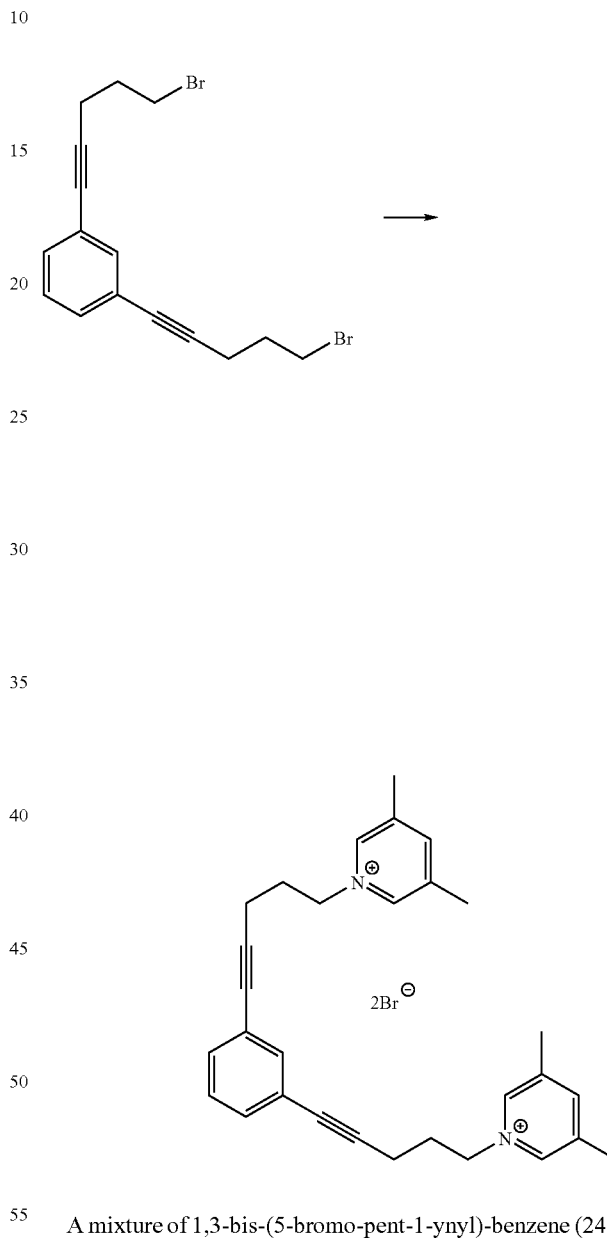

A mixture of 1,3-bis-(5-bromo-pent-1-ynyl)-benzene (253 mg, 0.69 mmol) and 3,4-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 261 mg of the title compound. Yield: 65%. $^1$H NMR (300 MHz, CD$_3$OD) δ 2.36 (s, 3H), 2.43 (s, 3H), 2.47 (m, 4H), 2.66 (t, J=6.6 Hz, 4H), 4.77 (t, J=6.9 Hz, 4H), 7.18-7.36 (m, 4H), 7.87 (d, J=6.3 Hz, 2H), 8.82 (d, J=6.3 Hz, 2H), 8.92 (s, 2H), ppm; $^{13}$C NMR (75 MHz, CD$_3$OD) δ 17.2, 17.4, 20.4, 30.8, 61.5, 81.9, 89.5, 124.9, 129.5, 129.8, 132.0, 135.3, 139.8, 142.9, 144.5, 160.0 ppm.

Example 53

Synthesis of Compound 1,3-bis-[5-(3,5-dimethyl-pyridinium)-pent-1-ynyl]-benzene dibromide A mixture of 1,3-bis-(5-bromo-pent-1-ynyl)-benzene (249 mg, 0.68 mmol) and 3,5-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 356 mg of the title compound. Yield: 90%. $^1$H NMR (300 MHz, CD$_3$OD) δ 2.35 (m, 4H), 2.51 (s, 6H), 2.64 (t, J=6.3 Hz, 4H), 4.75 (t, J=7.2 Hz, 4H), 7.28 (d, J=1.2 Hz, 3H), 7.33 (s, 1H), 8.19 (s, 2H), 8.82 (s, 4H) ppm; $^{13}$C NMR (75 MHz, CD$_3$OD) δ 17.4, 18.7, 31.0, 61.8, 81.9, 89.7, 124.6, 129.7, 132.0, 135.2, 140.1, 142.8, 147.9 ppm.

Example 54

Synthesis of Compound
1,3-bis-(5-quinolinium-pent-1-ynyl)-benzene
dibromide

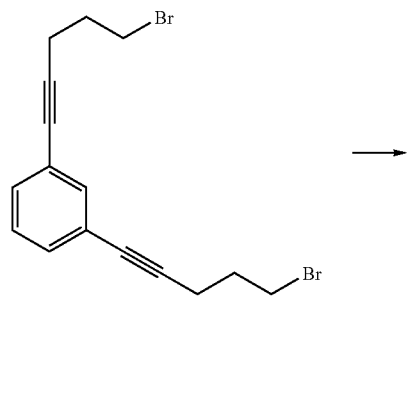

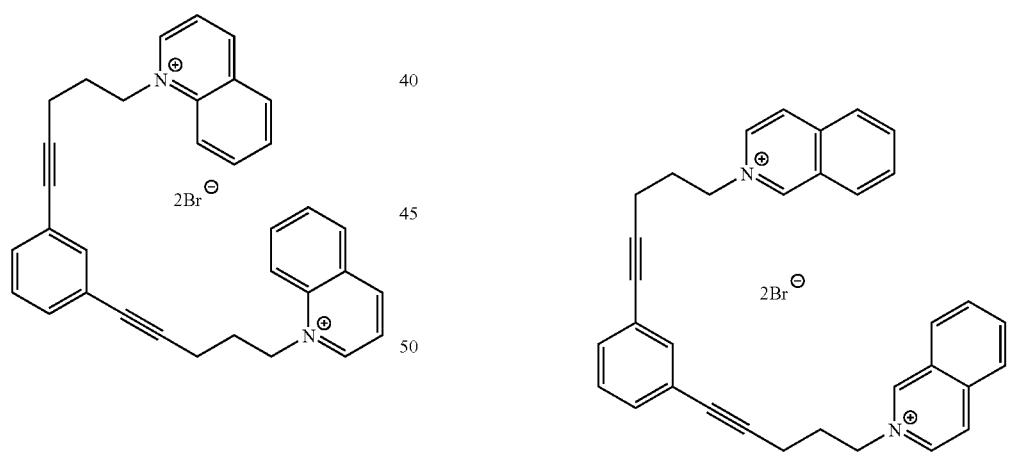

A mixture of 1,3-bis-(5-bromo-pent-1-ynyl)-benzene (253 mg, 0.69 mmol) and quinoline (1 mL) was heated at 60-70° C. for 12 hrs. The resulted mixture was washed with diethyl ether and then dissolved in water (30 mL), the aqueous solution was extracted with chloroform (20 mL×3). Water was removed by lyophilization to afford 271 mg of the title compound. Yield: 63%. $^1$H NMR (300 MHz, CD$_3$OD) δ 2.45 (m, 4H), 2.73 (t, J=6.6 Hz, 4H), 5.31 (t, J=7.5 Hz, 4H), 7.14 (d, J=1.2 Hz, 1H), 7.20-7.30 (m, 3H), 8.02-8.17 (m, 4H), 8.31 (dt, J=7.2, 1.2 Hz, 2H), 8.41 (dd, J=8.4, 1.5 Hz, 2H), 8.67 (d, J=9.0 Hz, 2H), 9.17 (d, J=8.7 Hz, 2H), 9.54 (dd, J=5.7, 1.5 Hz, 2H) ppm; $^{13}$C NMR (75 MHz, CD$_3$OD) δ 17.5, 29.6, 58.7, 81.8, 89.8, 119.7, 123.1, 124.4, 129.6, 131.2, 131.4, 131.9, 132.1, 135.0, 137.3, 139.1, 149.1, 150.6 ppm.

Example 55

Synthesis of Compound
1,3-bis-(5-isoquinolinium-pent-1-ynyl)-benzene
dibromide

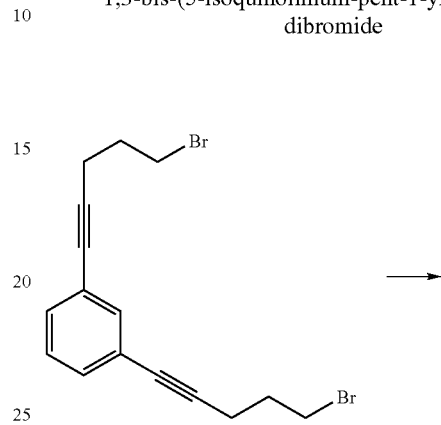

A mixture of 1,3-bis-(5-bromo-pent-1-ynyl)-benzene (257 mg, 0.70 mmol) and isoquinoline (1 mL) was heated at 60-70° C. for 12 hrs. The resulted mixture was washed with diethyl ether and then dissolved in water (30 mL), the aqueous solution was extracted with chloroform (20 mL×3). Water was removed by lyophilization to afford 316 mg of the title compound. Yield: 72%. $^1$H NMR (300 MHz, CD$_3$OD) δ 2.47 (m, 4H), 2.74 (t, J=6.3 Hz, 4H), 5.01 (t, J=6.9 Hz, 4H), 6.54 (s, 1H), 6.85-7.03 (m, 3H), 8.01 (dt, J=6.0, 1.5 Hz, 2H), 8.11-8.22 (m, 4H), 8.40-8.57 (m, 4H), 8.79 (dd, J=6.9, 1.2 Hz, 2H), 10.15 (s, 2H) ppm; $^{13}$C NMR (75 MHz, CD$_3$OD) δ 17.6, 30.6, 62.6, 82.0, 89.2, 124.4, 127.5, 128.4, 129.2, 129.3, 131.5, 131.7, 132.5, 134.7, 136.0, 138.4, 139.1, 151.5 ppm.

Example 56

Synthesis of Compound 1,3-bis-[5(2'-S-nicotinium-pent-1-ynyl)]benzene dibromide

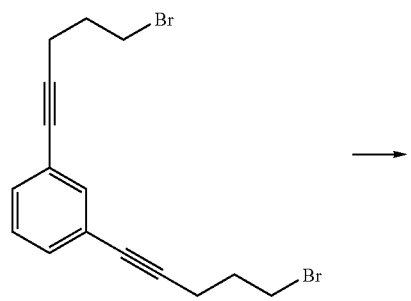

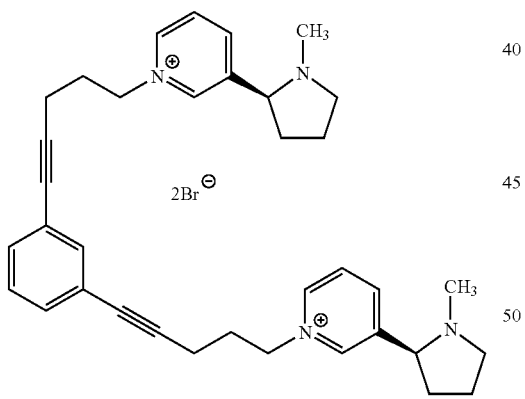

A mixture of 1,3-bis-(5-bromo-pent-1-ynyl)-benzene (244 mg, 0.66 mmol) and S-nicotine (1 mL) was heated at 60-70° C. for 12 hrs. The resulted mixture was washed with diethyl ether and then dissolved in water (20 mL), the aqueous solution was extracted with chloroform (20 mL×3). Water was removed by lyophilization to afford 388 mg of the title compound. Yield: 85%. $^1$H NMR (300 MHz, CD$_3$OD) δ 1.75-2.15 (m, 6 H), 2.35 (s, 6H), 2.33-2.50 (m, 6H), 2.63 (t, J=6.6 Hz, 4H), 3.37 (m, 2H), 3.74 (m, 2H), 4.87 (t, J=6.9 Hz, 4H), 7.23-7.35 (m, 3H), 7.41 (s, 1H), 8.12 (dd, J=8.1, 6.0 Hz, 2H), 8.61 (dd, J=7.8, 0.9 Hz, 2H), 9.03 (dd, J=6.0, 0.9 Hz, 2H), 9.18 (s, 2H) ppm; $^{13}$C NMR (75 MHz, CD$_3$OD) δ 17.2, 23.9, 30.8, 35.5, 40.7, 57.8, 62.3, 68.5, 82.2, 89.3, 124.7, 129.4, 129.7, 132.2, 135.4, 144.9, 145.1, 145.4, 146.1 ppm.

Example 57

Synthesis of compound 1,3-bis-[5-(3-n-butyl-pyridinium)-pent-1-ynyl]-benzene dibromide

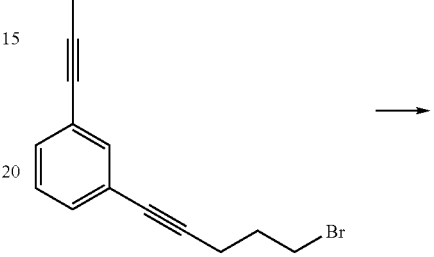

A mixture of 1,3-bis-(5-bromo-pent-1-ynyl)-benzene (242 mg, 0.66 mmol) and 4-n-butylpyridine (0.5 mL) was heated at 60-70° C. for 12 hrs. The resulted mixture was washed with diethyl ether and then dissolved in water (30 mL), the aqueous solution was extracted with chloroform (20 mL×3). Water was removed by lyophilization to afford 347 mg of the title compound. Yield: 83%. $^1$H NMR (300 MHz, CD$_3$OD) δ 0.98 (t, J=7.2 Hz, 6H), 0.95 (t, J=7.2 Hz, 6H), 1.40 (m, 4H), 1.67 (m, 4H), 2.39 (m, 4H), 2.67 (t, J=6.6 Hz, 4H), 2.88 (t, J=7.8 Hz, 4H), 4.90 (t, J=6.9 Hz, 4H), 7.29 (d, J=1.2 Hz, 3H), 7.33 (s, 1H), 8.07 (dd, J=7.8, 6.0 Hz, 2H), 8.45 (d, J=8.1 Hz, 2H), 9.04 (d, J=6.3 Hz, 2H), 9.14 (s, 2H) ppm; $^{13}$C NMR (75 MHz, CD$_3$OD) δ 14.4, 17.3, 23.3, 31.0, 33.3, 33.6, 62.1, 82.1, 89.4, 124.7, 129.0, 129.7, 132.2, 135.4, 143.5, 145.4, 145.5, 146.8 ppm.

Example 58

Synthesis of Compound 1,3-bis-[5-(3-phenyl-pyridinium)-pent-1-ynyl]-benzene dibromide

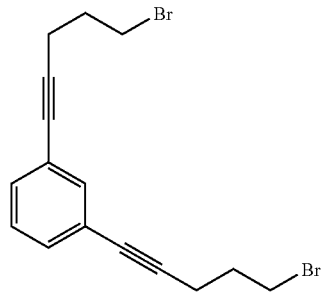

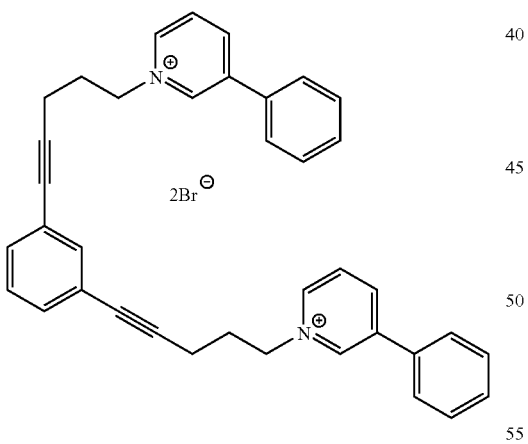

A mixture of 1,3-bis-(5-bromo-pent-1-ynyl)-benzene (243 mg, 0.66 mmol) and 3-bromopyridine (0.5 mL) was heated at 60-70° C. for 12 hrs. The resulted mixture was washed with diethyl ether and then dissolved in water (30 mL), the aqueous solution was extracted with chloroform (20 mL×3). Water was removed by lyophilization to afford 390 mg of the title compound. Yield: 87%. $^1$H NMR (300 MHz, CD$_3$OD) δ 2.41 (m, 4H), 2.70 (t, J=6.6 Hz, 4H), 5.00 (t, J=6.9 Hz, 4H), 7.15 (d, J=1.2 Hz, 1H), 7.18 (m, 3H), 7.45-7.58 (m, 6H), 7.77-7.87 (m, 4H), 8.14 (dd, J=8.1, 6.0 Hz, 2H), 8.74 (ddd, J=8.1, 1.5, 1.2 Hz, 2H), 9.13 (d, J=6.0 Hz, 2H), 9.56 (s, 2H) ppm; $^{13}$C NMR (75 MHz, CD$_3$OD) δ 17.4, 30.9, 62.4, 82.0, 89.5, 124.5, 128.6, 129.5, 129.6, 130.6, 131.4, 132.0, 134.1, 135.3, 142.1, 143.9, 144.0, 144.2 ppm.

Example 59

Synthesis of Compound 1,3-bis-(5-pyridinium-pent-1-ynyl)-benzene dibromide

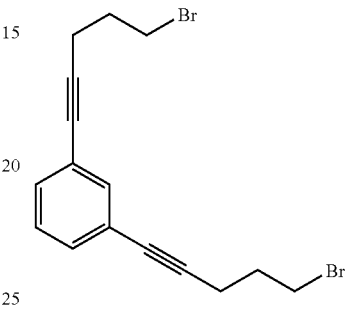

A mixture of 1,3-bis-(5-bromo-pent-1-ynyl)-benzene (240 mg, 0.65 mmol) and pyridine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 322 mg of the title compound. Yield: 94%. $^1$H NMR (300 MHz, CD$_3$OD) δ 2.40 (m, 4H), 2.68 (t, J=6.9 Hz, 4H), 4.94 (t, J=7.5 Hz, 4H), 7.32 (m, 3H), 7.39 (d, J=1.2 Hz, 1H), 8.19 (dd, J=7.8, 6.9 Hz, 4H), 8.63 (m, 2H), 9.23 (dd, J=7.2, 1.2 Hz, 4H) ppm; $^{13}$C NMR (75

MHz, CD$_3$OD) δ 17.2, 31.0, 62.1, 82.1, 89.4, 124.6, 129.4, 129.7, 132.2, 135.3, 146.0, 146.9 ppm.

Example 60

Synthesis of Compound
5-[3-(5-hydroxy-pentyl)-phenyl]-pentan-1-ol

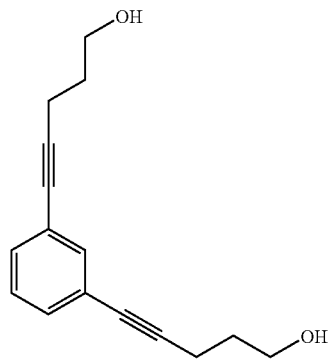

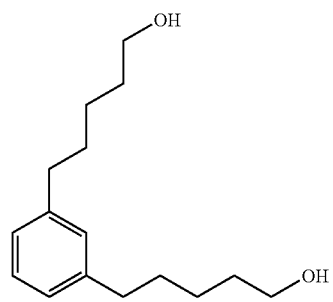

5-[3-(5-Hydroxy-pent-1-ynyl)-phenyl]-pent-4-yn-1-ol (3.40 g, 14.03 mmol) was dissolved in methanol (60 mL) and 10% Pd/C (2.5% w/w) was added. The resulting mixture was hydrogenated on a Parr hydrogenation apparatus (45 psi) for 12 hrs. The catalyst was removed by filtration through a Celite pad. The filter cake was rinsed with methanol, and the combined organic liquors were concentrated under reduced pressure. The crude product was purified by column chromatography (chloroform:methanol 20:1) to afford 3.12 g of the title compound. Yield: 89%. $^1$H NMR (300 MHz, CDCl$_3$) δ 1.30-1.45 (m, 4H), 1.50-1.72 (m, 8H), 2.59 (t, J=7.8 Hz, 4H), 3.62 (t, J=6.6 Hz, 4H), 6.99 (m, 3H), 7.18 (m, 1H) ppm; $^{13}$C NMR (75 MHz, CDCl$_3$) δ 25.7, 31.5, 32.8, 36.1, 63.0, 125.8, 128.3, 128.7, 142.5 ppm.

Example 61

Synthesis of Compound
1,3-bis-(5-bromo-pentyl)-benzene

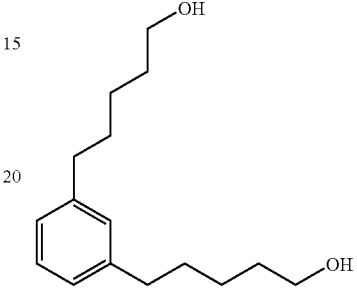

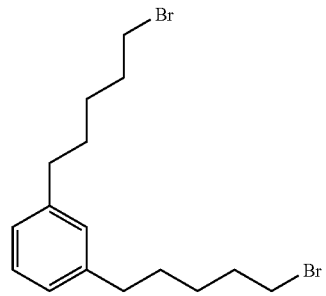

5-[3-(5-Hydroxy-pentyl)-phenyl]-pentan-1-ol (2.26 g, 9.03 mmol) and carbon tetrabromide (7.49 g, 22.58 mmol) were dissolved in dry methylene chloride (20 mL) and cooled to 0° C. Triphenyl phosphine (6.22 g, 23.70 mmol) in methylene chloride (15 mL) was added dropwise and the mixture was stirred for 1 h at 0° C. The mixture was poured into hexanes (200 mL) and then filtered through a short silica gel column, washed with ethylacetate/hexanes (¼). The combined organic solvents were evaporated to dryness under reduced pressure. The resulting residue was purified by column chromatography (hexanes:ethylacetate 30:1) to afford 2.80 g of the title compound. Yield: 82%. $^1$H NMR (300 MHz, CDCl$_3$) δ 1.46 (m, 4H), 1.61 (m, 4H), 1.88 (m, 4H), 2.59 (t, J=7.8 Hz, 4H), 3.40 (t, J=6.9 Hz, 4H), 7.00 (m, 3H), 7.19 (m, 1H) ppm; $^{13}$C NMR (75 MHz, CDCl$_3$) δ 28.1, 30.9, 32.9, 34.1, 36.0, 125.9, 128.3, 128.6, 142.4 ppm.

26.9, 31.0, 32.0, 36.5, 59.2, 126.85, 126.88, 129.3, 129.6, 131.4, 143.3, 146.2, 146.3, 156.4 ppm.

Example 62

Synthesis of Compound 1,3-bis-[5-(2-methyl-pyridinium)-pentyl]-benzene dibromide Example 63

Synthesis of Compound 1,3-bis-[5-(3-methyl-pyridinium)-pentyl]-benzene dibromide

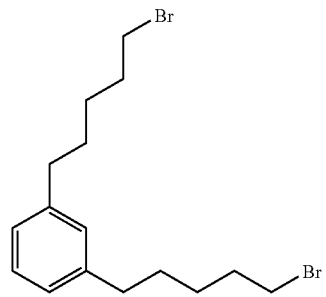  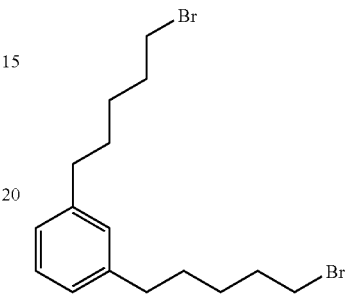

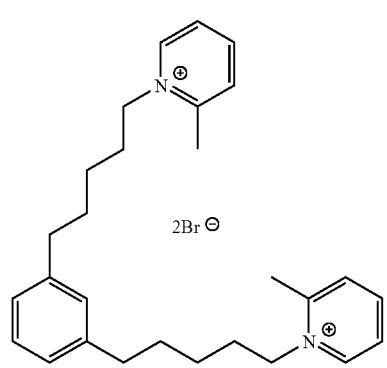 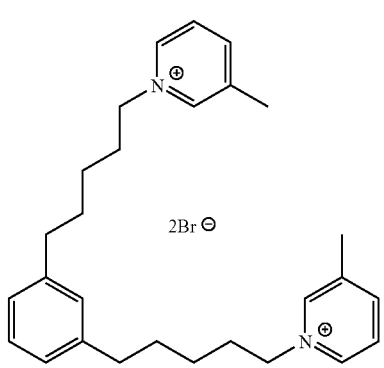

A mixture of 1,3-bis-(5-bromo-pentyl)-benzene (240 mg, 0.64 mmol) and 2-picoline (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 328 mg of the title compound. Yield: 91%. $^1$H NMR (300 MHz, CD$_3$OD) δ 1.54 (m, 4H), 1.73 (m, 4H), 2.02 (m, 4H), 2.63 (t, J=7.5 Hz, 4H), 2.95 (s, 6H), 4.67 (t, J=7.5 Hz, 4H), 6.98-7.22 (m, 4H), 7.97 (t, J=6.9 Hz, 2H), 8.07 (d, J=8.1 Hz, 2H), 8.49 (t, J=7.8 Hz, 2H), 9.05 (d, J=6.3 Hz, 2H) ppm; $^{13}$C NMR (75 MHz, CD$_3$OD) δ 20.9, A mixture of 1,3-bis-(5-bromo-pentyl)-benzene (265 mg, 0.70 mmol) and 3-picoline (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 362 mg of the title compound. Yield: 91%. $^1$H NMR (300 MHz, CD$_3$OD) δ 1.44 (m, 4H), 1.69 (m, 4H), 2.10 (m, 4H), 2.59 (t, J=7.8 Hz, 4H), 2.62 (s, 6H), 4.70 (t, J=7.5 Hz, 4H), 6.94-7.09 (m, 3H), 7.16 (t, J=1.5 Hz, 1H), 8.03 (dd, J=8.1, 6.0 Hz, 2H), 8.48 (d, J=8.1 Hz, 2H), 8.96 (d, J=6.0 Hz, 2H), 9.08 (s, 2H) ppm; $^{13}$C NMR (75 MHz, CD$_3$OD) δ 18.9, 26.6, 31.9, 32.3, 36.5, 62.6, 126.9, 128.6, 129.3, 129.6, 140.9, 142.9, 143.3, 145.3, 147.1 ppm.

$^{13}$C NMR (75 MHz, CD$_3$OD) δ 22.4, 26.6, 31.9, 32.2, 36.5, 61.9, 126.9, 129.3, 129.6, 129.8, 143.3, 144.7, 160.7 ppm.

Example 64

Synthesis of Compound 1,3-bis-[5-(4-methyl-pyridinium)-pentyl]-benzene dibromide

Example 65

Synthesis of Compound 1,3-bis-[5-(2,4-dimethyl-pyridinium)-pentyl]-benzene dibromide

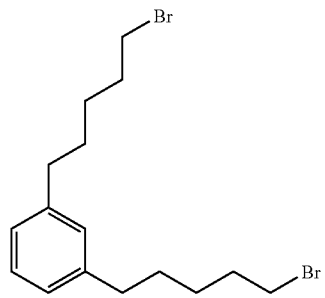
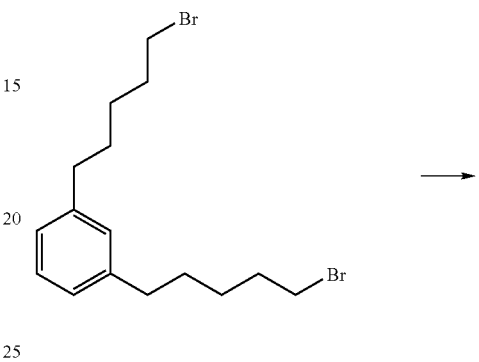

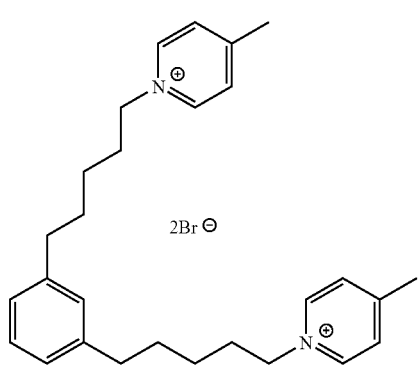
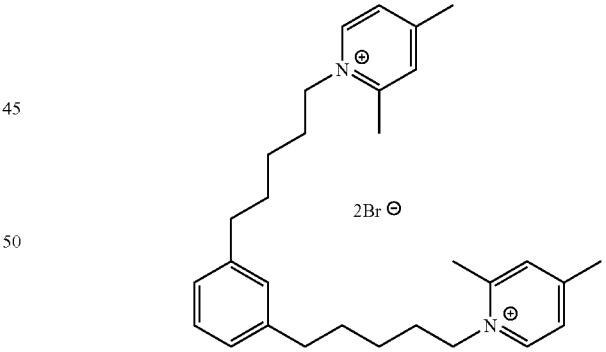

A mixture of 1,3-bis-(5-bromo-pentyl)-benzene (240 mg, 0.64 mmol) and 4-picoline (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 332 mg of the title compound. Yield: 92%. $^1$H NMR (300 MHz, CD$_3$OD) δ 1.42 (m, 4H), 1.67 (m, 4H), 2.06 (m, 4H), 2.59 (t, J=7.5 Hz, 4H), 2.69 (s, 6H), 4.66 (t, J=7.5 Hz, 4H), 6.95-7.08 (m, 3H), 7.16 (t, J=7.5 Hz, 1H), 7.97 (d, J=6.3 Hz, 4H), 8.94 (d, J=6.3 Hz, 4H) ppm;

A mixture of 1,3-bis-(5-bromo-pentyl)-benzene (237 mg, 0.63 mmol) and 2,4-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 323 mg of the title compound. Yield: 87%. $^1$H NMR (300 MHz, CD$_3$OD) δ 1.51 (m, 4H), 1.71 (m, 4H), 1.99 (m, 4H), 2.62 (t, J=7.5 Hz, 4H), 2.64 (s, 6H), 2.87 (s, 6H), 4.58 (t, J=7.5 Hz, 4H), 6.96-7.12 (m, 3H), 7.17 (t, J=7.5 Hz, 1H), 7.78 (dd, J=6.6, 1.5 Hz, 2H), 7.89 (d, J=1.5 Hz, 2H), 8.82 (d, J=6.6 Hz, 2H) ppm; $^{13}$C NMR (75

MHz, CD$_3$OD) δ 20.5, 22.1, 26.9, 31.1, 32.1, 36.6, 58.4, 126.9, 127.5, 129.3, 129.6, 131.6, 143.3, 145.3, 155.1, 160.1 ppm.

Example 66

Synthesis of Compound 1,3-bis-[5-(3,4dimethyl-pyridinium)-pentyl]-benzene dibromide

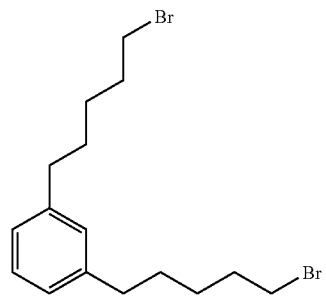
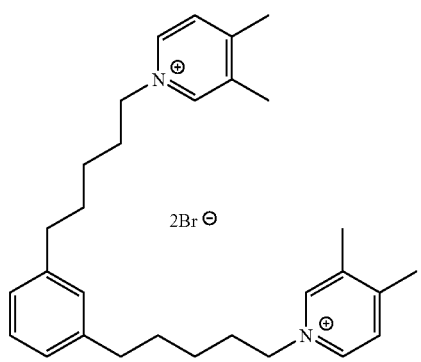

A mixture of 1,3-bis-(5-bromo-pentyl)-benzene (235 mg, 0.62 mmol) and 3,4-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 350 mg of the title compound. Yield: 97%. $^1$H NMR (300 MHz, CD$_3$OD) δ 1.44 (m, 4H), 1.68 (m, 4H), 2.09 (m, 4H), 2.51 (s, 6H), 2.59 (t, J=7.8 Hz, 4H), 2.60 (s, 6H), 4.65 (t, J=7.5 Hz, 4H), 6.96-7.20 (m, 4H), 7.92 (d, J=6.3 Hz, 2H), 8.82 (d, J=6.3 Hz, 2H), 8.96 (s, 2H) ppm; $^{13}$C NMR (75 MHz, CD$_3$OD) δ 17.3, 20.7, 26.6, 31.9, 32.2, 36.5, 61.7, 126.8, 129.2, 129.3, 129.5, 139.6, 142.3, 143.2, 143.9, 159.4 ppm.

Example 67

Synthesis of Compound 1,3-bis-[5-(3,5-dimethyl-pyridinium)-pentyl]-benzene dibromide

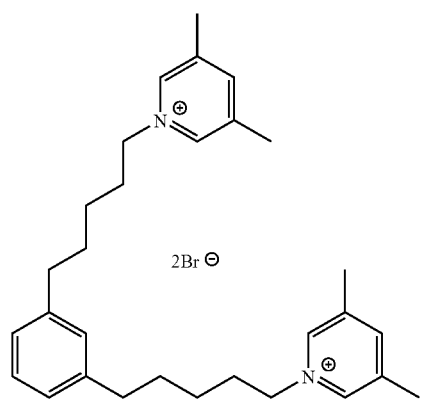

A mixture of 1,3-bis-(5-bromo-pentyl)-benzene (246 mg, 0.65 mmol) and 3,5-lutidine (1 mL) was heated at 60-70° C. for 12 hrs. The resulted mixture was washed with diethyl ether and then dissolved in water (15 mL), the aqueous solution was extracted with diethyl ether (30 mL×3). Water was removed by lyophilization to afford 371 mg of the title compound. Yield: 96%. $^1$H NMR (300 MHz, CD$_3$OD) δ 1.46 (m, 4H), 1.68 (m, 4H), 2.11 (m, 4H), 2.58 (s, 12H), 2.63 (t, J=6.6 Hz, 4H), 4.66 (t, J=7.5 Hz, 4H), 6.95-7.20 (m, 4H), 8.34 (s, 2H), 8.92 (s, 4H) ppm; $^{13}$C NMR (75 MHz, CD$_3$OD) δ 18.7, 26.7, 32.0, 32.4, 36.5, 62.3, 126.8, 129.2, 129.5, 140.0, 142.6, 143.3, 147.6 ppm.

Example 68

Synthesis of Compound 1,3-bis-(5-quinolinium-pentyl)-benzene dibromide

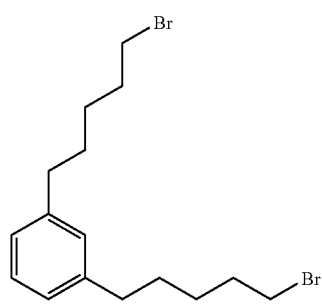

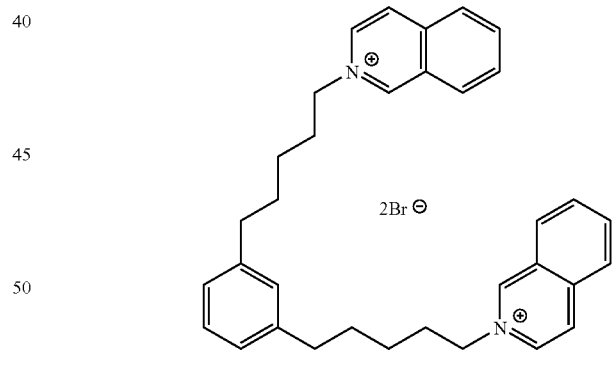

A mixture of 1,3-bis-(5-bromo-pentyl)-benzene (253 mg, 0.67 mmol) and quinoline (1 mL) was heated at 60-70° C. for 12 hrs. The resulted mixture was washed with diethyl ether and then dissolved in water (30 mL), the aqueous solution was extracted with chloroform (20 mL×3). Water was removed by lyophilization to afford 383 mg of the title compound. Yield: 90%. $^1$H NMR (300 MHz, CD$_3$OD) δ 1.52 (m, 4H), 1.64 (m, 4H), 2.13 (m, 4H), 2.51 (t, J=7.5 Hz, 4H), 5.17 (t, J=7.5 Hz, 4H), 6.81-7.06 (m, 4H), 8.03 (t, J=7.8 Hz, 2H), 8.12 (dd, J=8.4, 6.0 Hz, 2H), 8.31 (dt, J=6.0, 1.5 Hz, 2H), 8.45 (dd, J=8.4, 0.9 Hz, 2H), 8.61 (d, J=9.0 Hz, 2H), 9.27 (d, J=8.4 Hz, 2H), 9.59 (d, J=5.7 Hz, 2H) ppm; $^{13}$C NMR (75 MHz, CD$_3$OD) δ 27.0, 30.9, 31.9, 36.4, 59.3, 119.8, 123.0, 126.8, 129.1, 129.4, 131.2, 131.3, 132.0, 137.2, 138.9, 143.1, 148.7, 150.2 ppm.

Example 69

Synthesis of Compound 1,3-bis-(5-isoquinolinium-pentyl)-benzene dibromide

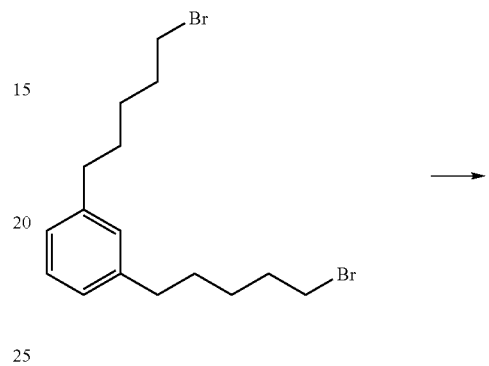

A mixture of 1,3-bis-(S-bromo-pentyl)-benzene (278 mg, 0.74 mmol) and isoquinoline (1 mL) was heated at 60-70° C. for 12 hrs. The resulted mixture was washed with diethyl ether and then dissolved in water (30 mL), the aqueous solution was extracted with chloroform (20 mL×3). Water was removed by lyophilization to afford 391 mg of the title compound. Yield: 83%. $^1$H NMR (300 MHz, CD$_3$OD) δ 1.43 (m, 4H), 1.64 (m, 4H), 2.17 (m, 4H), 2.49 (t, J=7.5 Hz, 4H), 4.88 (t, J=7.5 Hz, 4H), 6.81-7.06 (m, 4H), 8.01 (t, J=7.8 Hz, 2H), 8.19 (t, J=7.5 Hz, 2H), 8.28 (d, J=8.4 Hz, 2H), 8.53 (t, J=6.9 Hz, 4H), 8.79 (dd, J=6.9, 0.9 Hz, 2H), 10.16 (s, 2H) ppm; $^{13}$C NMR (75 MHz, CD$_3$OD) δ 26.6, 31.8, 32.2, 36.3, 62.6, 126.7, 127.4, 128.3, 128.7, 129.1, 129.4, 131.4, 132.3, 135.7, 138.1, 138.5, 143.1, 150.4 ppm.

Example 70

Synthesis of Compound N,N'-[(1,1'-biphenyl)-4,4'-di-(3-propanyl)]-bis-[3-(2'-S-1-methyl-pyrrolidin-2-yl)-pyridinium]dibromide

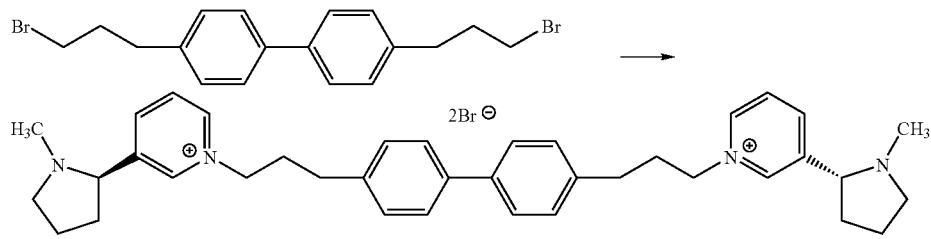

4,4'-Bis-(3-bromo-propyl)-biphenyl was added to a solution of S-nicotine (3 mmol) in acetonitrile and the solution refluxed for 24 hours. The acetonitrile was removed in vacuum and the resulting residue was partitioned between ether and water. The aqueous layer was washed extensively with ether until no S-nicotine left in the aqueous layer. The resulting aqueous solution of the product was lyophilized to yield the pure product. (75%). $^1$HNMR (300 MHz, D$_2$O, ppm), 9.10 (s, 2H), 9.01 (d, J=6.0, 2H), 8.52 (d, J=7.8, 2H), 8.05 (dd, 2H), 7.49 (d, J=8.1, 4H), 7.33 (d, J=8.1, 4H), 4.79 (t, J=7.5, 4H), 3.53 (t, J=8.1, 2H), 3.23 (m, 2H), 2.83 (t, J=7.5, 4H), 2.30-2.45 (m, 6H), 2.20 (s, 6H), 1.85-1.97 (m, 4H). CNMR, 145.85, 144.42, 143.74, 143.54, 139.48, 138.65, 129.07, 128.23, 126.81, 67.32, 61.64, 56.83, 39.90, 35.21, 32.87, 31.99, 23.09.

Example 71

Synthesis of Compound N,N'-[(1,1'-biphenyl)-4,4'-di-(3-propanyl)]-bis-(3,5-dimethylpyridinium)dibromide

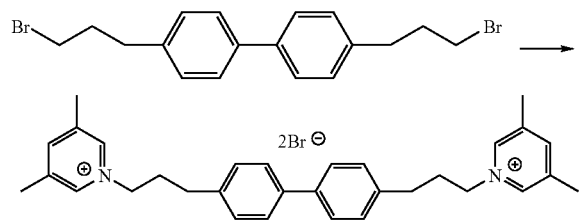

4,4'-Bis-(3-bromo-propyl)-biphenyl was added to a solution of 3,5-lutidine (3 mmol) in acetonitrile and the solution refluxed for 24 hours. The acetonitrile was removed in vacuum and the resulting residue was partitioned between ether and water. The aqueous layer was washed extensively with ether until no 3,5-lutidine left in the aqueous layer. The resulting aqueous solution of the product was lyophilized to yield the pure product. (75%). $^1$HNMR (300 MHz, D$_2$O, ppm), 8.79 (s, 4H), 8.15 (s, 2H), 7.46 (d, J=8.1, 4H), 7.31 (d, J=8.1, 4H), 4.66 (t, J=7.5, 4H), 2.81 (t, J=7.5, 2.46 (s, 12H), 2.34-2.39 (m, 4H). CNMR, 146.52, 141.58, 139.58, 139.00, 138.36, 129.05, 126.55, 61.28, 32.58, 32.05, 17.58.

Example 72

Synthesis of Compound N,N'-[(1,1'-biphenyl)-4,4'-di-(3-propanyl)]-bis-(3,4-dimethylpyridinium)dibromide 4,4'-Bis-(3-bromo-propyl)-biphenyl was added to a solution of 3,4-lutidine (3 mmol) in acetonitrile and the solution refluxed for 24 hours. The acetonitrile was removed in vacuum and the resulting residue was partitioned between ether and water. The aqueous layer was washed extensively with ether until no 3,4lutidine left in the aqueous layer. The resulting aqueous solution of the product was lyophilized to yield the pure product. (75%). $^1$HNMR (300 MHz, D$_2$O, ppm), 8.82 (s, 2H), 8.73 (d, J=6.3, 2H), 7.78 (d, J=6.3, 2H), 7.47 (d, J=8.4, 4H), 7.29 (d, J=8.4, 4H), 4.64 (t, J=7.2, 4H), 2.79 (t, J=7.2, 4H), 2.470 (s, 6H), 2.32-2.42 (m, 10H). CNMR, 158.42, 143.02, 141.37, 139.56, 138.50, 138.32, 129.04, 128.32, 126.56, 60.61, 32.56, 31.97, 19.44, 16.12.

Example 73

Synthesis of Compound N,N'-[(1,1'-biphenyl)-4,4'-di-(3-propanyl)]-bis-(2,4dimethylpyridinium)dibromide

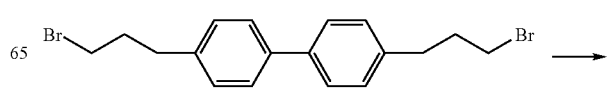

-continued

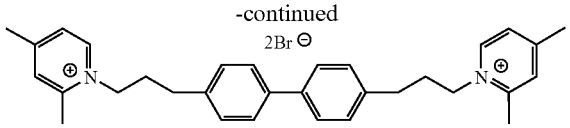

4,4'-Bis-(3-bromo-propyl)-biphenyl was added to a solution of 2,4-lutidine (3 mmol) in acetonitrile and the solution refluxed for 24 hours. The acetonitrile was removed in vacuum and the resulting residue was partitioned between ether and water. The aqueous layer was washed extensively with ether until no 2,4-lutidine left in the aqueous layer. The resulting aqueous solution of the product was lyophilized to yield the pure product. (75%). $^1$HNMR (300 MHz, $D_2O$, ppm), 8.83 (d, J=6.3, 2H), 7.79 (d, J=1.5, 2H), 7.68 (dd, J=7.8, J=1.5, 2H), 7.52 (d, J=8.4, 4H), 7.37 (d, J=8.4, 4H), 4.58 (t, J=7.5, 4H), 3.60 (t, J=7.2, 4H), 2.85 (t, J=7.2, 4H), 2.75 (s, 6H), 2.54 (s, 6H), 2.22-2.27 (m, 4H). CNMR, 159.10, 154.11, 144.30, 139.67, 138.39, 130.59, 129.22, 126.70, 126.55, 56.89, 31.94, 31.73, 31.02, 19.51.

Example 74

Synthesis of Compound N,N'-[(1,1'-biphenyl)-4,4'-di-(3-propanyl)]-bis-[3-(3-hydroxy-propyl)-pyridinium]dibromide

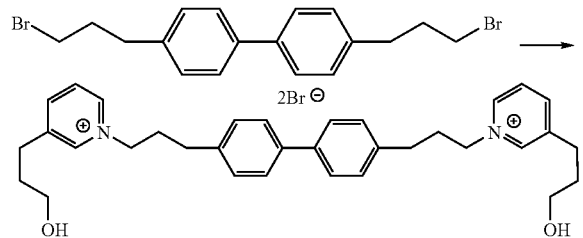

4,4'-Bis-(3-bromo-propyl)-biphenyl was added to a solution of 3-(3-hydroxypropyl)-pyridine (3 mmol) in acetonitrile and the solution refluxed for 24 hours. The acetonitrile was removed in vacuum and the resulting residue was partitioned between ether and water. The aqueous layer was washed extensively with ether until no 3-(3-Hydroxypropyl)-pyridine left in the aqueous layer. The resulting aqueous solution of the product was lyophilized to yield the pure product. (75%). $^1$HNMR (300 MHz, $D_2O$, ppm), 8.96 (s, 2H), 8.87 (d, J=6.0, 2H), 8.42 (d, J=7.8, 2H), 7.96 (dd, J=6.0, J=7.8, 2H), 7.48 (d, J=8.1, 4H), 7.29 (d, J=8.1, 4H), 4.70 (t, J=7.5, 4H), 3.60 (t, J=6.3, 4H), 2.92 (t, J=6.3, 4H), 2.81 (t, J=7.5, 4H), 2.41 (p, J=7.2, 4H), 1.87-1.95 (m, 4H). CNMR, 145.47, 144.22, 143.95, 142.22, 139.27, 138.77, 128.87, 127.75, 126.76, 61.55, 60.46, 32.94, 32.56, 31.96, 29.09.

Example 75

Synthesis of Compound N,N'-[(1,1'-biphenyl)-4,4'-di-(3-propanyl)]-bis-[5,6,7,8-tetrahydroquinolinium] dibromide

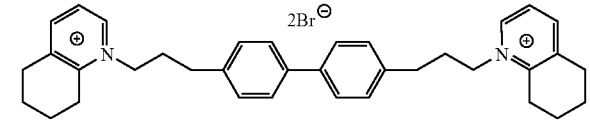

4,4'-Bis-(3-bromo-propyl)-biphenyl was added to a solution of 5,6,7,8-tetrahydroquinoline (3 mmol) in acetonitrile and the solution refluxed for 24 hours. The acetonitrile was removed in vacuum and the resulting residue was partitioned between ether and water. The aqueous layer was washed extensively with ether until no 5,6,7,8-tetrahydroquinoline left in the aqueous layer. The resulting aqueous solution of the product was lyophilized to yield the pure product. (75%). $^1$HNMR (300 MHz, $D_2O$, ppm), 8.79 (d, J=6.3, 2H), 8.19 (d, J=7.2, 2H), 7.77 (dd, J=6.3, J=7.8, 2H), 7.54 (d, J=7.8, 4H), 7.36 (d, J=7.8, 4H), 4.59 (t, J=7.8, 4H), 3.07 (t, J=6.3, 4H), 2.97 (t, J=6.0, 4H), 2.87 (t, J=7.5, 4H), 2.30 (p, J=7.5, 4H), 1.93-1.99 (m, 4H), 1.81-1.87 (m, 4H). CNMR, 154.12, 145.55, 143.40, 139.94, 139.38, 138.83, 128.99, 126.66, 124.51, 56.85, 31.93, 31.52, 28.77, 26.88, 21.54, 20.63.

Example 76

Synthesis of compound N,N'-[(1,1'-biphenyl)-4,4'-di-(3-propanyl)]-bis-[5,6,7,8-tetrahydroisoquinolinium] dibromide

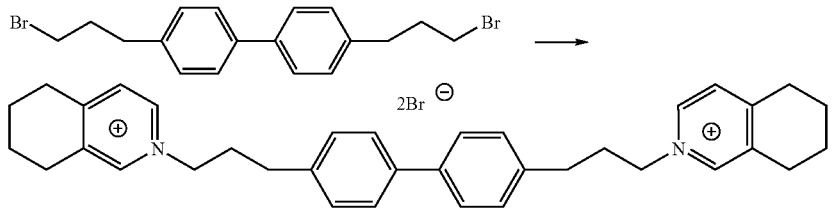

4,4'-Bis-(3-bromo-propyl)-biphenyl was added to a solution of 5,6,7,8-tetrahydroisoquinoline (3 mmol) in acetonitrile and the solution refluxed for 24 hours. The acetonitrile was removed in vacuum and the resulting residue was partitioned between ether and water. The aqueous layer was washed extensively with ether until no 5,6,7,8-tetrahydroisoquinoline left in the aqueous layer. The resulting aqueous solution of the product was lyophilized to yield the pure product. (75%). $^1$HNMR (300 MHz, D$_2$O, ppm), 8.67 (s, 2H), 8.60 (d, J=6.3, 2H), 7.68 (d, J=6.3, 2H), 7.48 (d, J=8.4, 4H), 7.29 (d, J=8.4, 4H), 4.59 (t, J=7.2, 4H), 2.94 (br, 4H), 2.86 (br, 4H), 2.81 (t, J=7.2,4H), 2.39 (p, J-7.5, 4H), 1.74-1.85 (m, 10H), CNMR, 158.38, 143.86, 140.21, 139.39, 138.64, 138.48, 128.86, 127.91, 126.56, 60.78, 21.12, 32.00, 29.31, 26.22, 21.11.

Example 77

Synthesis of Compound N,N'-[(1,1'-biphenyl)-4,4'-di-(3-propanyl)]-bis-(4-methylpyridinium)dibromide

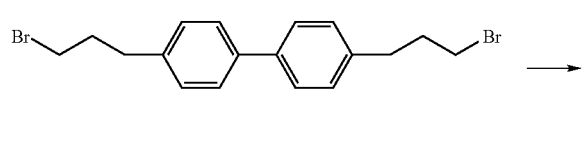

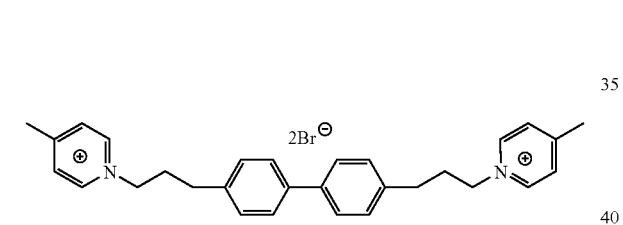

4,4'-Bis-(3-bromo-propyl)-biphenyl was added to a solution of 4-picoline (3 mmol) in acetonitrile and the solution refluxed for 24 hours. The acetonitrile was removed in vacuum and the resulting residue was partitioned between ether and water. The aqueous layer was washed extensively with ether until no 4-picoline left in the aqueous layer. The resulting aqueous solution of the product was lyophilized to yield the pure product. (75%). $^1$HNMR (300 MHz, D$_2$O, ppm), 8.90 (d, J=6.6, 4H), 7.85 (d, J=6.3, 4H), 7.48 (d, J=8.4, 4H), 7.32 (d, 8.4, 4H), 4.68 (t, J=7.5, 4H), 2.78 (t, J=7.8, 2.58 (s, 6H), 2.34 (m, 4H). CNMR, 159.77, 143.71, 139.52, 138.51, 129.08, 128.73, 126.76, 60.72, 32.76, 31.91, 21.27.

Example 78

Synthesis of Compound N,N'-[(1,1'-biphenyl)-4,4'-di-(3-propanyl)]-bis-(3-methylpyridinium)dibromide

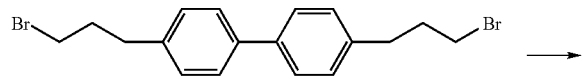

-continued

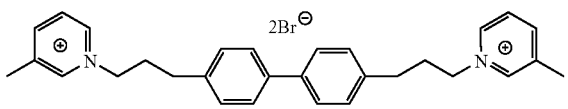

4,4'-Bis-(3-bromo-propyl)-biphenyl was added to a solution of 3-picoline (3 mmol) in acetonitrile and the solution refluxed for 24 hours. The acetonitrile was removed in vacuum and the resulting residue was partitioned between ether and water. The aqueous layer was washed extensively with ether until no 3-picoline left in the aqueous layer. The resulting aqueous solution of the product was lyophilized to yield the pure product. (75%). $^1$HNMR (300 MHz, D$_2$O, ppm), 9.00 (s, 2H), 8.92 (d, J=6.3, 2H), 8.35 (d, J=7.8, 2H), 7.93 (dd, J=6.0, J=8.1, 2H), 7.46 (d, J=8.4, 4H), 7.32 (d, J=8.4, 4H), 4.72 (t, J=7.5, 4H), 2.80 (t, J=7.5, 4H), 2.50 (s, 6H), 2.35-2.44 (m, 4H). CNMR, 146.06, 144.41, 141.92, 139.82, 139.55, 138.42, 129.11, 127.61, 126.70, 61.45, 32.76, 31.99, 17.80.

Example 79

Synthesis of Compound N,N'-[(1,1'-biphenyl)-4,4'-di-(3-propanyl)]-bis-(2-methylpyridinium)dibromide 4,4'-Bis-(3-bromo-propyl)-biphenyl was added to a solution of 2-picoline (3 mmol) in acetonitrile and the solution refluxed for 24 hours. The acetonitrile was removed in vacuum and the resulting residue was partitioned between ether and water. The aqueous layer was washed extensively with ether until no 2-picoline left in the aqueous layer. The resulting aqueous solution of the product was lyophilized to yield the pure product. (75%). $^1$HNMR (300 MHz, D$_2$O, ppm), 9.02 (d, J=6.3, 2H), 8.40 (dt, J=1.5, J=7.8, 2H), 7.97 (d, J=7.8, 2H), 7.90 (t, J=6.3, 2H), 7.53 (d, J=8.1, 4H), 7.38 (d, J=8.1, 4H), 4.65 (t, J=7.8, 4H), 2.86 (t, J=7.8, 4H), 2.82 (s, 6H), 2.24-2.32 (m, 4H) CNMR, 155.49, 145.33, 145.23, 139.56, 138.54, 130.41, 129.21, 126.78, 125.89, 57.71, 31.93, 31.71, 19.75.

Example 80

Synthesis of Compound N,N'-{2,2'-[oxybis-(2,1-ethandiyloxy)]bis-ethyl}-bis-[3-(2'-S-1-methyl-pyrrolidin-2-yl)-pyridinium]dichloride

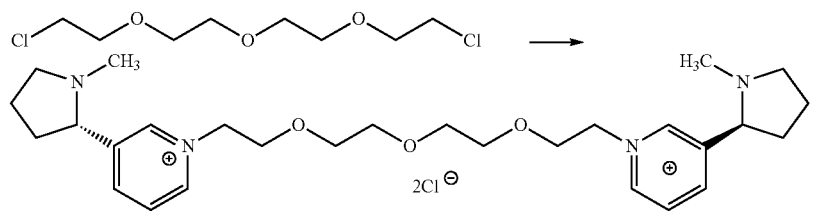

1-Chloro-2-{2-[2-(2-chloro-ethoxy)-ethoxy]-ethoxy}-ethane was added to a solution of S-nicotine (3 mmol) in acetonitrile and the solution refluxed for 24 hours. The acetonitrile was removed in vacuum and the resulting residue was partitioned between ether and water. The aqueous layer was washed extensively with ether until no S-nicotine left in the aqueous layer. The resulting aqueous solution of the product was lyophilized to yield the pure product. (75%). $^1$HNMR (300 MHz, D$_2$O, ppm), 8.63-6.64 (m, 4H), 8.38 (d, J=8.1, 2H), 7.90 (dd, J=7.8, d=6.6, 2H), 2.61-2.63 (m, 4H), 3.85 (t, J=4.8, 4H), 3.36-3.47 (m, 10H), 3.04-3.04 (m, 2H), 2.20-2.38 (m, 4H), 2.04 (s, 6H), 1.60-1.84 6H).

Example 81

Synthesis of Compound N,N'-{2,2'-[oxybis-(2,1-ethandiyloxy)]bis-ethyl}-bis(2-methylpyridinium) dichloride

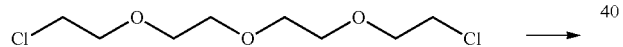

1-Chloro-2-{2-[2-(2-chloro-ethoxy)-ethoxy]-ethoxy}-ethane was added to a solution of 2-picoline (3 mmol) in acetonitrile and the solution refluxed for 24 hours. The acetonitrile was removed in vacuum and the resulting residue was partitioned between ether and water. The aqueous layer was washed extensively with ether until no 2-picoline left in the aqueous layer. The resulting aqueous solution of the product was lyophilized to yield the pure product. (75%). $^1$HNMR (300 MHz, D$_2$O, ppm), 8.55 (dd, J=6.3, J=1.2, 2H), 8.23 (dt, J=7.8, J=1.5, 2H), 7.75 (d, J=7.8, 2H), 7.68 (dt, J=7.8, J=1.5, 2H), 4.62 (t, 4H), 3.82 (t, 4H), 3.40-3.44 (m, 4H), 3.35-3.39 (m, 4H), 2.36 (s, 6H).

Example 82

Synthesis of Compound N,N'-{2,2'-[oxybis-(2,1-ethandiyloxy)]bis-ethyl}-bis(3-methylpyridinium) dichloride 1-Chloro-2-{2-[2-(2-chloro-ethoxy)-ethoxy]-ethoxy}-ethane was added to a solution of 3-picoline (3 mmol) in acetonitrile and the solution refluxed for 24 hours. The acetonitrile was removed in vacuum and the resulting residue was partitioned between ether and water. The aqueous layer was washed extensively with ether until no 3-picoline left in the aqueous layer. The resulting aqueous solution of the product was lyophilized to yield the pure product. (75%). $^1$HNMR (300 MHz, D$_2$O, ppm), 8.54 (s, 2H), 8.49 (d, J=6.0, 8.22 (d, J=8.1, 2H), 8.76 (dd, J=8.1, J=6.0, 2H), 4.57 (t, J=4.8, 4H), 3.84 (t, J=5.1, 4H), 3.43-3.48 (m, 4H), 3.35-3.39 (m, 4H), 2.69 (s, 6H). CNMR, 146.48, 144.22, 141.89, 139.81, 127.33, 69.93, 69.60, 68.95, 60.97, 17.89.

Example 83

Synthesis of Compound N,N'-{2,2'-[oxybis-(2,1-ethandiyloxy)]bis-ethyl}-bis(4-methylpyridinium) dichloride 1-Chloro-2-{2-[2-(2-chloro-ethoxy)-ethoxy]-ethoxy}-ethane was added to a solution of 4-picoline (3 mmol) in acetonitrile and the solution refluxed for 24 hours. The acetonitrile was removed in vacuum and the resulting residue was partitioned between ether and water. The aqueous layer was washed extensively with ether until no 4-picoline left-in the aqueous layer. The resulting aqueous solution of the product was lyophilized to yield the pure product. (75%). $^1$HNMR (300 MHz, $D_2O$, ppm), 8.47 (d, J=6.9, 4H), 7.70 (d, J=6.3, 4H), 4.54 (t, J=4.8, 4H), 3.83 (t, J=4.8, 4H), 3.43-3.47 (m, 4H), 3.35-3.38 (m, 4H), 2.47 (s, 6H). CNMR, 160.56, 143.63, 128.52, 69.92, 69.57, 68.95, 60.27, 21.58.

Example 84

Synthesis of Compound N,N'-{2,2'-[oxybis-(2,1-ethandiyloxy)]bis-ethyl}-bis(5,6,7,8-tetrahydroquinolinium)dichloride

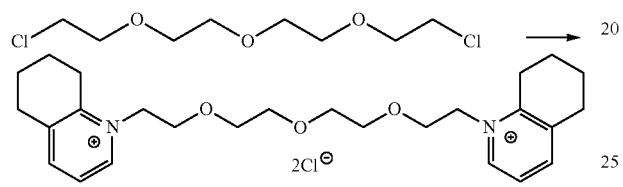

1-Chloro-2-{2-[2-(2-chloro-ethoxy)-ethoxy]-ethoxy}-ethane was added to a solution of tetrahydroquinoline (3 mmol) in acetonitrile and the solution refluxed for 24 hours. The acetonitrile was removed in vacuum and the resulting residue was partitioned between ether and water. The aqueous layer was washed extensively with ether until no tetrahydroquinoline left in the aqueous layer. The resulting aqueous solution of the product was lyophilized to yield the pure product. (75%).$^1$HNMR (300 MHz, $D_2O$, ppm), 8.39 (d, J=6.3, 2H), 8.04 (d, J=8.1, 2H), 7.55 (dd, J=8.1, J=6.3, 2H), 4.57 (t, J=4.5, 4H), 3.83 (t, J=4.5, 4H), 4.43-3.49 (m, 4H), 3.36-3.38 (m 4H), 2.98 (t, 6.3, 4H), 2.82 (t, J=6.3, 4H), 1.79-1.83 (m, 4H), 1.63-1.69 (m, 4H). CNMR, 154.58, 145.92, 143.59, 139.99, 123.92, 70.19, 69.74, 68.40, 56.28, 49.10, 28.72, 27.26, 21.40, 20.45.

Example 85

Synthesis of Compound N,N'-{2,2'-[oxybis-(2,1-ethandiyloxy)]bis-ethyl}-bis(5,6,7,8-tetrahydroisoquinolinium)dichloride

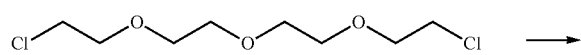

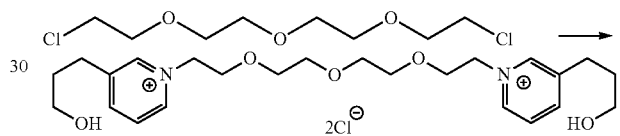

1-Chloro-2-{2-[2-(2-chloro-ethoxy)-ethoxy]-ethoxy}-ethane was added to a solution of tetrahydroisoquinoline (3 mmol) in acetonitrile and the solution refluxed for 24 hours. The acetonitrile was removed in vacuum and the resulting residue was partitioned between ether and water. The aqueous layer was washed extensively with ether until no tetrahydroisoquinoline left in the aqueous layer. The resulting aqueous solution of the product was lyophilized to yield the pure product. (75%). $^1$HNMR (300 MHz, $D_2O$, ppm), 8.33 (s, 2H), 8.24 (d, J=6.3, 2H), 7.52 (d, J=6.3, 2H), 4.47 (t, J=4.8, 4H), 3.81 (t, J=4.8, 4H), 3.42-3.45 (m, 4H), 3.33-3.37 (m, 4H), 2.81-2.84 (br, 4H), 2.70-2.74 (br, 4H), 1.63-1.70 (m, 8H). CNMR, 159.33, 143.61, 140.12, 138.77, 127.74, 69.96, 69.60, 69.02, 60.12, 29.40, 26.18, 20.98, 20.95.

Example 86

Synthesis of Compound N,N'-{2,2'-[oxybis-(2,1-ethandiyloxy)]bis-ethyl}-bis-[3-(3-hydroxypropyl)-pyridinium]dichloride

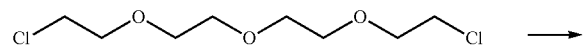

1-Chloro-2-{2-[2-(2-chloro-ethoxy)-ethoxy]-ethoxy}-ethane was added to a solution of 3-(3-hydroxypropyl)-pyridine (3 mmol) in acetonitrile and the solution refluxed for 24 hours. The acetonitrile was removed in vacuum and the resulting residue was partitioned between ether and water. The aqueous layer was washed extensively with ether until no 3-(3-hydroxypropyl)-pyridine left in the aqueous layer. The resulting aqueous solution of the product was lyophilized to yield the pure product. (75%). $^1$HNMR (300 MHz, $D_2O$, ppm), 8.59 (s, 2H), 8.53 (d, J=6.0, 8.29 (d, J=8.4, 2H), 7.81 (dd, J=8.4, J=6.0, 2H), 4.60 (t, J=4.8, 4H), 3.85 (t, J=4.5, 4H), 3.44-3.49 (m, 8H), 3.36-3.39 (m, 4H), 2.76 (t, J=7.8, 4H), 1.74-1.80 (m, 4H). CNMR, 145.99, 144.09, 143.35, 142.35, 127.64, 69.96, 69.64, 68.96, 61.06, 60.60, 31.21, 28.81.

Example 87

Synthesis of Compound N,N'-{2,2'-[oxybis-(2,1-ethandiyloxy)]bis-ethyl}-bis-(3-hydroxymethylpyridinium)dichloride

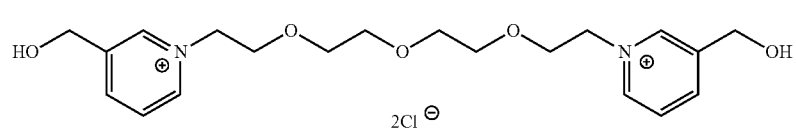

1-Chloro-2-{2-[2-(2-chloro-ethoxy)-ethoxy]-ethoxy}-ethane was added to a solution of 3-hydroxymethylpyridine (3 mmol) in acetonitrile and the solution refluxed for 24 hours. The acetonitrile was removed in vacuum and the resulting residue was partitioned between ether and water. The aqueous layer was washed extensively with ether until no 3-hydroxymethylpyridine left in the aqueous layer. The resulting aqueous solution of the product was lyophilized to yield the pure product. (75%). $^1$HNMR (300 MHz, D$_2$O, ppm), 8.72 (s, 2H), 8.65 (d, J=6.0, 8.39 (d, J=7.8, 2H), 7.91 (t, J=6.9, 2H), 4.69 (t, J=4.8, 4H), 4.64 (s, 4H), 3.89 (t, J=4.2, 4H), 3.41-3.49 (m, 8H).

Example 88

Synthesis of Compound N,N'-{2,2'-[oxybis-(2,1-ethandiyloxy)]bis-ethyl}-bis-(2,4-dimethylpyridinium)dichloride

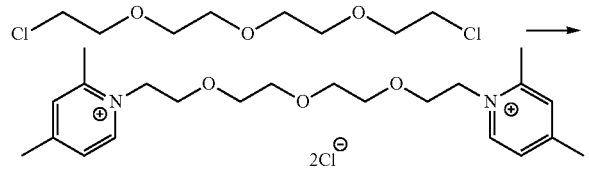

1-Chloro-2-{2-[2-(2-chloro-ethoxy)-ethoxy]-ethoxy}-ethane was added to a solution of 2,4dimethylpyridine (3 mmol) in acetonitrile and the solution refluxed for 24 hours. The acetonitrile was removed in vacuum and the resulting residue was partitioned between ether and water. The aqueous layer was washed extensively with ether until no 2,4dimethylpyridine left in the aqueous layer. The resulting aqueous solution of the product was lyophilized to yield the pure product. (75%). $^1$HNMR (300 MHz, D$_2$O, ppm), 3.35 (d, J=6.6, 2H), 7.58 (s, 2H), 7.50 (d, J=6.6, 2H), 4.54 (t, J=4.8, 4H), 3.82 (t, J=4.8, 4H), 3.41-3.45 (m, 4H), 3.34-3.36 (m, 4H), 2.62 (s, 6H). 2.40 (s, 6H). CNMR, 159.76, 154.44, 144.47, 130.31, 126.00, 70.16, 69.66, 68.42, 56.36, 49.10, 21.27, 19.90.

Example 89

Synthesis of compound N,N'-{2,2'-[oxybis-(2,1-ethandiyloxy)]bis-ethyl}-bis-(3,4-dimethylpyridinium)dichloride

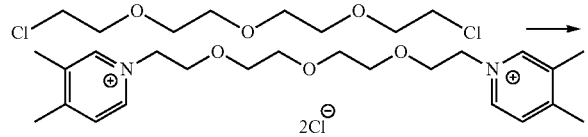

1-Chloro-2-{2-[2-(2-chloro-ethoxy)-ethoxy]-ethoxy}-ethane was added to a solution of 3,4-dimethylpyridine (3 mmol) in acetonitrile and the solution refluxed for 24 hours. The acetonitrile was removed in vacuum and the resulting residue was partitioned between ether and water. The aqueous layer was washed extensively with ether until no 3,4-dimethylpyridine left in the aqueous layer. The resulting aqueous solution of the product was lyophilized to yield the pure product. (75%). $^1$HNMR (300 MHz, D$_2$O, ppm), 8.36 (s, 2H), 8.30 (d, J=6.3, 2H), 7.61 (d, J=6.3, 2H), 4.49 (t, J=4.8, 4H), 3.81 (t, J=4.8, 4H), 3.42-3.45 (m, 4H), 3.34-3.37 (m, 4H), 2.37 (s, 6H). 2.25 (s, 6H). CNMR, 159.23, 142.79, 141.27, 138.49, 128.06, 69.92, 69.58, 69.01, 60.08, 49.07, 19.75, 16.32.

Example 90

Synthesis of Compound N,N'-{2,2'-[oxybis-(2,1-ethandiyloxy)]bis-ethyl}-bis-(3,5-dimethylpyridinium)dichloride

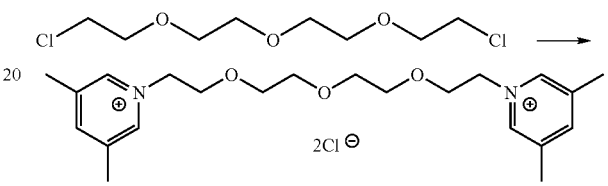

1-Chloro-2-{2-[2-(2-chloro-ethoxy)-ethoxy]-ethoxy}-ethane was added to a solution of 3,5-dimethylpyridine (3 mmol) in acetonitrile and the solution refluxed for 24 hours. The acetonitrile was removed in vacuum and the resulting residue was partitioned between ether and water. The aqueous layer was washed extensively with ether until no 3,5-dimethylpyridine left in the aqueous layer. The resulting aqueous solution of the product was lyophilized to yield the pure product. (75%). $^1$HNMR (300 MHz, D$_2$O, ppm), 8.34 (s, 4H), 8.06 (s, 2H), 4.52 (t, J=4.8, 4H), 3.83 (t, J=4.8, 4H), 3.42-3.46 (m, 4H), 3.35-3.38 (m, 4H), 2.31 (s, 12H). CNMR, 146.98, 141.42, 138.93, 69.95, 69.61, 69.01, 60.75, 49.08, 17.68.

Example 91

Synthesis of Compound N,N'-(5,7-dodecadiyn-1,12-diyl)-bis-(2-methylpyridinium)dichloride

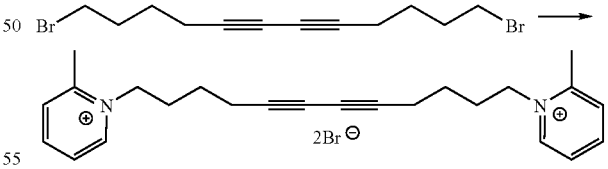

1,12-Dibromo-dodeca-5,7-diyne was added to a solution of 2-picoline (3 mmol) in acetonitrile and the solution refluxed for 24 hours. The acetonitrile was removed in vacuum and the resulting residue was partitioned between ether and water. The aqueous layer was washed extensively with ether until no 2-picoline left in the aqueous layer. The resulting aqueous solution of the product was lyophilized to yield the pure product. (75%). $^1$HNMR (300 MHz, D$_2$O, ppm), 8.58 (d, 2H), 8.18-8.24 (m, 2H), 7.65-7.74 (m 4H), 4.40 (t, 4H), 2.68 (s, 6H), 2.21 (t, 4H), 1.84-1.94 (m, 4H), 1.46-

1.54 (m, 4H). CNMR, 155.29, 145.16, 144.78, 130.32, 125.75, 77.89, 65.52, 57.61, 28.78, 24.44, 18.19.

Example 92

Synthesis of Compound N,N'-(5,7-dodecadiyn-1,12-diyl)-bis-(3-methylpyridinium)dichloride

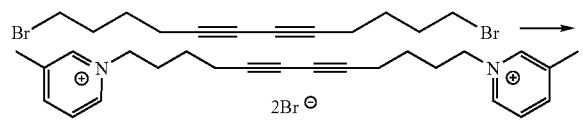

1,12-Dibromo-dodeca-5,7-diyne was added to a solution of 3-picoline (3 mmol) in acetonitrile and the solution refluxed for 24 hours. The acetonitrile was removed in vacuum and the resulting residue was partitioned between ether and water. The aqueous layer was washed extensively with ether until no 3-picoline left in the aqueous layer. The resulting aqueous solution of the product was lyophilized to yield the pure product. (75%). $^1$HNMR (300 MHz, D$_2$O, ppm), 8.72 (s, 2H), 8.66 (d, 2H), 8.38 (d, 2H), 7.94 (dd, 2H). 4.59 (t, 4H), 2.58 (s, 6H), 2.32 (t, 4H), 2.28 (p,4H), 1.59 (p, 4H). CNMR, 146.17, 143.83, 141.40, 140.11, 127.60, 77.95, 65.54, 61.35, 30.00, 24.36, 18.22, 18.00.

Example 93

Synthesis of Compound N,N'-(5,7-dodecadiyn-1,12-diyl)-bis-(4-methylpyridinium)dichloride

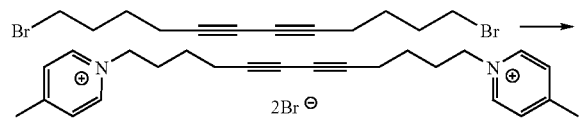

1,12-Dibromo-dodeca-5,7-diyne was added to a solution of 4-picoline (3 mmol) in acetonitrile and the solution refluxed for 24 hours. The acetonitrile was removed in vacuum and the resulting residue was partitioned between ether and water. The aqueous layer was washed extensively with ether until no 4-picoline left in the aqueous layer. The resulting aqueous solution of the product was lyophilized to yield the pure product. (75%). $^1$HNMR (300 MHz, D$_2$O, ppm), 8.48 (d, 4H), 7.68 (d, 4H), 4.38 (t, 4H), 2.46 (s, 6H), 2.18 (t, 4H), 1.86-1.98 (m, 4H), 1.34-1.44 (m, 4H). CNMR, 160.12, 143.13, 128.77, 77.87, 65.47, 60.61, 29.86, 24.30, 21.56, 18.17.

Example 94

Synthesis of Compound N,N'-(5,7-dodecadiyn-1,12-diyl)-bis-(3,4-dimethylpyridinium)dichloride

-continued

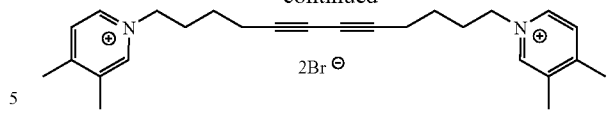

1,12-Dibromo-dodeca-5,7-diyne was added to a solution of 3,4-lutidine (3 mmol) in acetonitrile and the solution refluxed for 24 hours. The acetonitrile was removed in vacuum and the resulting residue was partitioned between ether and water. The aqueous layer was washed extensively with ether until no 3,4-lutidine left in the aqueous layer. The resulting aqueous solution of the product was lyophilized to yield the pure product. (75%). $^1$HNMR (300 MHz, D$_2$O, ppm), 8.35 (s, 2H), 8.29 (d, 2H), 7.60 (d, 2H), 4.32 (t, 4H), 2.38 (s, 6H), 2.24 (s, 6H), 2.16 (t, 4H), 1.86-1.94 (m, 4H), 1.30-1.42 (m 4H).

Example 95

Synthesis of compound N,N'-(5,7-dodecadiyn-1,12-diyl)-bis-(3,5-dimethylpyridinium)dichloride

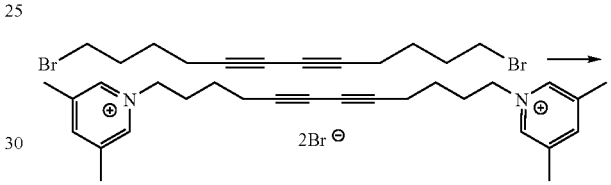

1,12-Dibromo-dodeca-5,7-diyne was added to a solution of 3,5-lutidine (3 mmol) in acetonitrile and the solution refluxed for 24 hours. The acetonitrile was removed in vacuum and the resulting residue was partitioned between ether and water. The aqueous layer was washed extensively with ether until no 3,5-lutidine left in the aqueous layer. The resulting aqueous solution of the product was lyophilized to yield the pure product. (75%). $^1$HNMR (300 MHz, D$_2$O, ppm), 8.32 (s, 4H), 8.00 (s, 2H), 4.36 (t, 4H), 2.34 (s, 12H), 2.18 (t, 4H), 1.86-1.94 (m, 4H), 1.34-1.44 (m, 4H). CNMR, 146.62, 140.97, 139.15, 77.88, 65.41, 61.05, 29.88, 24.28, 18.14, 17.70.

Example 96

Synthesis of Compound N,N'-(5,7-dodecadiyn-1,12-diyl)-bis-(5,6,7,8-tetrahydroisoquinolinium)dichloride

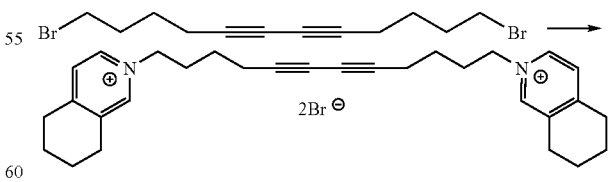

1,12-Dibromo-dodeca-5,7-diyne was added to a solution of tetrahydroisoquinoline (3 mmol) in acetonitrile and the solution refluxed for 24 hours. The acetonitrile was removed in vacuum and the resulting residue was partitioned between ether and water. The aqueous layer was washed extensively with ether until no tetrahydroisoquinoline left in the aqueous layer. The resulting aqueous solution of the product was lyophilized to yield the pure product. (75%). ¹HNMR (300 MHz, D₂O, ppm), 8.34 (s, 2H), 8.22 (d, J=6.3, 2H), 7.54 (d, J=6.3, 2H), 4.31 (t, J=7.2, 4H), 2.82-2.84 (br, 4H), 2.71-2.73 (br, 4H), 2.12 (t, J=6.6, 4H), 1.81-1.91 (m, 4H), 1.64-1.69 (m, 8H), 1.29-1.38 (m, 4H). CNMR, 158.94, 143.15, 139.67, 139.05, 128.01, 77.81, 65.50, 60.46, 29.92, 29.41, 26.26, 24.38, 21.02, 21.05, 18.20.

Example 97

Synthesis of Compound N,N'-[(1,4-phenylene)-bis-(4-butynyl)]-bis-(3-methyl-pyridinium)dibromide

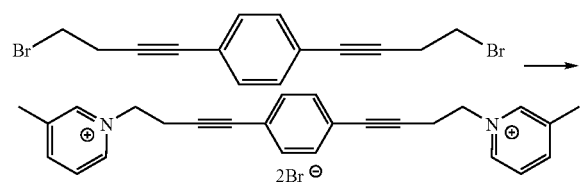

1,4-Bis-(4-bromo-but-1-ynyl)-benzene was added to a solution of 3-picoline (3 mmol) in acetonitrile and the solution refluxed for 24 hours. The acetonitrile was removed in vacuum and the resulting residue was partitioned between ether and water. The aqueous layer was washed extensively with ether until no 3-picoline left in the aqueous layer. The resulting aqueous solution of the product was lyophilized to yield the pure product. (75%). ¹HNMR (300 MHz, D₂O, ppm), 8.67 (s, 2H), 8.60 (d, J=6.0 Hz, 2H), 8.25 (d, J=8.0Hz, 2H), 7.80 (dd, J=6.0 Hz, J=8.0 Hz, 2H), 7.14 (s, 4H), 4.63 (m, 4H), 3.02 (t, J=6.3 Hz, 4H), 2.36 (s, 6H). CNMR, 146.68, 144.11, 141.66, 139.87, 131.59, 127.39, 122.22, 86.10, 84.40, 59.68, 21.95, 17.90.

Example 98

Synthesis of Compound N,N'-[(1,4-phenylene)-bis-(4-butynyl)]-bis-(4-methyl-pyridinium)dibromide

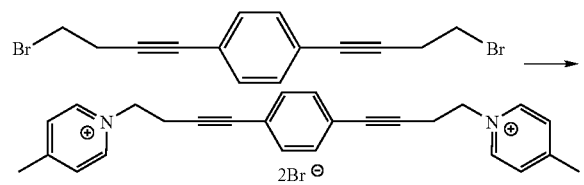

1,4-Bis-(4-bromo-but-1-ynyl)-benzene was added to a solution of 4-picoline (3 mmol) in acetonitrile and the solution refluxed for 24 hours. The acetonitrile was removed in vacuum and the resulting residue was partitioned between ether and water. The aqueous layer was washed extensively with ether until no 4-picoline left in the aqueous layer. The resulting aqueous solution of the product was lyophilized to yield the pure product. (75%). ¹HNMR (300 MHz, D₂O, ppm), 8.60 (d, J=6.6 Hz, 4H), 7.73 (d, J=6.6 Hz, 4H), 7.15 (s, 4H), 4.60 (t, J=6 Hz, 4H), 3.01 (t, J=6.0 Hz, 2.49 (s, 6H). CNMR, 160.87, 143.41, 131.58, 128.57, 122.26, 86.16, 84.25, 59.03, 21.87, 21.68.

Example 99

Synthesis of Compound N,N'-[(1,4-phenylene)-bis-(4-butynyl)]-bis-(5,6,7,8-tetrahydroisoquiolinium) dibromide

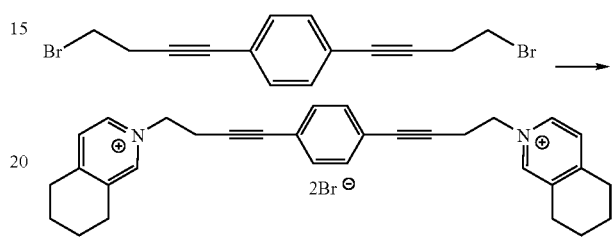

1,4-Bis-(4-bromo-but-1-ynyl)-benzene was added to a solution of terahydroisoquinoline (3 mmol) in acetonitrile and the solution refluxed for 24 hours. The acetonitrile was removed in vacuum and the resulting residue was partitioned between ether and water. The aqueous layer was washed extensively with ether until no terahydroisoquinoline left in the aqueous layer. The resulting aqueous solution of the product was lyophilized to yield the pure product. (75%). ¹HNMR (300 MHz, D₂O, ppm), 8.46 (s, 2H), 8.35 (d, J=6.6 Hz, 2H), 7.56 (d, J=6.6 Hz, 2H), 7.09 (s, 4H), 4.54 (t, J=6.3 Hz, 4H), 2.98 (t, J=6.3 Hz, 4H), 2.83 (t, J=6.0 Hz, 4H), 2.66 (t, J=5.4 Hz, 4H), 1.64-1.68 (m, 8H).

Example 100

Synthesis of Compound N,N'-[(1,4-phenylene)-bis-(4-butynyl)]-bis-(3,4-dimethyl-pyridinium)dibromide

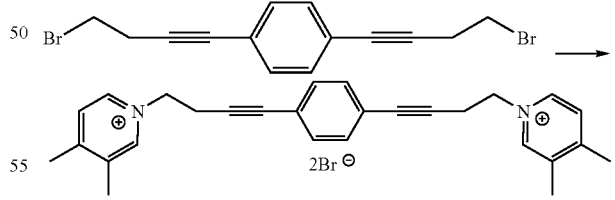

1,4-Bis-(4-bromo-but-1-ynyl)-benzene was added to a solution of 3,4-lutidine (3 mmol) in acetonitrile and the solution refluxed for 24 hours. The acetonitrile was removed in vacuum and the resulting residue was partitioned between ether and water. The aqueous layer was washed extensively with ether until no 3,4-lutidine left in the aqueous layer. The resulting aqueous solution of the product was lyophilized to yield the pure product. (75%). ¹HNMR (300 MHz, D₂O, ppm), 8.50 (s, 2H), 8.44 (d, J=6.3 Hz, 2H), 7.65 (d, J=6.3 Hz, 2H), 7.13 (s, 4H), 4.57 (t, J=6.3 Hz, 4H), 2.99 (t, J=6.3 Hz, 4H), 2.38 (s, 6H), 2.24 (s, 6H).

Example 101

Synthesis of Compound N,N'-[(1,4-phenylene)-bis-(4-butynyl)]-bis-(3,5-dimethyl-pyridinium)dibromide

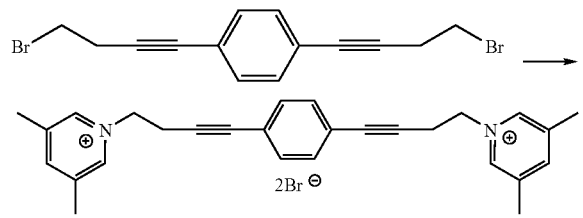

1,4-Bis-(4-bromo-but-1-ynyl)-benzene was added to a solution of 3,5-lutidine (3 mmol) in acetonitrile and the solution refluxed for 24 hours. The acetonitrile was removed in vacuum and the resulting residue was partitioned between ether and water. The aqueous layer was washed extensively with ether until no 3,5-lutidine left in the aqueous layer. The resulting aqueous solution of the product was lyophilized to yield the pure product. (75%). $^1$HNMR (300 MHz, D$_2$O, ppm), 8.46 (s, 4H), 8.04 (s, 2H), 7.11 (s, 4H), 4.59 (t, J=6.3 Hz, 4H), 2.99 (t, J=6.3 Hz, 4H), 2.29 (s, 12H). CNMR, 147.17, 141.31, 138.96, 131.59, 122.24, 86.31, 84.46, 59.45, 21.99, 17.73.

Example 102

Synthesis of Compound N,N'-[(1,1'-biphenyl)-4,4'-di-(1-propyn-3-yl)]-bis-(3-methylpyridinium)dibromide

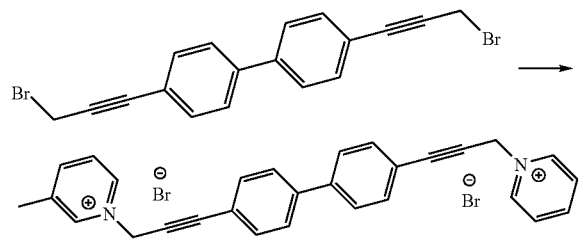

4,4'-Bis-(3-bromo-prop-1-ynyl)-biphenyl (1 mmol) was added to a solution of 3-picoline (3 mmol) in acetonitrile and the solution refluxed for 24 hours. The acetonitrile was removed in vacuum and the resulting residue was partitioned between ether and water. The aqueous layer was washed extensively with ether until no 3-picoline left in the aqueous layer. The resulting aqueous solution of the product was lyophilized to yield the pure product. (75%). $^1$HNMR (300 MHz, d$_6$-DMSO, ppm), 9.16 (s, 2H), 9.12 (s, 2H), 8.54 (d, 2H), 8.22 (dd, 2H), 7.8 (d, 4H), 7.62 (d, 4H), 5.8 (s, 4H), 2.4 (s, 6H). CNMR, 147.52, 144.53, 142.46, 140.44, 139.73, 133.14, 128.36, 127.69, 120.85, 89.16, 82.81, 51.19, 18.79.

Example 103

Synthesis of Compound N,N'-[(1,1'-biphenyl)-4,4'-di-(1-propyn-3-yl)]-bis-(4-methylpyridinium)dibromide

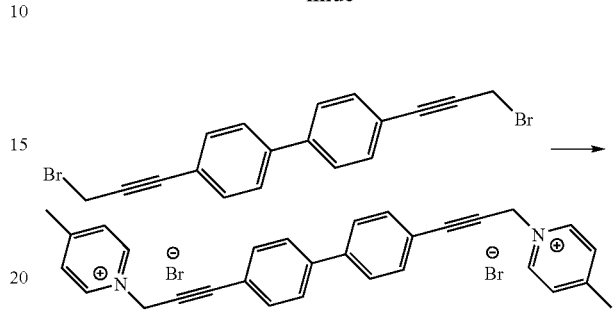

4,4'-Bis-(3-bromo-prop-1-ynyl)-biphenyl (1 mmol) was added to a solution of 4-picoline (3 mmol) in acetonitrile and the solution refluxed for 24 hours. The acetonitrile was removed in vacuum and the resulting residue was partitioned between ether and water. The aqueous layer was washed extensively with ether until no 4-picoline left in the aqueous layer. The resulting aqueous solution of the product was lyophilized to yield the pure product. (75%). $^1$HNMR (300 MHz, d$_6$-DMSO, ppm), 9.05 (d, 4H), 8.06 (d, 4H), 7.78 (d, 4H), 7.62 (d, 4H), 5.8 (s, 4H), 2.62 (s, 6H). CNMR, 160.67, 144.10, 140.41, 133.11, 129.27, 127.69, 120.85, 89.06, 82.97, 50.56, 22.39.

Example 104

Synthesis of Compound N,N'-[(1,1'-biphenyl)-4,4'-di-(1-propyn-3-yl)]-bis-(3,4-dimethylpyridinium) dibromide

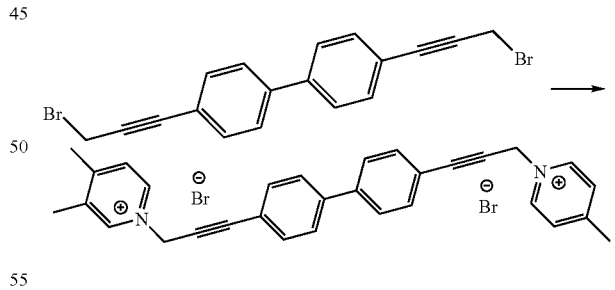

4,4'-Bis-(3-bromo-prop-1-ynyl)-biphenyl (1 mmol) was added to a solution of 3,4-lutidine (3 mmol) in acetonitrile and the solution refluxed for 24 hours. The acetonitrile was removed in vacuum and the resulting residue was partitioned between ether and water. The aqueous layer was washed extensively with ether until no 3,4-lutidine left in the aqueous layer. The resulting aqueous solution of the product was lyophilized to yield the pure product. (75%). $^1$HNMR (300 MHz, d$_6$-DMSO, ppm), 9.02 (s, 2H), 8.88 (d, 2H), 8.0 (d, 2H), 7.8 (d, 4H), 7.6 (d, 4H), 5.9 (s, 4H), 2.46 (s, 6H), 2.40 (s, 6H). CNMR, 159.64, 143.10, 141.96, 140.39, 138.65, 133.12, 128.88, 127.68, 120.88, 88.83, 83.08, 50.41, 20.66, 17.19.

Example 105

Inhibition of [$^3$H]NIC and [$^3$H]Methyllycaconitine Binding Assays

Whole brain, excluding cortex and cerebellum, was homogenized in 20 vol of ice-cold buffer, 5 containing (in mM): 2 HEPES, 11.8 NaCl, 0.48 KCl, 0.25 CaCl$_2$ and 0.12 MgSO$_4$, pH 7.5. Homogenate was centrifuged (25,000 g, 15 min, 4° C). Pellets were resuspended in 20 vol buffer and incubated at 37° C., for 10 min, cooled to 4° C. and centrifuged (25,000 g, 15 min, 4° C.). Pellets were resuspended and centrifuged using the same conditions. Final pellets were stored in assay buffer, containing (in mM): 20 HEPES, 118 NaCl, 4.8 KCl, 2.5 CaCl$_2$, and 1.2 MgSO$_4$, pH 7.5 at −70° C. Upon use, final pellets were resuspended in 20 vol assay buffer. Samples (250 µl) contained 100-140 µg of membrane protein, 3 nM [$^3$H]-S-nicotine or 3 nM [$^3$H]-methyllycaconitine (MLA), and bis-quaternary ammonium analog (100 nM) in assay buffer containing 50 mM Tris. Control was in the absence of analog. In [$^3$H]-S-nicotine and [$^3$H]-methyllycaconitine binding assays, nonspecific binding was determined in the presence of 10 µM cytisine and 10 µM S-nicotine, respectively. Incubations proceeded for 60 min at room temperature using 96-well plates and were terminated by harvesting on Unifilter-96 GF/B filter plates presoaked in 0.5% polyethylenimine, using a Packard FilterMate harvester. After washing 5 times with 350 µl ice-cold assay buffer, filter plates were dried (60 min, 4° C.), bottom-sealed, and filled with Packard's MicroScint 20 cocktail (40 µl/well). After 60 min, filter plates were top-sealed, and radioactivity determined using a Packard TopCount. Protein concentrations were determined using the Bradford dye-binding procedure bovine serum albumin as the standard. The results are summarized in Table 1.

Example 106

Inhibition of S-Nicotine-evoked [$^3$H]Neurotransmitter Release Assay

Rat striatal slices (500 µm thickness, 6-8 mg wet weight) were incubated for 30 minutes in Krebs buffer (118 mM NaCl, 4.7 mM KCl, 1.2 mM MgCl$_2$, 1.0 mM NaH$_2$PO$_4$, 1.3 mM CaCl$_2$, 11.1 mM glucose, 25 mM NaHCO$_3$, 0.11 mM L-ascorbic acid, and 0.004 mM disodium EDTA; pH 7.4, and saturated with 95% O$_2$/5% CO$_2$) in a metabolic shaker at 34° C. Slices were rinsed with 15 mL of fresh buffer and incubated for an additional 30 minutes in fresh buffer containing 0.1 µM [$^3$H]dopamine (DA; 6 slices/3 mL). Subsequently, slices were rinsed with 15 mL of fresh buffer and transferred to a glass superfusion chamber. Slices were superfused (1.0 mL/min) for 60 minutes with Krebs buffer containing nomifensine (10 µM) and pargyline (10 µM) and maintained at 34° C., pH 7.4, with continual aeration (95% O$_2$/5% CO$_2$). Two five minute samples (5 mL each) were collected to determine basal outflow of [$^3$H]DA. The bis-quaternary ammonium analogs were added to the superfusion buffer after the collection of the second sample and remained in the buffer until 12 consecutive five minute samples were collected. Subsequently, S-nicotine (NIC; 10 µM) was added to the buffer and an additional 12 consecutive five minute samples were collected. At the end of the experiment, each slice was solubilized and the [$^3$H] content of the tissue determined.

Radioactivity in the superfusate and tissue samples was determined by liquid scintillation spectroscopy. Fractional release for tritium collected in each sample was divided by the total tritium present in the tissue at the time of sample collection and was expressed as a percentage of total tritium. Basal [$^3$H]outflow was calculated from the average of the tritium collected in the two five minute samples just before addition of the quaternary analog. The sum of the increase in collected tritium resulting from either exposure to the test compound or exposure to S-nicotine in the absence and presence of the test compound equaled total [$^3$H]overflow. [$^3$H]Overflow was calculated by subtracting the [$^3$H]outflow during an equivalent period of prestimulation from the values in samples collected during and after drug exposure. Inasmuch as the radiolabelled compounds were not separated and identified, the tritium collected in superfusate is referred to as either [3H] outflow or [$^3$H]overflow, rather than as [$^3$H]DA. [$^3$H]Overflow primarily represents [$^3$H]DA in the presence of nomifensine and pargyline in the superfusion buffer.

The bis-quaternary ammonium analogs were evaluated for their ability to evoke [$^3$H]DA release from rat striatal slices. In addition, the classical competitive nicotinic antagonist DHβE was also examined in this assay for comparison. None of the compounds examined had any significant [$^3$H]DA releasing properties in this assay in the concentration range tested.

The bis-quaternary ammonium analogs were also evaluated for their ability to inhibit NIC evoked [$^3$H]DA release. In these experiments, the striatal slices were superfused for 60 minutes with 100 nM concentration of the quaternary analogs prior to NIC (10 µM) exposure. Antagonist activity was evaluated by comparing the NIC-evoked [$^3$H]overflow in the absence and presence of the analogs. The relative order of potency of the quaternary analogs for inhibition of NIC-evoked [$^3$H]DA release from rat striatal slices is illustrated in Table 1.

TABLE 1

Bis Quaternary Ammonium Salts Inhibition of [$^3$H]NIC and [$^3$H]MLA Binding to Rat Striatal Nicotinic Receptors and Inhibition of S-Nicotine-evoked [$^3$H]Dopamine Release from Superfused Rat Striatal Slices

| Compound | [$^3$H]NIC binding | [$^3$H]MLA binding | [$^3$H]DA release |
|---|---|---|---|
| Example 1 | $K_i$ = 1.09 μM | $K_i$ > 100 μM | 11% |
| Example 2 | 11% | 4.2% | 0% |
| Example 3 | $K_i$ > 100 μM | $K_i$ > 100 μM | 31% |
| Example 4 | $K_i$ > 100 μM | $K_i$ > 100 μM | 58% |
| Example 5 | Ki = 3.63 μM | Ki = 7.64 μM | — |
| Example 6 | Ki = 5.84 μM | Ki = 3.0 μM | — |
| Example 7 | 1% | 6% | — |
| Example 8 | 0% | 0% | — |

TABLE 1-continued

Bis Quaternary Ammonium Salts Inhibition of [³H]NIC and [³H]MLA Binding to Rat Striatal Nicotinic Receptors and Inhibition of S-Nicotine-evoked [³H]Dopamine Release from Superfused Rat Striatal Slices

| Compound | [³H]NIC binding | [³H]MLA binding | [³H]DA release |
|---|---|---|---|
| Example 9 | 0% | 0% | — |
| Example 10 | $K_i$ = 0.63 μM | $K_i$ > 100 μM | 17% |
| Example 11 | $K_i$ = 5.94 μM | $K_i$ > 100 μM | 37% |
| Example 12 | $K_i$ > 100 μM | $K_i$ > 100 μM | 44% |
| Example 13 | $K_i$ > 100 μM | $K_i$ > 100 μM | 32% |
| Example 14 | 2% | 4% | — |
| Example 15 | Ki = 12.0 μM | Ki = 7.68 μM | — |

TABLE 1-continued

Bis Quaternary Ammonium Salts Inhibition of [$^3$H]NIC and [$^3$H]MLA Binding to Rat Striatal Nicotinic Receptors and Inhibition of S-Nicotine-evoked [$^3$H]Dopamine Release from Superfused Rat Striatal Slices

| Compound | [$^3$H]NIC binding | [$^3$H]MLA binding | [$^3$H]DA release |
|---|---|---|---|
| Example 16 | Ki > 100 | Ki = 15.3 μM | — |
| Example 17 | 0% | 3% | 40% |
| Example 18 | 0% | 0% | — |
| Example 19 | 0% | 0% | — |
| Example 20 | 1% | 0% | — |
| Example 23 | 2.1% | 1.2% | 25% |

TABLE 1-continued

Bis Quaternary Ammonium Salts Inhibition of [$^3$H]NIC and [$^3$H]MLA Binding to Rat Striatal Nicotinic Receptors and Inhibition of S-Nicotine-evoked [$^3$H]Dopamine Release from Superfused Rat Striatal Slices

| Compound | [$^3$H]NIC binding | [$^3$H]MLA binding | [$^3$H]DA release |
|---|---|---|---|
| Example 24 | 3.9% | 0% | 46% |
| Example 25 | 2.5% | 5.4% | 12% |
| Example 26 | 0% | 0% | 18% |

TABLE 1-continued

Bis Quaternary Ammonium Salts Inhibition of [³H]NIC and [³H]MLA Binding to Rat
Striatal Nicotinic Receptors and Inhibition of S-Nicotine-evoked [³H]Dopamine Release from
Superfused Rat Striatal Slices

| Compound | [³H]NIC binding | [³H]MLA binding | [³H]DA release |
|---|---|---|---|
| Example 27 | 4.2% | 4.2% | 23% |
| Example 28 | 1.3% | 5.0% | 19% |
| Example 29 | 0% | 2.3% | 20% |

TABLE 1-continued

Bis Quaternary Ammonium Salts Inhibition of [³H]NIC and [³H]MLA Binding to Rat Striatal Nicotinic Receptors and Inhibition of S-Nicotine-evoked [³H]Dopamine Release from Superfused Rat Striatal Slices

| Compound | [³H]NIC binding | [³H]MLA binding | [³H]DA release |
|---|---|---|---|
| Example 30 | 1.6% | 1.1% | 24% |
| Example 31 | 72% | 9.2% | 35% |
| Example 34 | 0% | 7.6% | 8% |

TABLE 1-continued
Bis Quaternary Ammonium Salts Inhibition of [$^3$H]NIC and [$^3$H]MLA Binding to Rat
Striatal Nicotinic Receptors and Inhibition of S-Nicotine-evoked [$^3$H]Dopamine Release from
Superfused Rat Striatal Slices
| Compound | [$^3$H]NIC binding | [$^3$H]MLA binding | [$^3$H]DA release |
|---|---|---|---|
| Example 35 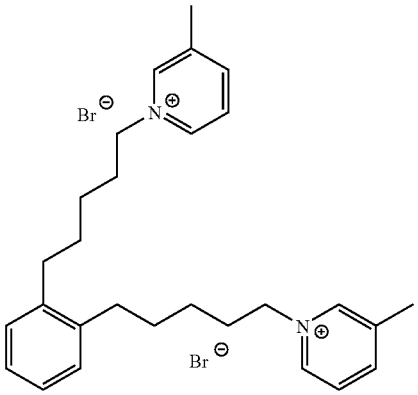 | 0% | 5.4% | 25% |
| Example 36 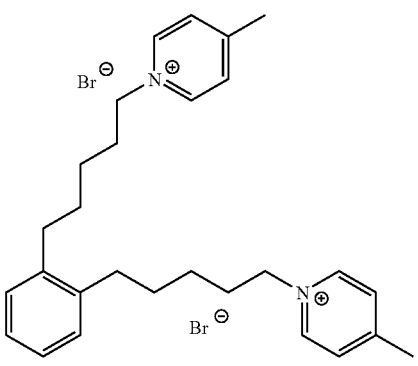 | 0% | 3.1% | 11% |
| Example 37 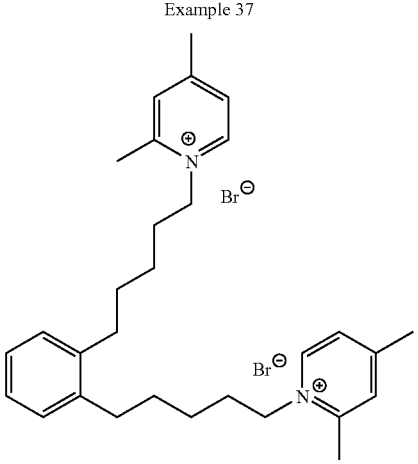 | 0% | 4.8% | 20% |

TABLE 1-continued

Bis Quaternary Ammonium Salts Inhibition of [³H]NIC and [³H]MLA Binding to Rat Striatal Nicotinic Receptors and Inhibition of S-Nicotine-evoked [³H]Dopamine Release from Superfused Rat Striatal Slices

| Compound | [³H]NIC binding | [³H]MLA binding | [³H]DA release |
|---|---|---|---|
| Example 38 | 3.0% | 4.6% | 10% |
| Example 39 | 0.7% | 0% | 47% |
| Example 40 | 0% | 6.3% | 24% |

TABLE 1-continued

Bis Quaternary Ammonium Salts Inhibition of [³H]NIC and [³H]MLA Binding to Rat
Striatal Nicotinic Receptors and Inhibition of S-Nicotine-evoked [³H]Dopamine Release from
Superfused Rat Striatal Slices

| Compound | [³H]NIC binding | [³H]MLA binding | [³H]DA release |
|---|---|---|---|
| Example 41 | 1.9% | 0% | 54% |
| Example 42 | 71% | 11% | 59% |
| Example 43 | 0.8% | 5.5% | — |

TABLE 1-continued
Bis Quaternary Ammonium Salts Inhibition of [$^3$H]NIC and [$^3$H]MLA Binding to Rat Striatal Nicotinic Receptors and Inhibition of S-Nicotine-evoked [$^3$H]Dopamine Release from Superfused Rat Striatal Slices
| Compound | [$^3$H]NIC binding | [$^3$H]MLA binding | [$^3$H]DA release |
|---|---|---|---|
| Example 44 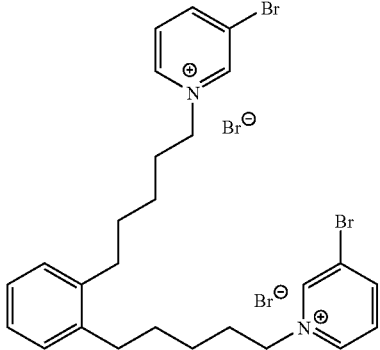 | 2.9% | 0.9% | 7% |
| Example 45 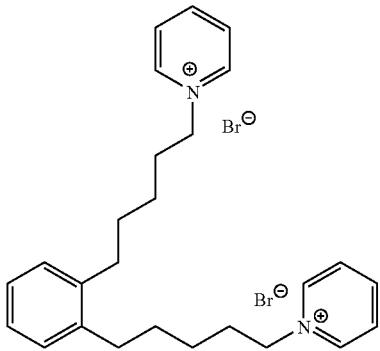 | 3.3% | 1.9% | 37% |
| Example 48 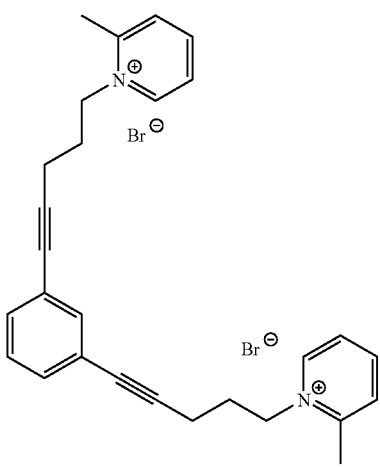 | 1.9% | 0% | 35% |

//
TABLE 1-continued
Bis Quaternary Ammonium Salts Inhibition of [³H]NIC and [³H]MLA Binding to Rat Striatal Nicotinic Receptors and Inhibition of S-Nicotine-evoked [³H]Dopamine Release from Superfused Rat Striatal Slices
| Compound | [³H]NIC binding | [³H]MLA binding | [³H]DA release |
|---|---|---|---|
| Example 49 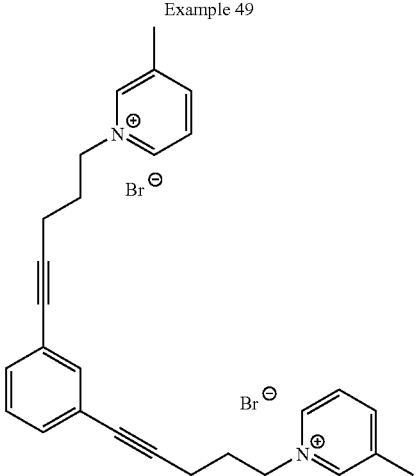 | 0.5% | 8.0% | 6% |
| Example 50 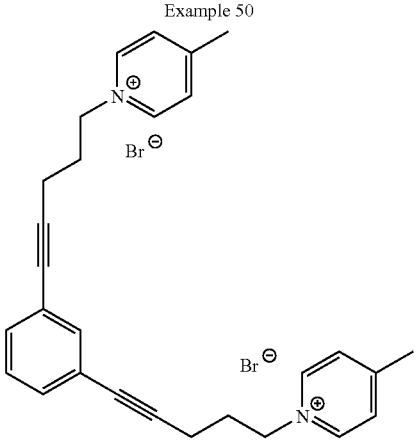 | 10% | 6.4% | 26% |
| Example 51 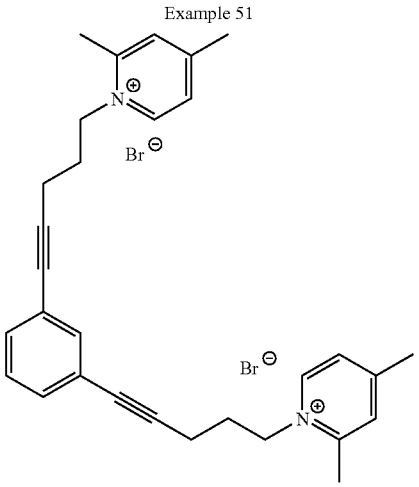 | 7.0% | 5.5% | 0% |

TABLE 1-continued
Bis Quaternary Ammonium Salts Inhibition of [$^3$H]NIC and [$^3$H]MLA Binding to Rat Striatal Nicotinic Receptors and Inhibition of S-Nicotine-evoked [$^3$H]Dopamine Release from Superfused Rat Striatal Slices
| Compound | [$^3$H]NIC binding | [$^3$H]MLA binding | [$^3$H]DA release |
|---|---|---|---|
| Example 52 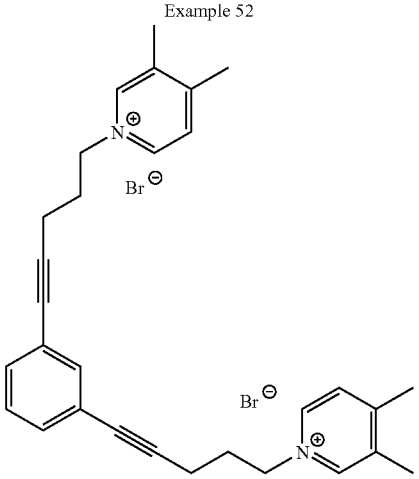 | 11% | 3.3% | 11% |
| Example 53 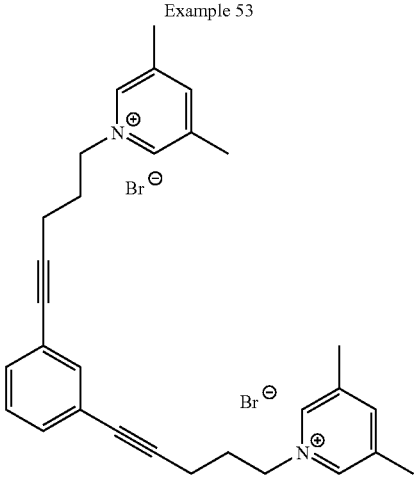 | 0% | 1.3% | 4% |
| Example 54 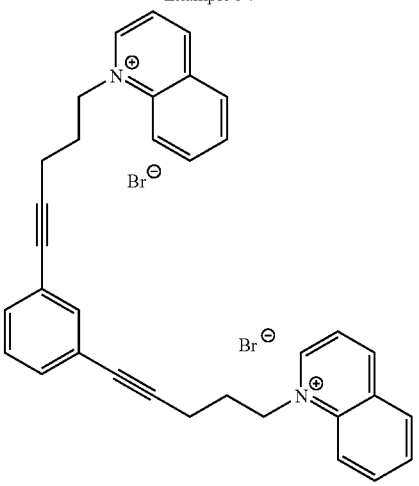 | 16% | 3.9% | 17% |

TABLE 1-continued
Bis Quaternary Ammonium Salts Inhibition of [³H]NIC and [³H]MLA Binding to Rat Striatal Nicotinic Receptors and Inhibition of S-Nicotine-evoked [³H]Dopamine Release from Superfused Rat Striatal Slices
| Compound | [³H]NIC binding | [³H]MLA binding | [³H]DA release |
|---|---|---|---|
| Example 55 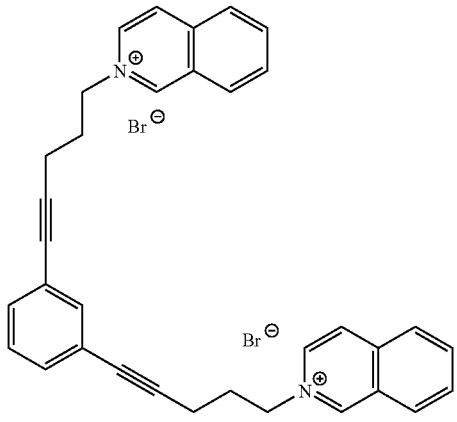 | 7.4% | 5.6% | 31% |
| Example 56 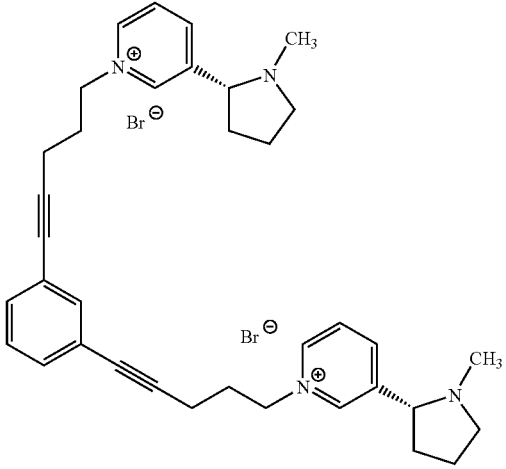 | 3.1% | 2.6% | 18% |
| Example 57 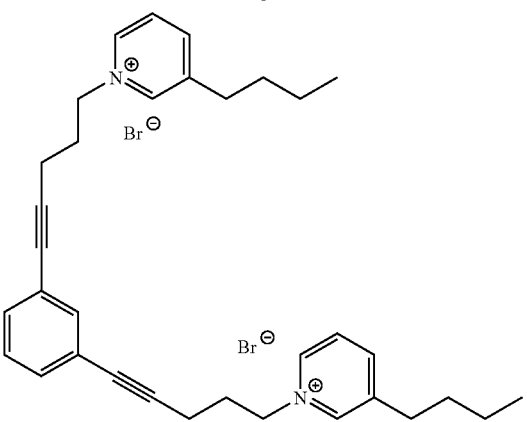 | 3.5% | 8.7% | — |

TABLE 1-continued

Bis Quaternary Ammonium Salts Inhibition of [$^3$H]NIC and [$^3$H]MLA Binding to Rat Striatal Nicotinic Receptors and Inhibition of S-Nicotine-evoked [$^3$H]Dopamine Release from Superfused Rat Striatal Slices

| Compound | [$^3$H]NIC binding | [$^3$H]MLA binding | [$^3$H]DA release |
|---|---|---|---|
| Example 58 | 3.4% | 11% | 8% |
| Example 59 | 3.6% | 4.4% | 12% |
| Example 62 | 7.2% | 0% | 62% |

TABLE 1-continued
Bis Quaternary Ammonium Salts Inhibition of [³H]NIC and [³H]MLA Binding to Rat Striatal Nicotinic Receptors and Inhibition of S-Nicotine-evoked [³H]Dopamine Release from Superfused Rat Striatal Slices
| Compound | [³H]NIC binding | [³H]MLA binding | [³H]DA release |
|---|---|---|---|
| Example 63 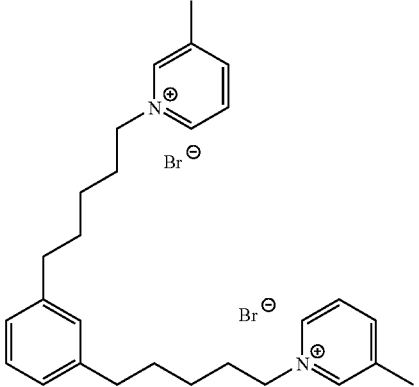 | 3.5% | 6.24% | 45% |
| Example 64 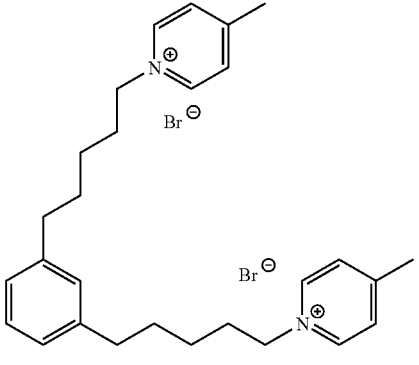 | 4.6% | 3.5% | 27% |
| Example 65 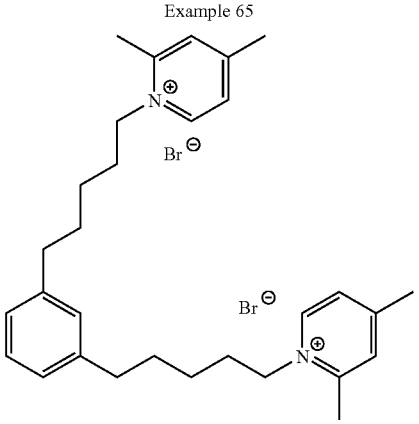 | 0.5% | 5.6% | 26% |

TABLE 1-continued
Bis Quaternary Ammonium Salts Inhibition of [$^3$H]NIC and [$^3$H]MLA Binding to Rat Striatal Nicotinic Receptors and Inhibition of S-Nicotine-evoked [$^3$H]Dopamine Release from Superfused Rat Striatal Slices
| Compound | [$^3$H]NIC binding | [$^3$H]MLA binding | [$^3$H]DA release |
|---|---|---|---|
| Example 66 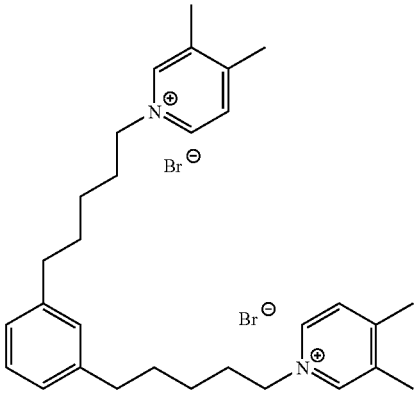 | 10.5% | 7.0% | 35% |
| Example 67 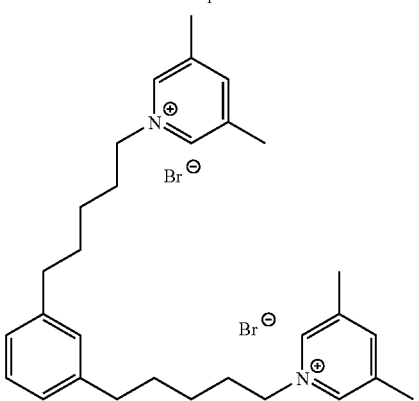 | 4.8% | 1.4% | 34% |
| Example 68 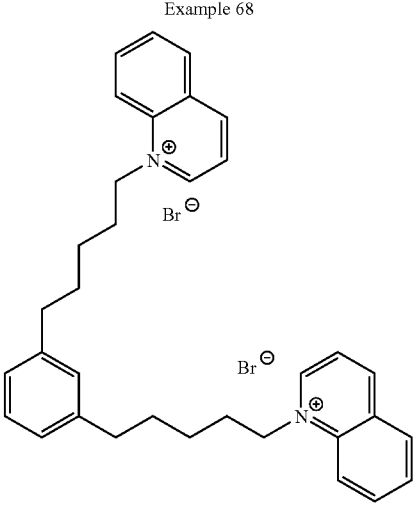 | 8.3% | 14% | 16% |

TABLE 1-continued
Bis Quaternary Ammonium Salts Inhibition of [³H]NIC and [³H]MLA Binding to Rat Striatal Nicotinic Receptors and Inhibition of S-Nicotine-evoked [³H]Dopamine Release from Superfused Rat Striatal Slices
| Compound | [³H]NIC binding | [³H]MLA binding | [³H]DA release |
|---|---|---|---|
| Example 69 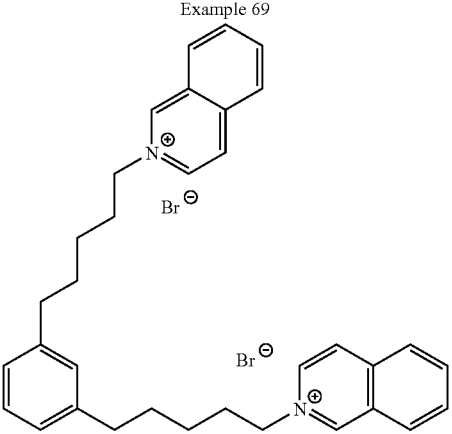 | 8.8% | 5.2% | 0% |
| Example 70 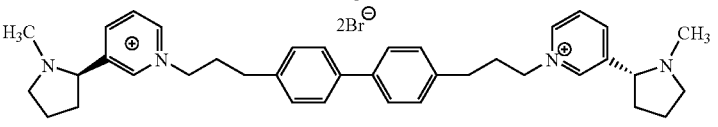 | 12% | 11% | 8% |
| Example 71 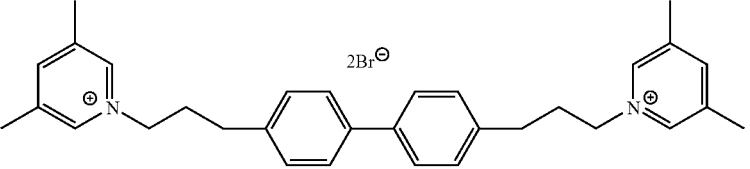 | 1.6% | 3.6% | — |
| Example 72 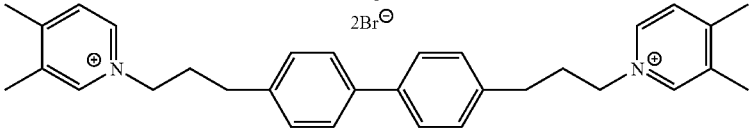 | 0% | 5.5% | — |
| Example 73 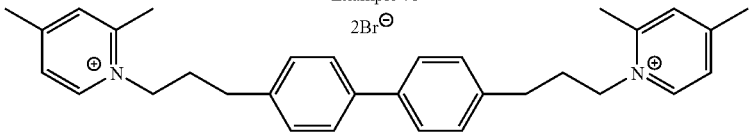 | 3.0% | 0.6% | — |
| Example 74 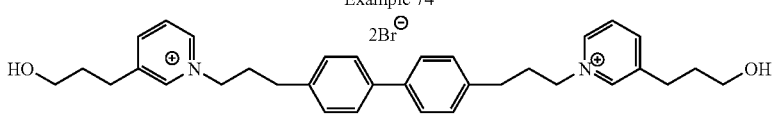 | 2.0% | 5.8% | — |
| Example 75 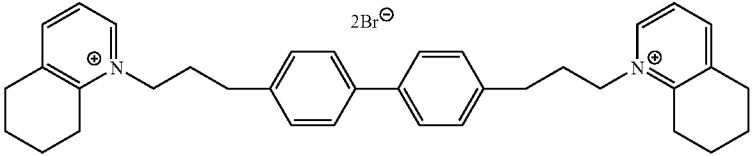 | 0.4% | 10% | — |

TABLE 1-continued
Bis Quaternary Ammonium Salts Inhibition of [³H]NIC and [³H]MLA Binding to Rat Striatal Nicotinic Receptors and Inhibition of S-Nicotine-evoked [³H]Dopamine Release from Superfused Rat Striatal Slices
| Compound | [³H]NIC binding | [³H]MLA binding | [³H]DA release |
|---|---|---|---|
| Example 76 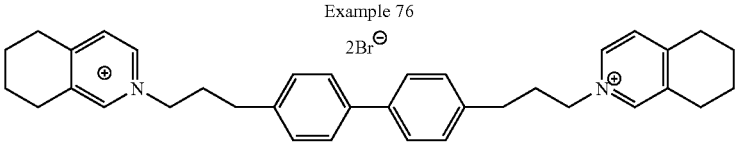 | 0% | 5.1% | — |
| Example 77 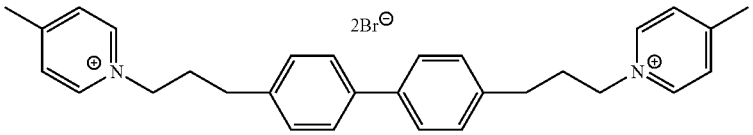 | 0% | 0% | — |
| Example 78 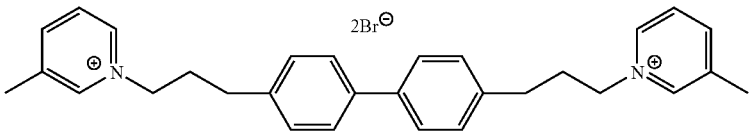 | 0% | 5.5% | 44% |
| Example 79 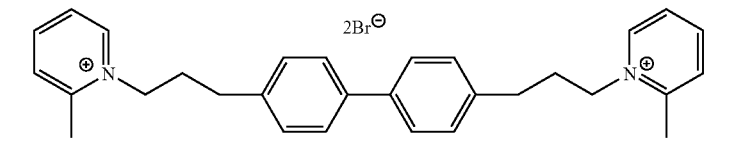 | 0% | 0% | — |
| Example 80 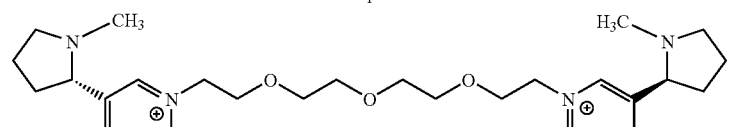 | 7.2% | 13% | — |
| Example 81 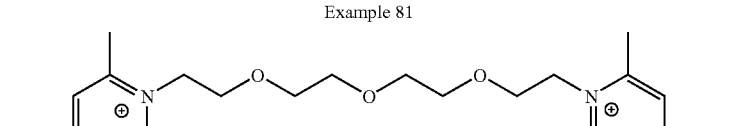 | 8.5% | 17% | — |
| Example 82 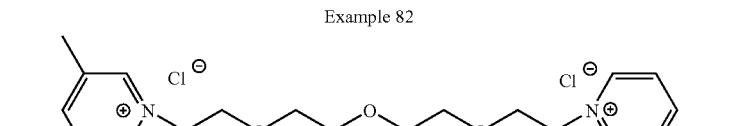 | 17% | 13% | 58% |
| Example 83 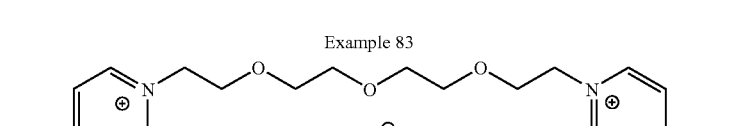 | 15% | 7.0% | 53% |

TABLE 1-continued

Bis Quaternary Ammonium Salts Inhibition of [$^3$H]NIC and [$^3$H]MLA Binding to Rat Striatal Nicotinic Receptors and Inhibition of S-Nicotine-evoked [$^3$H]Dopamine Release from Superfused Rat Striatal Slices

| Compound | [$^3$H]NIC binding | [$^3$H]MLA binding | [$^3$H]DA release |
|---|---|---|---|
| Example 84 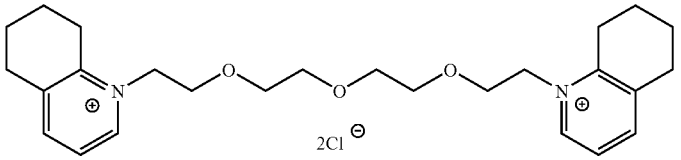 | 0% | 4.7% | — |
| Example 85 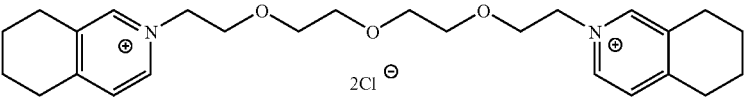 | 6.0% | 16% | — |
| Example 86 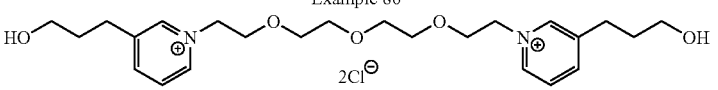 | 8.2% | 8.5% | — |
| Example 87 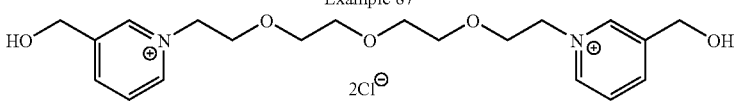 | 8.2% | 11% | — |
| Example 88 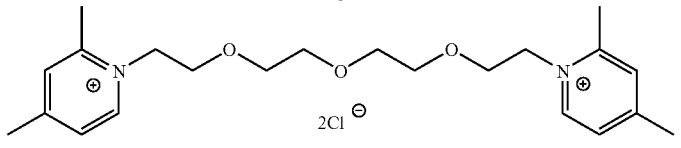 | 0% | 2.9% | — |
| Example 89 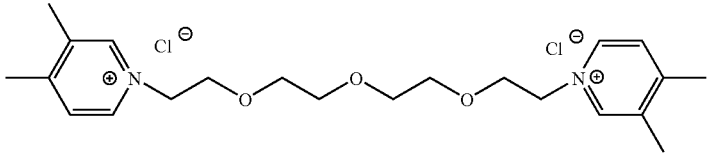 | 13% | 14% | |
| Example 90 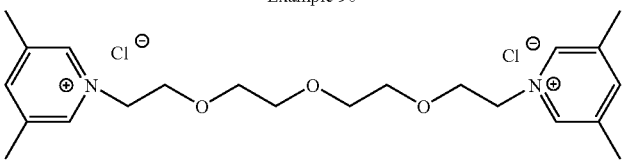 | 10% | 5.0% | — |
| Example 91 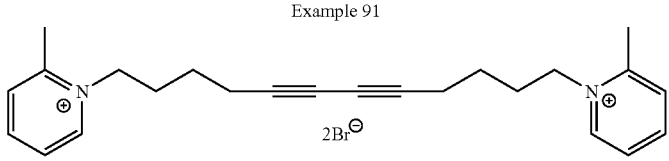 | $K_i = 4.4\ \mu M$ | $K_i = 23.9\ \mu M$ | 6% |
| Example 92 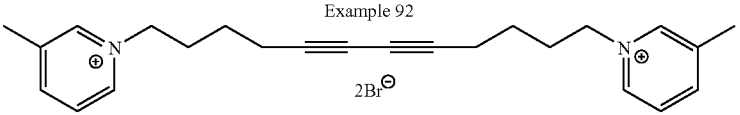 | $K_i = 6.36\ \mu M$ | $K_i > 100\ \mu M$ | 18% |

TABLE 1-continued

Bis Quaternary Ammonium Salts Inhibition of [³H]NIC and [³H]MLA Binding to Rat Striatal Nicotinic Receptors and Inhibition of S-Nicotine-evoked [³H]Dopamine Release from Superfused Rat Striatal Slices

| Compound | [³H]NIC binding | [³H]MLA binding | [³H]DA release |
|---|---|---|---|
| Example 93 | $K_i$ = 8.93 μM | $K_i$ = 5.11 μM | 19% |
| Example 94 | Ki = 8.6± μM | Ki = 24.1 μM | 21% |
| Example 95 | $K_i$ > 100 μM | Ki = 25.6 μM | IC$_{50}$, > 1 μM |
| Example 96 | Ki = 11.3 μM | Ki = 5.36 μM | — |
| Example 97 | 2.75 ± 0.40 ($K_i$) | $K_i$ > 100 μM | 21% |
| Example 98 | $K_i$ = 8.50 μM | $K_i$ > 100 μM | 29% |
| Example 99 | Ki = 8.04 μM | Ki = 0.87 μM | 14% |
| Example 100 | 3% | 0% | 31% |
| Example 101 | 0% | 0% | 14% |

TABLE 1-continued

Bis Quaternary Ammonium Salts Inhibition of [³H]NIC and [³H]MLA Binding to Rat Striatal Nicotinic Receptors and Inhibition of S-Nicotine-evoked [³H]Dopamine Release from Superfused Rat Striatal Slices

| Compound | [³H]NIC binding | [³H]MLA binding | [³H]DA release |
|---|---|---|---|
| Example 102 | 9.4% | 12% | — |
| Example 103 | 9.6% | 12% | — |
| Example 104 | 19% | 16% | — |

$^a$Data are % inhibition at 100 nM concentration of the bis-quaternary ammonium analogs for at least 1-3 independent experiments; with the exception of when a Ki value in μM is provided, in which case a full concentration effect was evaluated. Specific binding in the [³H]NIC binding assay is calculated as the difference between the total binding of 3 nM [³H]NIC and nonspecific binding in the presence of 10 μM cold cytisine. Specific binding for the [³H]MLA binding assay is calculated as the difference between the total binding of 2.5 nM [³H]MLA to the receptors alone and its nonspecific binding in the presence of 1 μM cold S-nicotine. Analog-induced inhibition of S-nicotine-evoked [³H]DA release is calculated as a percent of that in the absence of the bis-quaternary ammonium analog.

It will be appreciated that, although specific embodiments of the invention have been described herein for purposes of illustration, various modifications may be made without departing from the spirit and scope of the invention. All such modifications and variations are intended to be included herein within the scope of this disclosure and the present invention and protected by the following claims.

We claim:

1. A compound of Formula (I)

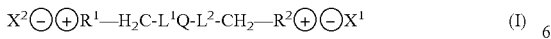

wherein $X^{1\ominus}$ and $X^{2\ominus}$ are each independently chloride or bromide;

wherein -$L_1$-Q-$L_2$- is —(CH$_2$)$_4$-1,2-phenylene-(CH$_2$)$_4$—, —(CH$_2$)$_4$-1,3-phenylene-(CH$_2$)$_4$—, —(CH$_2$)$_3$-1,4-phenylene-(CH$_2$)$_3$—, —(CH$_2$)$_2$-4,4'-biphenylene-(CH$_2$)$_2$—, —(CH$_2$)$_2$—C≡C-1,2-phenylene-C≡C—(CH$_2$)$_2$—, —(CH$_2$)$_2$—C≡C-1,3-phenylene-C≡C—(CH$_2$)$_2$—, —CH$_2$—C≡C-1,4-phenylene-C≡C—CH$_2$—, —C≡C-4,4'-biphenylene-C≡C—, —(CH$_2$)$_3$—CH=CH—CH=CH—(CH$_2$)$_3$—, or —(CH$_2$)$_3$—C≡C—C≡C—(CH$_2$)$_3$—;

wherein each of R$^1$ and R$^2$ are attached to —H$_2$C-L$_1$-Q-L$_2$-Ch$_2$— via a quaternized nitrogen and R$^1$ and R$^2$ are each independently a six membered nitrogen containing ring as shown in formula (IIA):

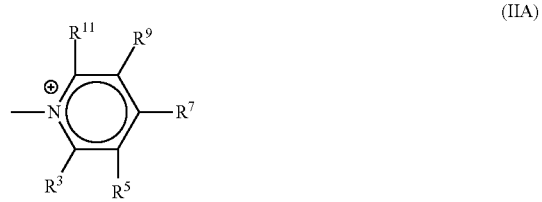

R$^3$ is hydrogen or methyl,

R$^5$ is hydrogen, methyl, ethyl, butyl, phenyl, 1-methyl-2-pyrrolidinyl, bromo, hydroxymethyl or hydroxypropyl;

R$^7$ is hydrogen or methyl;

R$^9$ is hydrogen or methyl; and

R$^{11}$ is hydrogen; or quinoline, isoquinoline, tetrahydroquinoline or tetrahydroisoquinoline.

2. The compound of claim 1, wherein R$^1$ and R$^2$ are pyridinium rings.

3. The compound of claim 1, wherein $R^1$ and $R^2$ are each independently, the six membered nitrogen containing ring as shown in formula (IIA):

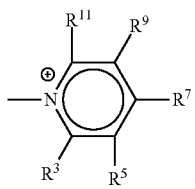

(IIA)

wherein
$R^3$ is hydrogen or methyl,
$R^5$ is hydrogen, methyl, ethyl, butyl, phenyl, 1-methyl-2-pyrrolidinyl, bromo, hydroxymethyl or hydroxypropyl;
$R^7$ is hydrogen or methyl;
$R^9$ is hydrogen or methyl; and
$R^{11}$ is hydrogen.

4. The compound of claim 1, wherein:
$R^1$ and $R^2$ are quinoline, isoquinoline, tetrahydroquinoline or tetrahydroisoquinoline.

5. The compound of claim 1 selected from the group consisting of:
cis-cis-N,N'-(dodeca-5,7-diene-1,12-diyl)-bis-[3-(2'-S-1-methyl-pyrrolidin-2-yl)-pyridinium]dibromide;
cis-cis-N,N'-(dodeca-5,7-diene-1,12-diyl)-bis-(2-methyl-pyridinium)dibromide;
cis-cis-N,N'-(dodeca-5,7-diene-1,12-diyl)-bis-(3-methyl-pyridinium)dibromide;
cis-cis-N,N'-(dodeca-5,7-diene-1,12-diyl)-bis-(4-methyl-pyridinium)dibromide;
cis-cis-N,N'-(dodeca-5,7-diene-1,12-diyl)-bis-(5,6,7,8-tetrahydro-quinolinium) dibromide;
cis-cis-N,N'-(dodeca-5,7-diene-1,12-diyl)-bis-(5,6,7,8-tetrahydro-isoquinolinium) dibromide;
cis-cis-N,N'-(dodeca-5,7-diene-1,12-diyl)-bis-(2,4-dimethyl-pyridinium)dibromide;
cis-cis-N,N'-(dodeca-5,7-diene-1,12-diyl)-bis-(3,4-dimethyl-pyridinium)dibromide;
cis-cis-N,N'-(dodeca-5,7-diene-1,12-diyl)-bis-(3,5-dimethyl-pyridinium)dibromide;
N,N'-[1,4-phenylenedi-(4-butanyl)]-bis-[3-(2'-S-1-methyl-pyrrolidin-2-yl)-pyridinium]dibromide;
N,N'-[1,4-phenylenedi-(4-butanyl)]-bis-(2-methylpyridinium)dibromide;
N,N'-[1,4-phenylenedi-(4-butanyl)]-bis-(3-methylpyridinium)dibromide;
N,N'-[1,4-phenylenedi-(4-butanyl)]-bis-(4-methylpyridinium)dibromide;
N,N'-[1,4-phenylenedi-(4-butanyl)]-bis-(3-ethylpyridinium)dibromide;
N,N'-[1,4-phenylenedi-(4-butanyl)]-bis-(5,6,7,8-tetrahydroquinolinium) dibromide;
N,N'-[1,4-phenylenedi-(4-butanyl)]-bis-(5,6,7,8-tetrahydroisoquinolinium) dibromide;
N,N'-[1,4-phenylenedi-(4-butanyl)]-bis-[3-(3-hydroxypropyl)-pyridinium]dibromide;
N,N'-[1,4-phenylenedi-(4-butanyl)]-bis-(2,4-dimethylpyridinium)dibromide;
N,N'-[1,4-phenylenedi-(4-butanyl)]-bis-(3,4-dimethylpyridinium)dibromide;
N,N'-[1,4-phenylenedi-(4-butanyl)]-bis-(3,5-dimethylpyridinium)dibromide;
1,2-bis-[5-(2-methyl-pyridinium)-pent-1-ynyl]-benzene dibromide;
1,2-bis-[5-(3-methyl-pyridinium)-pent-1-ynyl]-benzene dibromide;
1,2-bis-[5-(4-methyl-pyridinium)-pent-1-ynyl]-benzene dibromide;
1,2-bis-[5-(2,4-dimethyl-pyridinium)-pent-1-ynyl]-benzene dibromide;
1,2-bis-[5-(3,4-dimethyl-pyridinium)-pent-1-ynyl]-benzene dibromide;
1,2-bis-[5-(3,5-dimethyl-pyridinium)-pent-1-ynyl]-benzene dibromide;
1,2-bis-(5-quinolinium-pent-1-ynyl)-benzene dibromide;
1,2-bis-(5-isoquinolinium-pent-1-ynyl)-benzene dibromide;
1,2-bis-(5-S-nicotinium-pent-1-ynyl)-benzene dibromide;
1,2-bis-[5-(2-methyl-pyridinium)-pentyl]-benzene dibromide;
1,2-bis-[5-(3-methyl-pyridinium)-pentyl]-benzene dibromide;
1,2-bis-[5-(4-methyl-pyridinium)-pentyl]-benzene dibromide;
1,2-bis-[5-(2,4-dimethyl-pyridinium)-pentyl]-benzene dibromide;
1,2-bis-[5-(3,4-dimethyl-pyridinium)-pentyl]-benzene dibromide;
1,2-bis-[5-(3,5-methyl-pyridinium)-pentyl]-benzene dibromide;
1,2-bis-(5-quinolinium-pentyl)-benzene dibromide;
1,2-bis-(5-isoquinolinium-pentyl)-benzene dibromide;
1,2-bis-(5-S-nicotinium-pentyl)-benzene dibromide;
1,2-bis-[5-(3-n-butyl-pyridinium)-pentyl]-benzene dibromide;
1,2-bis-[5-(3-bromo-pyridinium)-pentyl]-benzene dibromide;
1,2-bis-(5-pyridinium-pentyl)-benzene dibromide;
1,3-bis-[5-(2-methyl-pyridinium)-pent-1-ynyl]-benzene dibromide;
1,3-bis-[5-(3-methyl-pyridinium)-pent-1-ynyl]-benzene dibromide;
1,3-bis-[5-(4-methyl-pyridinium)-pent-1-ynyl]-benzene dibromide;
1,3-bis-[5-(2,4-dimethyl-pyridinium)-pent-1-ynyl]-benzene dibromide;
1,3-bis-[5-(3,4-dimethyl-pyridinium)-pent-1-ynyl]-benzene dibromide;
1,3-bis-[5-(3,5-dimethyl-pyridinium)-pent-1-ynyl]-benzene dibromide;
1,3-bis-(5-quinolinium-pent-1-ynyl)-benzene dibromide;
1,3-bis-(5-isoquinolinium-pent-1-ynyl)-benzene dibromide;
1,3-bis-(5-S-nicotinium-pent-1-ynyl)-benzene dibromide;
1,3-bis-[5-(3-n-butyl-pyridinium)-pent-1-ynyl]-benzene dibromide;
1,3-bis-[5-(3-phenyl-pyridinium)-pent-1-ynyl]-benzene dibromide;
1,3-bis-(5-pyridinium-pent-1-ynyl)-benzene dibromide;
1,3-bis-[5-(2-methyl-pyridinium)-pentyl]-benzene dibromide;
1,3-bis-[5-(3-methyl-pyridinium)-pentyl]-benzene dibromide;
1,3-bis-[5-(4-methyl-pyridinium)-pentyl]-benzene dibromide;
1,3-bis-[5-(2,4-dimethyl-pyridinium)-pentyl]-benzene dibromide;
1,3-bis-[5-(3,4-dimethyl-pyridinium)-pentyl]-benzene dibromide;

1,3-bis-[5-(3,5-dimethyl-pyridinium)-pentyl]-benzene dibromide;
1,3-bis-(5-quinolinium-pentyl)-benzene dibromide;
1,3-bis-(5-isoquinolinium-pentyl)-benzene dibromide;
N,N'-[(1,1'-biphenyl)-4,4'-di-(3-propanyl)]-bis-[3-(2'-S-1-methyl-pyrrolidin-2-yl)-pyridinium]dibromide;
N,N'-[(1,1'-biphenyl)-4,4'-di-(3-propanyl)]-bis-(3,5-dimethylpyridinium) dibromide;
N,N'-[(1,1'-biphenyl)-4,4'-di-(3-propanyl)]-bis-(3,4-dimethylpyridinium) dibromide;
N,N'-[(1,1'-biphenyl)-4,4'-di-(3-propanyl)]-bis-(2,4-dimethylpyridinium) dibromide;
N,N'-[(1,1'-biphenyl)-4,4'-di-(3-propanyl)]-bis-[3-(3-hydroxy-propyl)-pyridinium]dibromide;
N,N'-[(1,1'-biphenyl)-4,4'-di-(3-propanyl)]-bis-[5,6,7,8-tetrahydroquinolinium]dibromide;
N,N'-[(1,1'-biphenyl)-4,4'-di-(3-propanyl)]-bis-[5,6,7,8-tetrahydroisoquinolinium]dibromide;
N,N'-[(1,1'-biphenyl)-4,4'-di-(3-propanyl)]-bis-(4-methylpyridinium)dibromide;
N,N'-[(1,1'-biphenyl)-4,4'-di-(3-propanyl)]-bis-(3-methylpyridinium)dibromide;
N,N'-[(1,1'-biphenyl)-4,4'-di-(3-propanyl)]-bis-(2-methylpyridinium)dibromide;
N,N'-(5,7-dodecadiyn-1,12-diyl)-bis-(2-methylpyridinium)dichloride;
N,N'-(5,7-dodecadiyn-1,12-diyl)-bis-(3-methylpyridinium)dichloride;
N,N'-(5,7-dodecadiyn-1,12-diyl)-bis-(4-methylpyridinium)dichloride;
N,N'-(5,7-dodecadiyn-1,12-diyl)-bis-(3,4-dimethylpyridinium)dichloride;
N,N'-(5,7-dodecadiyn-1,12-diyl)-bis-(3,5-dimethylpyridinium)dichloride;
N,N'-(5,7-dodecadiyn-1,12-diyl)-bis-(5,6,7,8-tetrahydroisoquinolinium)dichloride;
N,N'-[(1,4-phenylene)-bis-(4-butynyl)]-bis-(3-methyl-pyridinium)dibromide;
N,N'-[(1,4-phenylene)-bis-(4-butynyl)]-bis-(4-methyl-pyridinium)dibromide;
N,N'-[(1,4-phenylene)-bis-(4-butynyl)]-bis-(5,6,7,8-tetrahydroisoquiolinium) dibromide;
N,N'-[(1,4-phenylene)-bis-(4-butynyl)]-bis-(3,4-dimethyl-pyridinium)dibromide;
N,N'-[(1,4-phenylene)-bis-(4-butynyl)]-bis-(3,5-dimethyl-pyridinium)dibromide;
N,N'-[1,1'-biphenyl)-4,4'-di-(1-propyn-3-yl)]-bis-(3-methylpyridinium)dibromide;
N,N'-[(1,1'-biphenyl)-4,4'-di-(1-propyn-3-yl)]-bis-(4-methylpyridinium)dibromide; and
N,N'-[(1,1'-biphenyl)-4,4'-di-(1-propyn-3-yl)]-bis-(3,4-dimethylpyridinium) dibromide.

6. A composition comprising a pharmaceutically acceptable carrier and a compound of claim 1.

7. A composition comprising a pharmaceutically acceptable carrier and a compound of claim 2.

8. A composition comprising a pharmaceutically acceptable carrier and a compound of claim 3.

9. A composition comprising a pharmaceutically acceptable carrier and a compound of claim 4.

10. A composition comprising a pharmaceutically acceptable carrier and a compound of claim 5.

* * * * *